US010772987B2

(12) United States Patent
Jongpaiboonkit et al.

(10) Patent No.: US 10,772,987 B2
(45) Date of Patent: Sep. 15, 2020

(54) MINERAL COATED SCAFFOLDS

(71) Applicant: Tissue Regeneration Systems, Inc., Seattle, WA (US)

(72) Inventors: Leenaporn Jongpaiboonkit, Madison, WI (US); William L. Murphy, Madison, WI (US)

(73) Assignee: TRS Holdings LLC, Ann Arbor, MI (US)

( * ) Notice: Subject to any disclaimer, the term of this patent is extended or adjusted under 35 U.S.C. 154(b) by 0 days.

(21) Appl. No.: 14/637,345

(22) Filed: Mar. 3, 2015

(65) Prior Publication Data

US 2015/0238655 A1  Aug. 27, 2015

Related U.S. Application Data

(63) Continuation-in-part of application No. 13/036,470, filed on Feb. 28, 2011, now abandoned, which is a continuation-in-part of application No. 11/927,322, filed on Oct. 29, 2007, now Pat. No. 9,439,948, application No. 14/637,345, filed on Mar. 3, 2015, which is a continuation-in-part of application No. 13/879,178, filed as application No. PCT/US2009/058419 on Sep. 25, 2009, application No. 14/637,345, filed on Mar. 3, 2015, which is a
(Continued)

(51) Int. Cl.
| | |
|---|---|
| *A61L 27/32* | (2006.01) |
| *C08K 3/22* | (2006.01) |
| *C08K 3/34* | (2006.01) |
| *C08K 3/40* | (2006.01) |
| *B32B 7/00* | (2019.01) |
| *B32B 15/08* | (2006.01) |
| *B32B 27/28* | (2006.01) |
| *C08K 3/08* | (2006.01) |
| *A61L 27/18* | (2006.01) |
| *A61L 27/56* | (2006.01) |
| *A61K 38/18* | (2006.01) |
| *A61K 38/30* | (2006.01) |
| *A61F 2/44* | (2006.01) |
| *A61F 2/30* | (2006.01) |
| *A61F 2/28* | (2006.01) |

(52) U.S. Cl.
CPC ............ *A61L 27/32* (2013.01); *A61F 2/4455* (2013.01); *A61K 38/1825* (2013.01); *A61K 38/1841* (2013.01); *A61K 38/1858* (2013.01); *A61K 38/1875* (2013.01); *A61K 38/30* (2013.01); *A61L 27/18* (2013.01); *A61L 27/56* (2013.01); *A61F 2002/2817* (2013.01); *A61F 2002/3008* (2013.01); *A61F 2002/30011* (2013.01); *A61F 2002/30032* (2013.01); *A61F 2002/30056* (2013.01); *A61F 2002/30062* (2013.01); *A61F 2002/30064* (2013.01); *A61F 2002/3092* (2013.01); *A61F 2002/30303* (2013.01); *A61F 2002/30578* (2013.01); *A61F 2002/30785* (2013.01); *A61F 2002/30789* (2013.01); *A61F 2002/30838* (2013.01); *A61F 2002/30878* (2013.01); *A61F 2002/30884* (2013.01); *A61F 2002/30892* (2013.01); *A61F 2002/30899* (2013.01); *A61F 2002/4485* (2013.01); *A61F 2210/0004* (2013.01); *A61F 2310/00017* (2013.01); *A61F 2310/00023* (2013.01); *A61F 2310/00029* (2013.01); *A61F 2310/00089* (2013.01); *A61F 2310/0097* (2013.01); *A61F 2310/00113* (2013.01); *A61F 2310/00131* (2013.01); *A61F 2310/00149* (2013.01); *A61F 2310/00155* (2013.01); *A61F 2310/00293* (2013.01); *A61F 2310/00796* (2013.01); *A61F 2310/00976* (2013.01); *A61L 2400/18* (2013.01); *A61L 2420/02* (2013.01); *A61L 2420/06* (2013.01); *A61L 2430/02* (2013.01); *A61L 2430/38* (2013.01)

(58) Field of Classification Search
USPC .................................. 523/105, 115; 427/343
See application file for complete search history.

(56) References Cited

U.S. PATENT DOCUMENTS

| | | | |
|---|---|---|---|
| 5,944,754 A | * | 8/1999 | Vacanti .................. A61K 47/10 602/48 |
| 6,471,993 B1 | | 10/2002 | Shastri et al. |
| 6,541,022 B1 | | 4/2003 | Murphy et al. |

(Continued)

FOREIGN PATENT DOCUMENTS

| | | |
|---|---|---|
| JP | 2004530675 | 10/2004 |
| WO | WO2002085330 | 10/2002 |

(Continued)

OTHER PUBLICATIONS

Akhtar et al., Antisense oligonucleotide delivery to cultured macrophages is improved by incorporation into sustained-release biodegradable polymer microspheres, 1997, International Journal of Pharmaceuticals, vol. 151, pp. 57-67.

(Continued)

Primary Examiner — Tae H Yoon

(74) Attorney, Agent, or Firm — Sorell, Lenna & Schmidt, LLP

(57) ABSTRACT

Provided is a composition for a scaffold having a mineral coating similar to bone. Also provided is a method for mineral coating a scaffold so as to promote mineral coating of the scaffold with a plate-like nanostructure and a carbonate-substituted, calcium-deficient hydroxyapatite phase.

29 Claims, 10 Drawing Sheets

Related U.S. Application Data continuation-in-part of application No. 13/407,441, filed on Feb. 28, 2012, now Pat. No. 9,943,410.

(60) Provisional application No. 60/855,235, filed on Oct. 30, 2006, provisional application No. 61/100,062, filed on Sep. 25, 2008, provisional application No. 61/447,352, filed on Feb. 28, 2011.

(56) References Cited

U.S. PATENT DOCUMENTS

| | | | |
|---|---|---|---|
| 6,743,779 | B1 | 6/2004 | Unger et al. |
| 6,767,928 | B1 | 7/2004 | Murphy et al. |
| 7,323,208 | B2 * | 1/2008 | Ma .............................. C08J 9/36 427/2.1 |
| 9,439,948 | B2 * | 9/2016 | Lin ........................ A61F 2/4455 |
| 2002/0155144 | A1 | 10/2002 | Troczynski et al. |
| 2004/0023852 | A1 | 2/2004 | Roberts et al. |
| 2004/0052865 | A1 | 3/2004 | Gower et al. |
| 2005/0100578 | A1 * | 5/2005 | Schmid ...................... A61F 2/28 424/423 |
| 2005/0249697 | A1 | 11/2005 | Uhrich et al. |
| 2007/0059437 | A1 | 3/2007 | Murphy et al. |
| 2008/0090760 | A2 | 4/2008 | Hembrough et al. |
| 2008/0095817 | A1 | 4/2008 | Murphy |
| 2008/0095820 | A1 | 4/2008 | Kumta et al. |
| 2011/0250290 | A1 * | 10/2011 | Marques ................ A01N 59/16 424/618 |

FOREIGN PATENT DOCUMENTS

| | | |
|---|---|---|
| WO | WO2004085998 | 10/2004 |
| WO | WO2008070355 | 6/2008 |
| WO | WO2008082766 | 7/2008 |

OTHER PUBLICATIONS

Bajpai et al., Study of biomineralization of poly(vinyl alcohol)-based scaffolds using an alternate soaking approach, 2007, Polymer International, vol. 56, No. 4, pp. 557-568, vol. 56, No. 4.

Baron, Molecular Mechanisms of Bone Resorption by the Osteoclast, 1989, The Anatomical Record, vol. 224, pp. 317-324.

Barrere et al., Nano-scale study of the nucleation and growth of calcium phosphate coating on titanium implants, 2004, Biomaterials, vol. 25, No. 14, pp. 2901-2910.

Berchane et al., About mean diameter and size distributions of poly(lactide-co-glycolide)(PLG) microspheres, 2006, Journal of Microencapsulation, vol. 23, No. 5, pp. 539-552.

Boyer et al., Experimental Studies of Restricted Protein Diffusion in an Agarose Matrix, 1992, AIChE Journal, 1992, vol. 38, No. 2, pp. 259-272.

Chesko et al., An Investigation of the factors Controlling the Adsorption of Protein Antigens to Anionic PLG Microparticles, 2005, Journal of Pharmaceutical Sciences, vol. 94, No. 11., pp. 2510-2519.

Colman et al., Rapid Purification of Plasmid DNAs by Hydroxyapatite Chromatography, 1978, European Journal of Biochemistry, vol. 91, pp. 303-310.

Coombes et al., Biodegradable polymeric microparticles for drug delivery and vaccine formulation: the surface attachment of hydrophilic species using the concept of poly(ethylene glycol) anchoring segments, 1997, Biomaterials, vol. 18, No. 17, pp. 1153-1161.

Defail et al., Controlled release of bioactive doxorubicin from microspheres embedded within gelatin scaffolds, 2006, Journal of Biomedical Materials Research Part A, vol. 79A, pp. 954-962.

Driessens et al., Biological Calcium Phosphates and Their Role in the Physiology of Bone and Dental Tissues I. Composition and Solubility of Calcium Phosphates, 1978, Calcified Tissue Research vol. 26, pp. 127-137.

Ducheyne et al., Bioactive ceramics: the effect of surface reactivity on bone formation and bone cell function, 1999, Biomaterials, vol. 20, pp. 2287-2303.

Eniola et al., Characterization of biodegradable drug delivery vehicleswith the adhesive properties of leukocytes, 2002, Biomaterials, vol. 23, pp. 2167-2177.

Extended European Search Report dated Jul. 2, 2014 in corresponding Application No. EP 09816920.4, 7 pages.

Fazan et al., Dissolution behavior of plasma-sprayed hydroxyapatite coatings, 2000, Journal of Materials Science: Materials in Medicine, vol. 11, No. 12, pp. 787-792.

Fernandez-Pradas et al., Deposition of hydroxyapatite thin films by excimer laser ablation, Thin Solid Films, vol. 317, pp. 393-396, 1998.

Ferreira et al., Human Embryoid Bodies Containing Nano- and Microparticulate Delivery Vehicles, 2008, Advanced Materials, vol. 20, 7 pages, and Supplementary Materials, 11 pages, total of 18 pages.

Fischer et al., One-step preparation of polyelectrolyte-coated PLGA microparticles and their functionalization with model ligands, 2006, Journal of Controlled Release, vol. 111, pp. 135-144.

Gao et al., Bioinspired Ceramic Thin Film Processing: Present Status and Future Perspectives, 2005, Crystal Growth & Design, vol. 5, No. 5, pp. 1983-2017.

Gledhill et al., In vitro dissolution behaviour of two morphologically different thermally sprayed hydroxyapatite coatings, 2001, Biomaterials, vol. 22, pp. 695-700.

Green et al., Mineralized polysaccharide capsules as biomimetic microenvironments for cell, gene, and growth factor delivery in tissue engineering, 2006, Soft Matter, vol. 2, pp. 732-737.

Habibovic et al., Osteoinduction by biomaterials-Physicochemical and structural influences, 2006, Journal of Biomedical Materials Research Part A, vol. 77A, No. 4, pp. 747-762.

He et al., Nucleation of apatite crystals in vitro by self-assembled dentin matrix protein 1, 2003, Nature Materials, vol. 2, No. 8, pp. 552-558.

He et al., Spatially and Temporally Controlled Biomineralization is Facilitated by Interaction Between Self-Assembled Dentin Matrix Protein 1 and Calcium Phosphate Nuclei in Solution, 2005, Biochemistry, vol. 44, No. 49, pp. 16140-161485.

Heinonen et al., A New and Convenient Colorimetric Determination of Inorganic Orthophosphate and Its Application to the Assay of Inorganic Pyrophosphatase, 1981, Analytical Biochemistry, vol. 113, pp. 313-317.

Hong et al., Hydroxyapatite/bacterial cellulose composites synthesized via a biomimetic route, 2006, Materials Letters, vol. 60, No. 13-14, pp. 1710-1713.

Hughes et al., Adsorption of bovine serum albumin onto hydroxyapatite, 1995, Biomaterials, vol. 16, pp. 697-702.

International Search Report and Written Opinion dated Dec. 24, 2009 in corresponding Application No. PCT/US09/58419 filed Sep. 25, 2009, 13 pages.

Jabbarzadeh et al., Apatite nano-crystalline surface modification of poly(lactide-co-glycolide) sintered microsphere scaffolds for bone tissue engineering: implications for protein adsorption, 2007, Journal of Biomaterials Science Polymer Edition, vol. 18, No. 9, pp. 1141-1152.

Jang et al., Controllable delivery of non-viral DNA from porous scaffolds, 2003, Journal of Controlled Release, vol. 86, pp. 157-168.

Japan Office Action dated Nov. 27, 2013 in corresponding Application No. 2011-529272, English translation, 4 pages.

Jiang et al., Stabilization of a Model Formalinized Protein Antigen Encapsulated in Poly(lactide-co-glycolide)- Based Microspheres, 2001, Journal of Pharmaceutical Sciences, vol. 90, No. 10, pp. 1558-1569.

Jongpaiboonkit et al., Mineral-Coated Polymer Microspheres for Controlled Protein Binding and Release, 2009, Advanced Materials,vol. 21, pp. 1960-1963.

JP 2004-530675 published Oct. 7, 2004, abstract only in English, downloaded from espacenet.com, 2 pages.

Kawachi et al., Protein Adsorption Properties of Hydrothermally Prepared Hydroxyapatite, 2008, Key Engineering Engineering Materials, vol. 361-363, pp. 71-74.

(56) References Cited

OTHER PUBLICATIONS

Kokubo et al., Ca, P-rich layer formed on high-strength bioactive glass-ceramic A-W, 1990, Journal of Biomedical Materials Research, vol. 24, No. 3, pp. 331-343.
Kurumada et al., Formation of uniform hydroxyapatite nanocoating triggered by nucleation at carboxylic groups embedded in ethylene/acrylic acid copolymer microspheres, 2008, Colloids and Surfaces A: Physiochem. Eng. Aspects, vol. 322, pp. 34-39.
Legeros, Properties of Osteoconductive Biomaterials: Calcium Phosphates, 2002, Clinical Orthopaedics and Related Research, 2002, No. 395, pp. 81-98.
Leveque et al., Promotion of Fluorapatite Crystallization by Soluble-Matrix Proteins from Lingula Anatina Shells, 2004, Angewandte Chemie International Edition, vol. 43, No. 7, pp. 885-888.
Li et al., Apatite Formation Induced by Silica Gel in a Simulated Body Fluid, 1992, Journal of the American Ceramic Society, vol. 75, No. 8, pp. 2094-2097.
Lin et al., Surface reaction of stoichiometric and calcium-deficient hydroxyapatite in simulated body fluid, 2001, Journal of Materials Science-Materials in Medicine, vol. 12, No. 8, pp. 731-741.
Lu et al., Fabrication and Bioactivity of Porous Titanium Implant, 2007, Key Engineering Materials, vols. 342-343, pp. 613-616.
Luong et al., Spatial control of protein within biomimetically nucleated mineral, 2006, Biomaterials, vol. 27, No. 7, pp. 1175-1186.
Matsumoto et al., Hydroxyapatite particles as a controlled release carrier of protein, 2004, Biomaterials, vol. 25, pp. 3807-3812.
Meng et al., W/O/W double emulsion technique using ethyl acetate as organic solvent: effects of its diffusion rate on the characteristics of microparticles, 2003, Journal of Controlled Release, vol. 91, pp. 407-416.
Miyaji et al., Bonelike apatite coating on organic polymers, Novel nucleation process using sodium silicate solution, 1999, Biomaterials, vol. 20, pp. 913-919.
Moror et al., Solvent-induced collapse of [s]ynuclein and acid-denatured cytochrome c, 2001, Protein Science, vol. 10, pp. 2195-2199.
Mu et al., Fabrication, characterization and in vitro release of paclitaxel (Taxol) loaded poly (lactic-co-glycolic acid) microspheres prepared by spray drying technique with lipid/cholesterol emulsifiers , 2001, Journal of Controlled Release, vol. 76, pp. 239-254.
Murphy et al., Growth of continuous bonelike mineral within porous poly(lactide-co-glycolide) scaffolds in vitro, 2000, Journal of Biomedical Materials Research, vol. 50, pp. 50-58.
Murphy et al., Compartmental control of mineral formation: adaptation of a biomineralization strategy for biomedical use, 2000, Polyhedron, vol. 19, pp. 357-363.
Murphy et al., Bioinspired Growth of Crystalline Carbonate Apatite on Biodegradable Polymer Substrata, 2002, Journal of the American Chemical Society, vol. 124, No. 9, pp. 1910-1917.
Murphy et al., Synthesis and in Vitro Hydroxyapatite Binding of Peptides Conjugated to Calcium-Binding Moieties , 2007, Biomacromolecules, vol. 8, pp. 2237-2243.
Newman et al., Poly(D,L lactic-co-glycolic acid) microspheres as biodegradable microcarriers for pluripotent stem cells, 2004, Biomaterials, vol. 25, pp. 5763-5771.
O'Donnell et al., Preparation of microspheres by the solvent evaporation technique, 1997, Advanced Drug Delivery Reviews, vol. 28, pp. 25-42.
Oyane et al., Preparation and assessment of revised simulated body fluids, 2003, Journal of Biomedical Materials Research Part A, vol. 65A, pp. 188-195.
Pandey et al., Nanoparticle-Based Oral Drug Delivery System for an Injectable Antibiotic—Streptomycin, 2007, Chemotherapy, vol. 53, pp. 437-441.
Pedraza et al., Osteopontin functions as an opsonin and facilitates phagocytosis by macrophages of hydroxyapatite-coated microspheres: Implications for bone wound healing, 2008, Bone, vol. 43, No. 4, pp. 708-716.
Pena et al., New method to obtain chitosan/apatite materials at room temperature, 2006, Solid State Sciences, vol. 8, No. 5, pp. 513-519.
Porjazoska et al., Poly(lactide-co-glycolide) microparticles as systems for controlled release of proteins—Preparation and characterization, 2004, Acta Pharm., vol. 54, pp. 215-229.
Qui et al., New bioactive, degradable composite microspheres as tissue engineering substrates, 2000, Journal of Biomedical Materials Research Part A, vol. 2, No. 1, pp. 66-76.
Raman et al., Modeling small-molecule release from PLG microspheres: effects of polymer degradation and nonuniform drug distribution, 2005, Journal of Controlled Release, vol. 103, No. 1, pp. 149-158.
Ruhe et al., Controlled release of rhBMP-2 loaded poly(DL-lactic-co-glycolic acid)/calcium phosphate cement composites in vivo, 2005, Journal of Controlled Release, vol. 106, pp. 162-171.
Schmaljohann, Thermo- and pH-responsive polymers in drug delivery, 2006, Advanced Drug Delivery Reviews, vol. 58, pp. 1655-1670.
Schroder et al., Hydroxyapatite chromatography: altering the phosphate-dependent elution profile of protein as a function of pH, 2003, Analytical Biochemistry, vol. 313, pp. 176-178.
Su et al., Organization of apatite crystals in human woven bone, 2003, Bone, vol. 32, pp. 150-162, vol. 32.
Tanahashi et al., Apatite Coating on Organic Polymers by a Biomimetic Process, 1994, Journal of the American Ceramic Society, vol. 77, No. 11, pp. 2805-2808.
Uchida et al., Bonelike Apatite Formation Induced on Zirconia Gel in a Simulated Body Fluid and its Modified Solutions, 2001, Journal of the American Ceramic Society, vol. 84, No. 9, pp. 2041-2044.
Urist et al., Purification of bovine bone morphogenetic protein by hydroxyapatite chromatography, 1984, Proc. Natl. Acad. Sci. USA, vol. 81, pp. 371-375.
Vaupel et al., Blood Flow, Oxygen and Nutrient Supply, and Metabolic Microenvironment of Human Tumors: A Review, 1989, Cancer Research, vol. 49, pp. 6449-6465.
Wang et al., Preparation of hollow hydroxyapatite microspheres, 2006, J Mater Sci: Mater Med. , vol. 17, pp. 641-646.
Yamaguchi et al., Enhancement of Albumin Expression in Bone Tissues With Healing Rat Fractures, 2003, Journal of Cell. Biochemistry, vol. 89, pp. 356-363.
Yamashita et al., Preparation of Apatite Thin Films through rf-Sputtering from Calcium Phosphate Glasses, 1994, Journal of the American Ceramic Society, vol. 77, No. 9, pp. 2401-2407.
Yang et al., Morphology, drug distribution, and in vitro release profiles of biodegradable polymeric microspheres containing protein fabricated by double-emulsion solvent extraction/evaporation method, 2001, Biomaterials, vol. 22, pp. 231-241.
Yokogawa et al., Growth of calcium phosphate on phosphorylated chitin fibres, 1997, Journal of Materials Science: Materials in Medicine, vol. 8, pp. 407-412.
Zhang et al., Biomimetic Polymer/Apatite Composite Scaffolds for Mineralized Tissue Engineering, 2004, Macromolecular Bioscience, 2004, vol. 4, No. 2, pp. 100-111.
Gao, Application of Fracture Mechanics Concepts to Hierarchical Biomechanics of Bone and Bone-like Materials, International Journal of Fracture, Mar. 2006, 138:101-137.
Jongpaiboonkit et al., Growth of hydroxyapatite coatings on biodegradable polymer microspheres, *ACS Appl Mater Interfaces.* 2009;1(7):1504-11.
Mohandes et al., Hydroxyapatite nanocrystals: simple preparation, characterization and formation mechanism, Mater Sci Eng C Mater Biol Appl. Dec. 2014;45:29-36.
Ono et al., Effect of Nanostructured Surface of Light Metals on Hydroxyapatite Coating, ECS Trans. 2008 vol. 11, issue 15, 1-8.
Roveri et al., Microscopic investigations of Synthetic Biomimetic Hydroxyapatite, Microscopy: Sciente, Technology, Appliaitons and Education, 2011, pp. 1868-1879.
Sahin, Synthesis and Characterization of Hydroxyapatite-Alumina-Zirconia Biocomposites, Master Thesis submitted 2006 (85 pages).

* cited by examiner

FIG. 2A-F

Scale bar = 1mm

Scale bar = 500μm

Scale bar =200μm

Scale bar = 50μm

Scale bar = 1mm

Scale bar = 500μm

Scale bar =200μm

Scale bar = 50μm

Scale bar = 20μm

Scale bar = 10μm

MINERAL COATED SCAFFOLDS

CROSS-REFERENCE TO RELATED APPLICATIONS

The present application is a: (1) U.S. Continuation-In-Part of U.S. Nonprovisional application Ser. No. 13/036,470 filed 28 Feb. 2011, now abandoned, which is a Continuation-In-Part of U.S. Nonprovisional application Ser. No. 11/927,322 filed 29 Oct. 2007, now U.S. Pat. No. 9,439,948, which claims the benefit of U.S. Provisional Application No. 60/855,235 filed 30 Oct. 2006; (2) U.S. Continuation-In-Part of U.S. National Phase application Ser. No. 13/879,178 filed 18 Feb. 2014, which is a 371 of International Application No. PCT/US09/58419 filed 25 Sep. 2009, which claims the benefit of U.S. Provisional Application No. 61/100,062 filed 25 Sep. 2008; and (3) U.S. Continuation-In-Part of U.S. Nonprovisional application Ser. No. 13/407,441 filed 28 Feb. 2012, now U.S. Pat. No. 9,433,140, which claims priority to U.S. Provisional Application No. 61/447,352 filed 28 Feb. 2011.

STATEMENT REGARDING FEDERALLY SPONSORED RESEARCH OR DEVELOPMENT

This invention was made with government support under grant R03AR052893 awarded by The National Institutes of Health. The government has certain rights in the invention.

MATERIAL INCORPORATED-BY-REFERENCE

Not Applicable.

FIELD OF THE INVENTION

The present disclosure generally relates to compositions and methods for mineral coated scaffolds.

BACKGROUND OF THE INVENTION

Hybrid materials composed of organic polymers coated with inorganic minerals have attracted much attention in biology and medicine due to their combination of advantageous properties. Polymeric materials can be a desirable base material for biomedical applications, as they can be processed into a variety of sizes and geometries, and can be designed to bioresorb in a controllable timeframe. Therefore, polymeric biomaterials have been featured in a variety of applications, including medical devices, tissue engineering scaffolds, and drug delivery systems.

Calcium phosphate based mineral coatings represent desirable surfaces for biomedical applications, as they can be similar in composition to bone tissue, and have been shown to promote favorable interactions with natural bone, a property termed "bioactivity". For example, hydroxyapatite, the major inorganic component of bone mineral, is osteoconductive (Ducheyne et al., 1999), and may also be capable of inducing new bone formation in vivo (Habibovic et al., 2006).

A particular subset of approaches used to grow hydroxyapatite coatings on biomaterials surfaces mimics some aspects of natural biomineralization processes, and has therefore been termed "biomimetic" or "bioinspired" (Hong et al., 2006; Gao and Koumoto, 2005; Leveque et al., 2004; Green et al., 2006). This type of approach is a practically and economically attractive alternative to high-temperature commercial processing methods such as plasma-spraying (Gledhill et al., 2001), sputter coating (Yamashita et al., 1994), and laser deposition (Fernandez-Pradas et al., 1998). Kokubo et al. first reported bioinspired growth of apatite coatings on bioactive CaO—$SiO_2$ glass in a simulated body fluid (SBF), which had ion concentrations nearly equal to those of human blood plasma and was held at physiologic temperature and pH (Kokubo et al., 1990). A series of subsequent studies reported mineral growth using novel formulations of SBF (Oyane et al., 2003), variation in the mineral growth process (Miyaji et al., 1999), or variations in the base materials (Yogogawa et al., 1997). The basis for mineral nucleation in these studies involved interactions of mineral ions in solution with polar functional groups on the materials surface, such as Si—OH (Li et al., 1992), Ti—OH (Barrere et al., 2004) and Zr—OH (Uchida et al., 2001). A series of recent studies has extended the bioinspired mineralization process to include formation of a bone-like hydroxyapatite coating on biodegradable polymer films (Murphy and Mooney, 2002) or porous scaffolds (Murphy et al., 2000; Zhang and Ma, 2004; Bajpai and Singh, 2007). The mechanism for mineral nucleation and growth on these materials is based on the interaction of carboxylate and hydroxyl groups on the hydrolyzed surface with calcium- and phosphate-rich nuclei in solution, creating a driving force for heterogeneous nucleation and mineral growth (Murphy and Mooney, 2002). This coating process is particularly suitable for biocompatible implants and biodegradable polymers, as it can be carried out at physiological temperature and pH (Tanahashi et al., 1994), and the mild processing conditions also suggest that it is possible to incorporate biologically active molecules such as polypeptides and polynucleotides, during the coating process.

Previous studies have shown that demineralized bone matrix (DBM) is an osteogenic material, but Ozturk et al. 2006 Int Orth. 30, 147-152, shows that DBM alone shows better osteoconductive properties than the DBM/hydroxyapatite (HA) mixture.

SUMMARY OF THE INVENTION

Among the various aspects of the present disclosure is the provision of a mineral coated scaffold that has or can include a mineral coating similar to bone.

One aspect of the present disclosure provides a method for producing a mineral coated scaffold. In some embodiments, the method includes contacting a scaffold comprising a matrix material and a modified simulated body fluid. In some embodiments, the method includes incubating the scaffold and the modified simulated body fluid for a period of time under conditions sufficient to form a mineral coated scaffold.

In some embodiments, the method includes a biodegradable matrix material. In some embodiments, the matrix material comprises polycaprolactone (PCL), polyetheretherketone (PEEK), or titanium (Ti).

In some embodiments, the method includes forming a modified simulated body fluid comprising combining NaCl, KCl, $MgCl_2$, $MgSO_4$, $NaHCO_3$, $CaCl_2$, and $KH_2PO_4$ to form the modified simulated body fluid. In some embodiments, the method includes combining NaCl at a concentration of about 100 mM to about 200 mM; KCl at a concentration of about 1 mM to about 8 mM; $MgCl_2$ at a concentration of about 0.2 mM to about 5 mM; $MgSO_4$ at a concentration of about 0.2 mM to about 5 mM; $NaHCO_3$ at a concentration of about 1 mM to about 100 mM; $CaCl_2$ at a concentration of about 2 mM to about 20 mM; and KH$_2$PO$_4$ at a concentration of about 0.5 mM to about 10 mM.

In some embodiments, the method includes forming a modified simulated body fluid that comprises combining NaCl at a concentration of about 141 mM; KCl at a concentration of about 4.0 mM; MgCl$_2$ at a concentration of about 1.0 mM; MgSO$_4$ at a concentration of about 0.5 mM; NaHCO$_3$ at a concentration of about 4.2 mM; CaCl$_2$ at a concentration of about 5 mM; and KH$_2$PO$_4$ at a concentration of about 2.0 mM.

In some embodiments, the method includes a modified simulated body fluid comprising a buffer. In some embodiments, the method includes a modified simulated body fluid comprising a buffer at a concentration of about 20 mM. In some embodiments, the method includes a modified simulated body fluid comprising a buffer selected from the group consisting of DPBS, Tris, Tris-HCl, Tris-buffered saline, or PBS.

In some embodiments, the method includes incubating the scaffold and the modified simulated body fluid for about 1 day to about 21 days. In some embodiments, the method includes incubating the scaffold and the modified simulated body fluid for about 7 days; at least about 8 days; at least about 9 days; at least about 10 days; at least about 11 days; at least about 12 days; at least about 13 days; or at least about 14 days. In some embodiments, the method includes incubating the scaffold and the modified simulated body fluid for about 5 days to about 14 days.

In some embodiments, the method includes hydrolyzing the scaffold. In some embodiments, the method includes roughening the scaffold.

In some embodiments, the method includes incubation comprising heating the modified simulated body fluid to physiologic temperature or adjusting to a physiologic pH. In some embodiments, the method includes incubating at physiologic temperature of about 37° C. or physiological pH of about 6.8.

In some embodiments, the method includes incubating comprising replacing the modified simulated body fluid, replenishing the modified simulated body fluid, removing the modified simulated body fluid, or adding the modified simulated body fluid, wherein incubating comprises maintaining a concentration of modified simulated body fluid. In some embodiments, the method includes maintaining the concentration of modified simulated body fluid comprising replacing, replenishing, removing, or adding modified simulated body fluid, NaCl, KCl, MgCl$_2$, MgSO$_4$, NaHCO$_3$, CaCl$_2$, or KH$_2$PO$_4$, or a combination thereof.

In some embodiments, the method includes the coating comprising (i) about 9% to about 100% hydroxyapatite; (ii) about 90% to about 100% hydroxyapatite; or (iii) about 97% hydroxyapatite.

In some embodiments, the method includes the coating comprising (i) about 0% to about 30% octacalcium phosphate; (ii) about 0% to about 3% octacalcium phosphate; or (iii) about 3% octacalcium phosphate.

In some embodiments, the method includes the coating comprising (i) between about 2% and about 100% porosity; or (ii) between about 20% and about 28% porosity.

In some embodiments, the method includes the coating comprising (i) between about 1 nm and about 3500 nm pore diameter; or (ii) between about 100 nm and about 350 nm pore diameter.

In some embodiments, the method includes the scaffold comprising (i) between about 200 μm and about 525 μm pore diameter; or (ii) between about 25 μm to about 65 μm pore diameter.

In some embodiments, the method includes the coating comprising (i) about 0.1 to about 18 Ca/P; or (ii) about 1.1 to about 1.76 Ca/P (calcium to phosphate ratio).

In some embodiments, the method includes the coating comprising (i) about 1.67 to about 1.76 Ca/P; (ii) about 1.1 to about 1.3 Ca/P; or (iii) about 1.37 to about 1.61 Ca/P.

In some embodiments, the method includes the coating comprising (i) about 9% to about 100% crystallinity; (ii) about 90% to about 100% crystallinity; or (iii) about 96.5% crystallinity.

In some embodiments, the method includes the coating comprising silver particles and/or demineralized bone matrix (DBM).

In some embodiments, the method includes lyophilizing the coated scaffold.

Another aspect provides a mineral coated scaffold comprising a matrix material, wherein the mineral coating of the scaffold comprises a plate-like nanostructure and a carbonate-substituted, calcium-deficient hydroxyapatite component.

Another aspect provides a mineral coated scaffold comprising a matrix material, wherein the mineral coating comprises a plate-like nanostructure and a carbonate-substituted, calcium-deficient hydroxyapatite component.

In some embodiments, the coating comprises about 9% to about 100% hydroxyapatite; about 90% to about 100% hydroxyapatite; or about 97% hydroxyapatite; about 0% to about 30% octacalcium phosphate; about 0% to about 3% octacalcium phosphate; or about 3% octacalcium phosphate; between about 2% and about 100% porosity; or between about 20% and about 28% porosity; between about 1 nm and about 3500 nm pore diameter; or between about 100 nm and about 350 nm pore diameter; about 0.1 to about 18 Ca/P; about 1.1 to about 1.76 Ca/P; about 1.67 to about 1.76 Ca/P; about 1.1 to about 1.3 Ca/P; or about 1.37 to about 1.61 Ca/P; or about 9% to about 100% crystallinity; about 90% to about 100% crystallinity; or about 96.5% crystallinity.

In some embodiments, the scaffold comprises silver particles and/or demineralized bone matrix (DBM).

In some embodiments, the scaffold exhibits improved osteoinductive properties compared to the mineral coated scaffold without the DBM.

In some embodiments, the scaffold comprises silver particles in an effective amount to provide antimicrobial, antibacterial, biostatic, or anti-infection properties.

In some embodiments the silver particles are provided as silver nanoparticles or silver microparticles.

DESCRIPTION OF THE DRAWINGS

Those of skill in the art will understand that the drawings, described below, are for illustrative purposes only. The drawings are not intended to limit the scope of the present teachings in any way.

FIG. 1A shows a representative SEM micrograph of the coating surfaces on PCL scaffold at low magnification.

FIG. 1B shows a representative SEM micrograph of the coating surfaces on PCL scaffold at high magnification.

FIG. 2A shows SEM micrographs of the coating surfaces after incubating in DPBS on day 3.

FIG. 2B shows SEM micrographs of the coating surfaces after incubating in DPBS on day 7.

FIG. 2C shows SEM micrographs of the coating surfaces after incubating in DPBS on day 14.

FIG. 2D shows SEM micrographs of the coating surfaces after incubating in Tris-HCl on day 3.

FIG. 2E shows SEM micrographs of the coating surfaces after incubating in Tris-HCl on day 7.

FIG. 2F shows SEM micrographs of the coating surfaces after incubating in Tris-HCl on day 14.

FIG. 3A shows the amount of cumulative phosphate release in Tris-HCl.

FIG. 3B shows the amount of cumulative calcium release in Tris-HCl and DPBS.

FIG. 4A shows SEM micrographs of the uncoated Ti.

FIG. 4B shows SEM micrographs of the coated Ti.

FIG. 5A shows SEM micrographs of the uncoated Ti (scale bar=1 mm).

FIG. 5B shows SEM micrographs of the uncoated Ti (scale bar=500 µm).

FIG. 6A shows SEM micrographs of the coated Ti (scale bar=1 mm).

FIG. 6B shows SEM micrographs of the coated Ti (scale bar=500 µm).

FIG. 6C shows SEM micrographs of the coated Ti (scale bar=200 µm).

FIG. 6D shows SEM micrographs of the coated Ti (scale bar=50 µm).

DETAILED DESCRIPTION OF THE INVENTION

Figure 1A:
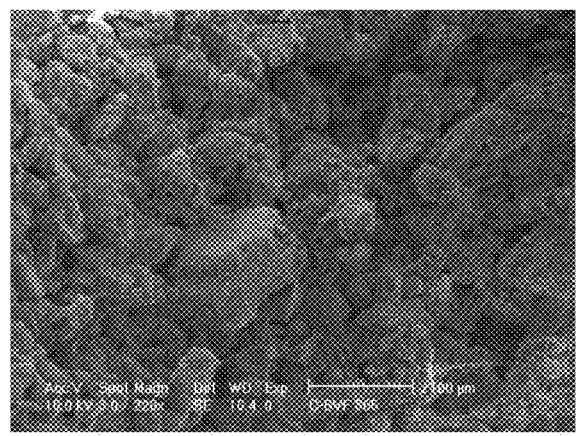
FIG. 1A-1B are a series of micrographs depicting the coating surfaces on a PCL scaffold.

The present disclosure is based, at least in part, on the discovery of advantageous properties of methods of producing mineral coated scaffolds to form a coating similar is structure and composition to bone. As shown herein, the coated scaffolds have been produced and characterized to provide advantageous properties.

Scaffold

One aspect of the present disclosure provides a scaffold suitable for mineral coating. A scaffold can provide a substrate for the growth of bone mineral. The scaffold including a simulated body fluid can promote mineral coating of the scaffold with a plate-like nanostructure and a carbonate-substituted, calcium-deficient hydroxyapatite phase. A scaffold can be as described in U.S. application Ser. Nos. 13/407,441; 13/879,178; and 13/036,470 and are incorporated herein by reference.

The scaffold can be formed of any suitable material known in the art. The selection of the scaffold material for any particular application can be made without undue experimentation. For example, an application of the scaffold can be for a medical device or an implant.

A scaffold can comprise a matrix material. As used herein, a "matrix" can be a material, e.g., a polymer, in which one or more ingredients can be suspended. A "scaffold" is understood to have a secondary or tertiary structure (e.g., a columnar structure or a porous structure in which one or more ingredients can permeate). The present disclosure is not limited to any particular matrix or scaffold. Preferably, the matrix or scaffold is biodegradable.

As described herein, a scaffold can be a hydrolyzable scaffold. For example, the scaffold can be biodegradable. As another example, the scaffold can be a polycaprolactone (PCL) scaffold or polyetheretherketone (PEEK) scaffold. As another example, the PCL scaffold can be hydrolyzed using NaOH.

As described herein, a scaffold can be coated. For example, the coating can be a mineral coating, as described herein.

A scaffold or matrix, as described herein, can include one or more components fabricated in whole or in part from a polymer material, such as a degradable polymer material, a porous polymer material, or a degradable porous polymer material. Suitable scaffold materials are discussed in, for example, Ma and Elisseeff, ed. (2005) Scaffolding in Tissue Engineering, CRC, ISBN 1574445219; Saltzman (2004) Tissue Engineering: Engineering Principles for the Design of Replacement Organs and Tissues, Oxford ISBN 019514130X.

A scaffold made in whole or in part from a polymer material can: provide structural and/or functional features of the target tissue (e.g., bone); allow cell attachment and migration; deliver and retain cells and biochemical factors; enable diffusion of cell nutrients and expressed products; or exert certain mechanical and biological influences to modify the behavior of the cell phase.

Scaffold materials can be biocompatible materials that generally form a porous, microcellular matrix, which can provide a physical support or an adhesive substrate for introducing bioactive agents or cells during fabrication, culturing, or in vivo implantation.

As described herein, a scaffold can be a metallic scaffold. As another example the metallic scaffold can be a biocompatible metallic scaffold. As another example the metallic scaffold can be a titanium (Ti) scaffold. As another example the Ti scaffold can be a Ti alloy scaffold. As another example, a Ti alloy can be Ti-35Nb-5Ta-7Zr, or TNZT.

A scaffold or matrix, as described herein, can include one or more components fabricated in whole or in part from a metallic material, such as titanium or stainless steel. Suitable metallic scaffold materials are discussed in, for example, Alvarez et al. 2009 Materials 2, 790-832.

As described herein, the metal scaffold can be treated with physical or chemical methods to impart roughness to the surface. As another example, the treatment can impart submicron- or nano-roughness to the metal surface. As another example, the metal scaffold can be treated with an alkaline solution. As another example, the alkaline solution can be NaOH or KOH. Suitable treatments for metallic scaffold materials are discussed in, for example, Alvarez et al. 2009 Materials 2, 790-832.

As described herein, the roughened titanium can have larger pore structures and smaller pore structures.

As described wherein, the larger pore structures can be at least about 200 µm. For example, the larger pore structure can be at least about 200 µm; at least about 225 µm; at least about 250 µm; at least about 275 µm; at least about 300 µm; at least about 325 µm; at least about 350 µm; at least about 375 µm; at least about 400 µm; at least about 425 µm; at least about 450 µm; at least about 475 µm; at least about 500 µm; or at least about 525 µm. It is understood that recitation of the above discrete values includes a range between each recited value.

As described wherein, the larger pore structures can be at about 200 µm; about 225 µm; about 250 µm; about 275 µm; about 300 µm; about 325 µm; about 350 µm; about 375 µm; about 400 µm; about 425 µm; about 450 µm; about 475 µm; about 500 µm; or about 525 µm. It is understood that recitation of the above discrete values includes a range between each recited value.

As described wherein, the smaller pore structures can be at least about 200 µm. For example, the smaller pore structure can be at least about 10 µm; at least about 15 µm; at least about 20 µm; at least about 25 µm; at least about 30 µm; at least about 35 µm; at least about 40 µm; at least about 45 µm; at least about 50 µm; at least about 65 µm; at least about 70 µm; at least about 75 µm; at least about 80 µm; at least about 85 µm; at least about 90 µm; at least about 95 µm; or at least about 100 µm. It is understood that recitation of the above discrete values includes a range between each recited value.

As described wherein, the smaller pore structures can be about 10 µm; about 15 µm; about 20 µm; about 25 µm; about 30 µm; about 35 µm; about 40 µm; about 45 µm; about 50 µm; about 55 µm; about 60 µm; about 65 µm; about 70 µm; about 75 µm; about 80 µm; about 85 µm; about 90 µm; about 95 µm; or about 100 µm. It is understood that recitation of the above discrete values includes a range between each recited value.

As described herein, the average pore volume can be about 10%; about 20%; about 30%; about 40%; about 50%; about 60%; about 70%; about 80%; or about 90%.

As described herein, the average surface roughness can be about 10 µm; 20 µm; 30 µm; 40 µm, 50 µm; 60 µm; 70 µm; 80 µm; 90 µm; 100 µm; 110 µm; 120 µm; 130 µm; 140 µm; 150 µm; 160 µm; 170 µm; 180 µm; 190 µm; or 200 µm. It is understood that recitation of the above discrete values includes a range between each recited value.

Generally, a biocompatible material can be one which stimulates at most only a mild, often transient, implantation response, as opposed to a severe or escalating response. A biodegradable or degradable material can be generally understood to decompose under normal in vivo physiological conditions into components which can be metabolized or excreted.

Material biodegradability can provide for absorption of the matrix by the surrounding tissues and can eliminate the necessity of a surgical removal. The rate at which degradation occurs can coincide as much as possible with the rate of mineral formation. Thus, while the mineral coating is fabricating their own natural structure around themselves, the scaffold or components thereof can provide structural integrity and eventually break down leaving the mineral which can assume the mechanical load. One or more scaffold materials can be modified so as to increase biodegradability. For example, polycaprolactone (PCL) is a biodegradable polyester by hydrolysis of its ester linkages in physiological conditions, and can be further modified with ring opening polymerization to increase its biodegradability.

In some embodiments, the scaffold comprises a negative charge, which can promote the deposition of the calcium containing material. The negative charge can be provided by any moiety present on the scaffold, for example a carboxylate group, as is present in poly(D,L-lactide-co-glycolide) (PLG).

In some embodiments, the scaffolds provided herein can be formed from polycaprolactone, a biocompatible and biodegradable polymer. However, other polymers are known to be biocompatible, and can be used for the scaffolds described herein. Nonlimiting examples of suitable biodegradable materials include polycaprolactone, polylactide, polyglycolide, poly(lactide-glycolide), poly(propylene fumarate), poly(caprolactone fumarate), polyethylene glycol, poly(glycolide-co-caprolactone), polysaccharides (e.g. alginate), chitosan, polyphosphazene, polyacrylate, polyethylene oxide-polypropylene glycol block copolymer, fibrin, collagen, fibronectin, polyvinylpyrrolidone, hyaluronic acid, polycarbonates, polyamides, polyanhydrides, polyamino acids, polyortho esters, polyacetals, polycyanoacrylates, polyurethanes, polyacrylates, ethylene-vinyl acetate polymers and other acyl substituted cellulose acetates and derivatives thereof, and analogs, mixtures, combinations and derivatives of any of the above.

In some embodiments, a scaffold, or portion or component thereof, comprises a material having a porous microstructure. Pores of a scaffold, or portion or component thereof, can mimic internal bone structure, allow adherence of cells, provide an open volume for seeding of cells, provide an open volume for growth factors or other additives, allow adherence of another matrix layer, serve as conduits for vascularization, provide internal bone features, or facilitate perfusion. A scaffold material with a high porosity and an adequate pore size is preferred so as to facilitate mineralization, cell introduction, and diffusion throughout the whole structure of both cells and nutrients.

Pores of a scaffold material can be engineered to be of various diameters. For example, the pores of a scaffold material can have a diameter range from micrometers to millimeters. As another example, the pores of the matrix material can have a diameter of about 100 µm to about 600 µm. As another example, the pores of the matrix material can have a diameter of about 150 µm, about 200 µm, about 250 µm, about 300 µm, about 350 µm, about 400 µm, about 450 µm, about 500 µm, or about 550 µm. It is understood that the pores of a scaffold material can have the same, approximately the same, or different average diameters between different components or portions of a scaffold.

A scaffold, or portion or component thereof, can be produced from proteins (e.g. extracellular matrix proteins such as fibrin, collagen, and fibronectin), polymers (e.g., polyvinylpyrrolidone), polysaccharides (e.g. alginate), hyaluronic acid, or analogs, mixtures, combinations, and derivatives of the above.

For example, a scaffold, or portion or component thereof, can be formed of synthetic polymers. Such synthetic polymers include, but are not limited to, poly(ethylene) glycol, bioerodible polymers (e.g., poly(lactide), poly(glycolic acid), poly(lactide-co-glycolide), poly(caprolactone), polyester (e.g., poly-(L-lactic acid), polyanhydride, polyglactin, polyglycolic acid), polycarbonates, polyamides, polyanhydrides, polyamino acids, polyortho esters, polyacetals, polycyanoacrylates), polyphosphazene, degradable polyurethanes, non-erodible polymers (e.g., polyacrylates, ethylene-vinyl acetate polymers and other acyl substituted cellulose acetates and derivatives thereof), non-erodible polyurethanes, polystyrenes, polyvinyl chloride, polyvinyl fluoride, polyvinyl pyrrolidone, poly(vinylimidazole), chlorosulphonated polyolifins, polyethylene oxide, polyvinyl alcohol (e.g., polyvinyl alcohol sponge), synthetic marine adhesive proteins, Teflon®, nylon, or analogs, mixtures, combinations (e.g., polyethylene oxide-polypropylene glycol block copolymer; poly(D,L-lactide-co-glycolide) fiber matrix), and derivatives of the above.

As another example, suitable scaffold materials include, for example, a collagen gel, polyvinyl alcohol, a marine adhesive protein, a PLG fiber matrix, a polyglactin fiber, a calcium alginate gel, a polyglycolic acid, polyester (e.g., poly-(L-lactic acid) or a polyanhydride), a polysaccharide (e.g. alginate), chitosan, polyphosphazene, polyacrylate, polyethylene oxide-polypropylene glycol block copolymer, fibrin, collagen, and fibronectin, polyvinylpyrrolidone, hyaluronic acid, poly(lactide), poly(glycolic acid), poly(lactide-co-glycolide), poly(caprolactone), polycarbonates, polyamides, polyanhydrides, polyamino acids, polyortho esters, polyacetals, polycyanoacrylates), polyurethanes, polyacrylates, ethylene-vinyl acetate polymers and other acyl substituted cellulose acetates and derivatives thereof), polyurethanes, polystyrenes, polyvinyl chloride, polyvinyl fluoride, poly(vinylimidazole), chlorosulphonated polyolifins, polyethylene oxide, polyvinyl alcohol, Teflon®, nylon, and analogs, mixtures, combinations and derivatives of any of the above.

As another example, a scaffold, or portion or component thereof, can be formed of naturally occurring polymers or natively derived polymers. Such polymers include, but are not limited to, agarose, alginate (e.g., calcium alginate gel), fibrin, fibrinogen, fibronectin, collagen (e.g., a collagen gel), gelatin, hyaluronic acid, chitin, and other suitable polymers and biopolymers, or analogs, mixtures, combinations, and derivatives of the above. Also, a scaffold, or portion or component thereof, can be formed from a mixture of naturally occurring biopolymers and synthetic polymers.

As another example, a scaffold can include polycarboxylates, polyanhydrides, poly(α-hydroxyesters), poly(ethylene terephthalates), poly(carbonates), poly(amides), poly(lactones), a poly(saccharides) and poly(acrylates).

A scaffold, or portion or component thereof, can comprise a crystalline or mineral component. For example, a scaffold, or portion or component thereof, can include the inorganic mineral hydroxyapatite (also known as hydroxylapatite). About seventy percent of natural bone is made up of hydroxyapatite. In some embodiments, a scaffold, or portion or component thereof, comprises a ground natural substance containing hydroxyapatite, such as bone. In some embodiments, a scaffold, or portion or component thereof, comprises substantially pure hydroxyapatite.

A scaffold, or portion or component thereof, can comprise a composite material comprising at least two components described above. As an example, a composite scaffold material can comprise at least three, at least four, at least five, at least six, at least seven, at least eight, at least nine, at least ten, or more, components. The plurality of components can be homogenously mixed throughout the scaffold, heterologously mixed throughout the scaffold, or separated into different layers of the scaffold, or a combination thereof.

In some embodiments, a scaffold, or portion or component thereof, comprises polycaprolactone, polylactide, polyglycolide, poly(lactide-glycolide), poly(propylene fumarate), poly(caprolactone fumarate), polyethylene glycol, poly(glycolide-co-caprolactone), or mixtures thereof.

For example, a scaffold, or portion or component thereof, can be formed in whole or in part of polycaprolactone or a mixture, composite, or derivative thereof. Polycaprolactone can be a particularly useful material where the scaffolds can be prepared by the methods described in U.S. Pat Pub No. 2003/0069718, U.S. Pat Pub No. 2006/0276925, U.S. Pat Pub No. 2008/0195211, U.S. Pat Pub No. 2008/0215093, or U.S. patent application Ser. No. 13/036,470, all are incorporated herein by reference in their entireties.

A scaffold, as described herein, can be any material suitable for mineral coating. For example, a scaffold can include a bead, a microsphere, a cage, or a modular scaffold. The mineral coated scaffolds can be prepared by the methods described in U.S. patent Ser. Nos. 13/407,441; 13/879,178; and 13/036,470 and are incorporated herein by reference.

Modified Simulated Body Fluid

A modified simulated body fluid as described herein can be a solution including ionic constituents of blood plasma. In some embodiments, the modified simulated body fluid does not comprise organic components. Inorganic minerals suitable for producing a calcium-containing mineral coating include various bone mineral ions, such as, but not limited to calcium and phosphate and combinations of bone mineral ions, such as calcium-phosphates. A modified simulated body fluid can be as described in U.S. application Ser. Nos. 13/407,441; 13/879,178; and 13/036,470 and are incorporated by reference.

A modified simulated body fluid as described herein can be used to mineral coat a scaffold. For example, the scaffold can be immersed and incubated in a modified simulated body fluid. As another example, the modified simulated body fluid can be replaced, replenished, or removed and added at least about once a day; at least about twice per day; or at least about three times per day. As another example, the modified simulated body fluid can be replaced at least about once every day; at least about once every two days; at least once every three days; at least once every four days; at least once every five days; at least once every six days; or at least once every seven days.

As described herein, a modified simulated body fluid can be a solution of ionic constituents of blood plasma, with double the concentrations of calcium and phosphate ions.

As described herein, a modified simulated body fluid can be a solution comprising NaCl, KCl, $MgCl_2$, $MgSO_4$, $NaHCO_3$, $CaCl_2$, and $KH_2PO_4$.

A modified simulated body fluid can include at least about 1 mM NaCl. For example, a modified simulated body fluid can include at least about 1 mM NaCl; at least about 10 mM NaCl; at least about 20 mM NaCl; at least about 30 mM NaCl; at least about 40 mM NaCl; at least about 50 mM NaCl; at least about 60 mM NaCl; at least about 70 mM NaCl; at least about 80 mM NaCl; at least about 90 mM NaCl; at least about 100 mM NaCl; at least about 110 mM NaCl; at least about 120 mM NaCl; at least about 130 mM NaCl; at least about 140 mM NaCl; at least about 150 mM NaCl; at least about 160 mM NaCl; at least about 170 mM NaCl; at least about 180 mM NaCl; at least about 190 mM NaCl; at least about 200 mM NaCl; at least about 300 mM NaCl; at least about 400 mM NaCl; at least about 500 mM NaCl; at least about 600 mM NaCl; at least about 700 mM NaCl; at least about 800 mM NaCl; at least about 900 mM NaCl; at least about 1000 mM NaCl; at least about 1100 mM NaCl; at least about 1200 mM NaCl; at least about 1300 mM NaCl; at least about 1400 mM NaCl; at least about 1500 mM NaCl; at least about 1600 mM NaCl; at least about 1700 mM NaCl; at least about 1800 mM NaCl; at least about 1900 mM NaCl; or at least about 2000 mM NaCl. It is understood that recitation of the above discrete values includes a range between each recited value.

As another example, a modified simulated body fluid can include about 1 mM NaCl, about 10 mM NaCl; about 20 mM NaCl; about 30 mM NaCl; about 40 mM NaCl; about 50 mM NaCl; about 60 mM NaCl; about 70 mM NaCl; about 80 mM NaCl; about 90 mM NaCl; about 100 mM NaCl; about 110 mM NaCl; about 120 mM NaCl; about 130 mM NaCl; about 140 mM NaCl; about 150 mM NaCl; about 160 mM NaCl; about 170 mM NaCl; about 180 mM NaCl; about 190 mM NaCl; about 200 mM NaCl; about 300 mM NaCl; about 400 mM NaCl; about 500 mM NaCl; about 600 mM NaCl; about 700 mM NaCl; about 800 mM NaCl; about 900 mM NaCl; about 1000 mM NaCl; about 1100 mM NaCl; about 1200 mM NaCl; about 1300 mM NaCl; about 1400 mM NaCl; about 1500 mM NaCl; about 1600 mM NaCl; about 1700 mM NaCl; about 1800 mM NaCl; about 1900 mM NaCl; or about 2000 mM NaCl. It is understood that recitation of the above discrete values includes a range between each recited value.

A modified simulated body fluid can include at least about 0.4 mM KCl. For example, a modified simulated body fluid can include at least about 0.4 mM KCl; at least about 1 mM KCl; at least about 2 mM KCl; at least about 3 mM KCl; at least about 4 mM KCl; at least about 5 mM KCl; at least about 6 mM KCl; at least about 7 mM KCl; at least about 8 mM KCl; at least about 9 mM KCl; at least about 10 mM KCl; at least about 11 mM KCl; at least about 12 mM KCl; at least about 13 mM KCl; at least about 14 mM KCl; at least about 15 mM KCl; at least about 16 mM KCl; at least about 17 mM KCl; at least about 18 mM KCl; at least about 19 mM KCl; at least about 20 mM KCl; at least about 21 mM KCl; at least about 22 mM KCl; at least about 23 mM KCl; at least about 24 mM KCl; at least about 25 mM KCl; at least about 26 mM KCl; at least about 27 mM KCl; at least about 28 mM KCl; at least about 29 mM KCl; at least about 30 mM KCl; at least about 31 mM KCl; at least about 32 mM KCl; at least about 33 mM KCl; at least about 34 mM KCl; at least about 35 mM KCl; at least about 36 mM KCl; at least about 37 mM KCl; at least about 38 mM KCl; at least about 39 mM KCl; at least about 40 mM KCl; at least about 41 mM KCl; at least about 42 mM KCl; at least about 43 mM KCl; at least about 44 mM KCl; at least about 45 mM KCl; at least about 46 mM KCl; at least about 47 mM KCl; at least about 48 mM KCl; at least about 49 mM KCl; at least about 50 mM KCl; at least about 51 mM KCl; at least about 52 mM KCl; at least about 53 mM KCl; at least about 54 mM KCl; at least about 55 mM KCl; at least about 56 mM KCl; at least about 57 mM KCl; at least about 58 mM KCl; at least about 59 mM KCl; at least about 60 mM KCl; at least about 61 mM KCl; at least about 62 mM KCl; at least about 63 mM KCl; at least about 64 mM KCl; at least about 65 mM KCl; at least about 66 mM KCl; at least about 67 mM KCl; at least about 68 mM KCl; at least about 69 mM KCl; at least about 70 mM KCl; at least about 71 mM KCl; at least about 72 mM KCl; at least about 73 mM KCl; at least about 74 mM KCl; at least about 75 mM KCl; at least about 76 mM KCl; at least about 77 mM KCl; at least about 78 mM KCl; at least about 79 mM KCl; or at least about 80 mM KCl. It is understood that recitation of the above discrete values includes a range between each recited value.

As another example, a modified simulated body fluid can include about 0.4 mM KCl; about 1 mM KCl; about 2 mM KCl; about 3 mM KCl; about 4 mM KCl; about 5 mM KCl; about 6 mM KCl; about 7 mM KCl; about 8 mM KCl; about 9 mM KCl; about 10 mM KCl; about 11 mM KCl; about 12 mM KCl; about 13 mM KCl; about 14 mM KCl; about 15 mM KCl; about 16 mM KCl; about 17 mM KCl; about 18 mM KCl; about 19 mM KCl; about 20 mM KCl; about 21 mM KCl; about 22 mM KCl; about 23 mM KCl; about 24 mM KCl; about 25 mM KCl; about 26 mM KCl; about 27 mM KCl; about 28 mM KCl; about 29 mM KCl; about 30 mM KCl; about 31 mM KCl; about 32 mM KCl; about 33 mM KCl; about 34 mM KCl; about 35 mM KCl; about 36 mM KCl; about 37 mM KCl; about 38 mM KCl; about 39 mM KCl; about 40 mM; about 41 mM KCl; about 42 mM KCl; about 43 mM KCl; about 44 mM KCl; about 45 mM KCl; about 46 mM KCl; about 47 mM KCl; about 48 mM KCl; about 49 mM KCl; about 50 mM KCl; about 51 mM KCl; about 52 mM KCl; about 53 mM KCl; about 54 mM KCl; about 55 mM KCl; about 56 mM KCl; about 57 mM KCl; about 58 mM KCl; about 59 mM KCl; about 60 mM KCl; about 61 mM KCl; about 62 mM KCl; about 63 mM KCl; about 64 mM KCl; about 65 mM KCl; about 66 mM KCl; about 67 mM KCl; about 68 mM KCl; about 69 mM KCl; about 70 mM KCl; about 71 mM KCl; about 72 mM KCl; about 73 mM KCl; about 74 mM KCl; about 75 mM KCl; about 76 mM KCl; about 77 mM KCl; about 78 mM KCl; about 79 mM KCl; or about 80 mM KCl. It is understood that recitation of the above discrete values includes a range between each recited value.

A modified simulated body fluid can include at least about 0.1 mM $MgCl_2$. For example, a modified simulated body fluid can include at least about 0.1 mM $MgCl_2$; at least about 0.25 mM $MgCl_2$; at least about 0.5 mM $MgCl_2$; at least about 1 mM $MgCl_2$; at least about 1.25 mM $MgCl_2$; at least about 1.5 mM $MgCl_2$; at least about 1.75 mM $MgCl_2$; at least about 2 mM $MgCl_2$; at least about 2.25 mM $MgCl_2$; at least about 2.5 mM $MgCl_2$; at least about 2.75 mM $MgCl_2$; at least about 3 mM $MgCl_2$; at least about 3.25 mM $MgCl_2$; at least about 3.5 mM $MgCl_2$; at least about 3.75 mM $MgCl_2$; at least about 4 mM $MgCl_2$; at least about 4.25 mM $MgCl_2$; at least about 4.5 mM $MgCl_2$; at least about 4.75 mM $MgCl_2$; at least about 5 mM $MgCl_2$; at least about 5.25 mM $MgCl_2$; at least about 5.5 mM $MgCl_2$; at least about 5.75 mM $MgCl_2$; at least about 6 mM $MgCl_2$; at least about 6.25 mM $MgCl_2$; at least about 6.5 mM $MgCl_2$; at least about 6.75 mM $MgCl_2$; at least about 7 mM $MgCl_2$; at least about 7.25 mM $MgCl_2$; at least about 7.5 mM $MgCl_2$; at least about 7.75 mM $MgCl_2$; at least about 8 mM $MgCl_2$; at least about 8.25 mM $MgCl_2$; at least about 8.5 mM $MgCl_2$; at least about 8.75 mM $MgCl_2$; at least about 9 mM $MgCl_2$; at least about 9.25 mM $MgCl_2$; at least about 9.5 mM $MgCl_2$; at least about 9.75 mM $MgCl_2$; at least about 10 mM $MgCl_2$; at least about 11 mM $MgCl_2$; at least about 12 mM $MgCl_2$; at least about 13 mM $MgCl_2$; at least about 14 mM $MgCl_2$; at least about 15 mM $MgCl_2$; at least about 16 mM $MgCl_2$; at least about 17 mM $MgCl_2$; at least about 18 mM $MgCl_2$; at least about 19 mM $MgCl_2$; at least about 20 mM $MgCl_2$; at least about 21 mM $MgCl_2$; at least about 22 mM $MgCl_2$; at least about 23 mM $MgCl_2$; at least about 24 mM $MgCl_2$; at least about 25 mM $MgCl_2$; at least about 26 mM $MgCl_2$; at least about 27 mM $MgCl_2$; at least about 28 mM $MgCl_2$; at least about 29 mM $MgCl_2$; at least about 30 mM $MgCl_2$; at least about 31 mM $MgCl_2$; at least about 32 mM $MgCl_2$; at least about 33 mM $MgCl_2$; at least about 34 mM $MgCl_2$; at least about 35 mM $MgCl_2$; at least about 36 mM $MgCl_2$; at least about 37 mM $MgCl_2$; at least about 38 mM $MgCl_2$; at least about 39 mM $MgCl_2$; at least about 40 mM $MgCl_2$; at least about 41 mM $MgCl_2$; at least about 42 mM $MgCl_2$; at least about 43 mM $MgCl_2$; at least about 44 mM $MgCl_2$; at least about 45 mM $MgCl_2$; at least about 46 mM $MgCl_2$; at least about 47 mM $MgCl_2$; at least about 48 mM $MgCl_2$; at least about 49 mM $MgCl_2$; or at least about 50 mM $MgCl_2$. It is understood that recitation of the above discrete values includes a range between each recited value.

As another example, a modified simulated body fluid can include about 0.1 mM $MgCl_2$; at least about 0.25 mM $MgCl_2$; about 0.5 mM $MgCl_2$; about 1 mM $MgCl_2$; about 1.25 mM $MgCl_2$; about 1.5 mM $MgCl_2$; about 1.75 mM $MgCl_2$; about 2 mM $MgCl_2$; about 2.25 mM $MgCl_2$; about 2.5 mM $MgCl_2$; about 2.75 mM $MgCl_2$; about 3 mM $MgCl_2$; about 3.25 mM $MgCl_2$; about 3.5 mM $MgCl_2$; about 3.75 mM $MgCl_2$; about 4 mM $MgCl_2$; about 4.25 mM $MgCl_2$; about 4.5 mM $MgCl_2$; about 4.75 mM $MgCl_2$; about 5 mM $MgCl_2$; about 5.25 mM $MgCl_2$; about 5.5 mM $MgCl_2$; about 5.75 mM $MgCl_2$; about 6 mM $MgCl_2$; about 6.25 mM $MgCl_2$; about 6.5 mM $MgCl_2$; about 6.75 mM $MgCl_2$; about 7 mM $MgCl_2$; about 7.25 mM $MgCl_2$; about 7.5 mM $MgCl_2$; about 7.75 mM $MgCl_2$; about 8 mM $MgCl_2$; about 8.25 mM $MgCl_2$; about 8.5 mM $MgCl_2$; about 8.75 mM $MgCl_2$; about 9 mM $MgCl_2$; about 9.25 mM $MgCl_2$; about 9.5 mM $MgCl_2$; about 9.75 mM $MgCl_2$; about 10 mM $MgCl_2$; about 11 mM $MgCl_2$; about 12 mM $MgCl_2$; about 13 mM $MgCl_2$; about 14 mM $MgCl_2$; about 15 mM $MgCl_2$; about 16 mM $MgCl_2$; about 17 mM $MgCl_2$; about 18 mM $MgCl_2$; about 19 mM $MgCl_2$; about 20 mM $MgCl_2$; about 21 mM $MgCl_2$; about 22 mM $MgCl_2$; about 23 mM $MgCl_2$; about 24 mM $MgCl_2$; about 25 mM $MgCl_2$; about 26 mM $MgCl_2$; about 27 mM $MgCl_2$; about 28 mM $MgCl_2$; about 29 mM $MgCl_2$; about 30 mM $MgCl_2$; about 31 mM $MgCl_2$; about 32 mM $MgCl_2$; about 33 mM $MgCl_2$; about 34 mM $MgCl_2$; about 35 mM $MgCl_2$; about 36 mM $MgCl_2$; about 37 mM $MgCl_2$; about 38 mM $MgCl_2$; about 39 mM $MgCl_2$; about 40 mM $MgCl_2$; about 41 mM $MgCl_2$; about 42 mM $MgCl_2$; about 43 mM $MgCl_2$; about 44 mM $MgCl_2$; about 45 mM $MgCl_2$; about 46 mM $MgCl_2$; about 47 mM $MgCl_2$; about 48 mM $MgCl_2$; about 49 mM $MgCl_2$; or about 50 mM $MgCl_2$. It is understood that recitation of the above discrete values includes a range between each recited value.

A modified simulated body fluid can include at least about 0.05 mM $MgSO_4$. For example, a modified simulated body fluid can include at least about 0.05 mM $MgSO_4$; at least about 0.25 mM $MgSO_4$; at least about 0.5 mM $MgSO_4$; at least about 0.75 mM $MgSO_4$; at least about 1 mM $MgSO_4$; at least about 1.25 mM $MgSO_4$; at least about 1.5 mM $MgSO_4$; at least about 1.75 mM $MgSO_4$; at least about 2 mM $MgSO_4$; at least about 2.25 mM $MgSO_4$; at least about 2.5 mM $MgSO_4$; at least about 2.75 mM $MgSO_4$; at least about 3 mM $MgSO_4$; at least about 3.25 mM $MgSO_4$; at least about 3.5 mM $MgSO_4$; at least about 4 mM $MgSO_4$; at least about 4.25 mM $MgSO_4$; at least about 4.5 mM $MgSO_4$; at least about 4.75 mM $MgSO_4$; at least about 5 mM $MgSO_4$; at least about 6 mM $MgSO_4$; at least about 7 mM $MgSO_4$; at least about 8 mM $MgSO_4$; at least about 9 mM $MgSO_4$; at least about 10 mM $MgSO_4$; at least about 11 mM $MgSO_4$; at least about 12 mM $MgSO_4$; at least about 13 mM $MgSO_4$; at least about 14 mM $MgSO_4$; at least about 15 mM $MgSO_4$; at least about 16 mM $MgSO_4$; at least about 17 mM $MgSO_4$; at least about 18 mM $MgSO_4$; at least about 19 mM $MgSO_4$; at least about 20 mM $MgSO_4$; at least about 21 mM $MgSO_4$; at least about 22 mM $MgSO_4$; at least about 23 mM $MgSO_4$; at least about 24 mM $MgSO_4$; at least about 25 mM $MgSO_4$; at least about 26 mM $MgSO_4$; at least about 27 mM $MgSO_4$; at least about 28 mM $MgSO_4$; at least about 29 mM $MgSO_4$; at least about 30 mM $MgSO_4$; at least about 31 mM $MgSO_4$; at least about 32 mM $MgSO_4$; at least about 33 mM $MgSO_4$; at least about 34 mM $MgSO_4$; at least about 35 mM $MgSO_4$; at least about 36 mM $MgSO_4$; at least about 37 mM $MgSO_4$; at least about 38 mM $MgSO_4$; at least about 39 mM $MgSO_4$; at least about 40 mM $MgSO_4$; at least about 41 mM $MgSO_4$; at least about 42 mM $MgSO_4$; at least about 43 mM $MgSO_4$; at least about 44 mM $MgSO_4$; at least about 45 mM $MgSO_4$; at least about 46 mM $MgSO_4$; at least about 47 mM $MgSO_4$; at least about 48 mM $MgSO_4$; at least about 49 mM $MgSO_4$; or at least about 50 mM $MgSO_4$. It is understood that recitation of the above discrete values includes a range between each recited value.

As another example, a modified simulated body fluid can include about 0.05 mM $MgSO_4$; about 0.25 mM $MgSO_4$; about 0.5 mM $MgSO_4$; about 0.75 mM $MgSO_4$; about 1 mM $MgSO_4$; about 1.25 mM $MgSO_4$; about 1.5 mM $MgSO_4$; about 1.75 mM $MgSO_4$; about 2 mM $MgSO_4$; about 2.25 mM $MgSO_4$; about 2.5 mM $MgSO_4$; about 2.75 mM $MgSO_4$; about 3 mM $MgSO_4$; about 3.25 mM $MgSO_4$; about 3.5 mM $MgSO_4$; about 4 mM $MgSO_4$; about 4.25 mM $MgSO_4$; about 4.5 mM $MgSO_4$; about 4.75 mM $MgSO_4$; about 5 mM $MgSO_4$; about 6 mM $MgSO_4$; about 7 mM $MgSO_4$; about 8 mM $MgSO_4$; about 9 mM $MgSO_4$; about 10 mM $MgSO_4$; about 11 mM $MgSO_4$; about 12 mM $MgSO_4$; about 13 mM $MgSO_4$; about 14 mM $MgSO_4$; about 15 mM $MgSO_4$; about 16 mM $MgSO_4$; about 17 mM $MgSO_4$; about 18 mM $MgSO_4$; about 19 mM $MgSO_4$; about 20 mM $MgSO_4$; about 21 mM $MgSO_4$; about 22 mM $MgSO_4$; about 23 mM $MgSO_4$; about 24 mM $MgSO_4$; about 25 mM $MgSO_4$; about 26 mM $MgSO_4$; about 27 mM $MgSO_4$; about 28 mM $MgSO_4$; about 29 mM $MgSO_4$; about 30 mM $MgSO_4$; about 31 mM $MgSO_4$; about 32 mM $MgSO_4$; about 33 mM $MgSO_4$; about 34 mM $MgSO_4$; about 35 mM $MgSO_4$; about 36 mM $MgSO_4$; about 37 mM $MgSO_4$; about 38 mM $MgSO_4$; about 39 mM $MgSO_4$; about 40 mM $MgSO_4$; about 41 mM $MgSO_4$; about 42 mM $MgSO_4$; about 43 mM $MgSO_4$; about 44 mM $MgSO_4$; about 45 mM $MgSO_4$; about 46 mM $MgSO_4$; about 47 mM $MgSO_4$; about 48 mM $MgSO_4$; about 49 mM $MgSO_4$; or about 50 mM $MgSO_4$. It is understood that recitation of the above discrete values includes a range between each recited value.

A modified simulated body fluid can include at least about 0.4 mM $NaHCO_3$. For example, a modified simulated body fluid can include at least about 0.4 mM $NaHCO_3$; at least about 0.6 mM $NaHCO_3$; at least about 0.8 mM $NaHCO_3$; at least about 1.0 mM $NaHCO_3$; at least about 1.2 mM $NaHCO_3$; at least about 1.4 mM $NaHCO_3$; at least about 1.6 mM $NaHCO_3$; at least about 1.8 mM $NaHCO_3$; at least about 2.0 mM $NaHCO_3$; at least about 2.2 mM $NaHCO_3$; at least about 2.4 mM $NaHCO_3$; at least about 2.6 mM $NaHCO_3$; at least about 2.8 mM $NaHCO_3$; at least about 3.0 mM $NaHCO_3$; at least about 3.2 mM $NaHCO_3$; at least about 3.4 mM $NaHCO_3$; at least about 3.6 mM $NaHCO_3$; at least about 3.8 mM $NaHCO_3$; at least about 4.0 mM $NaHCO_3$; at least about 4.2 mM $NaHCO_3$; at least about 4.4 mM $NaHCO_3$; at least about 4.6 mM $NaHCO_3$; at least about 4.8 mM $NaHCO_3$; at least about 5.0 mM $NaHCO_3$; at least about 5.2 mM $NaHCO_3$; at least about 5.4 mM $NaHCO_3$; at least about 5.6 mM $NaHCO_3$; at least about 5.8 mM $NaHCO_3$; at least about 6.0 mM $NaHCO_3$; at least about 6.2 mM $NaHCO_3$; at least about 6.4 mM $NaHCO_3$; at least about 6.6 mM $NaHCO_3$; at least about 6.8 mM $NaHCO_3$; at least about 7.0 mM $NaHCO_3$; at least about 7.2 mM $NaHCO_3$; at least about 7.4 mM $NaHCO_3$; at least about 7.6 mM $NaHCO_3$; at least about 7.8 mM $NaHCO_3$; at least about 8.0 mM $NaHCO_3$; at least about 8.2 mM $NaHCO_3$; at least about 8.4 mM $NaHCO_3$; at least about 8.6 mM $NaHCO_3$; at least about 8.8 mM $NaHCO_3$; at least about 9.0 mM $NaHCO_3$; at least about 10 mM $NaHCO_3$; at least about 20 mM $NaHCO_3$; at least about 30 mM $NaHCO_3$; at least about 40 mM $NaHCO_3$; at least about 50 mM NaHCO$_3$; at least about 60 mM NaHCO$_3$; at least about 70 mM NaHCO$_3$; at least about 80 mM NaHCO$_3$; at least about 90 mM NaHCO$_3$; at least about 100 mM NaHCO$_3$; at least about 200 mM NaHCO$_3$; at least about 300 mM NaHCO$_3$; at least about 400 mM NaHCO$_3$; at least about 500 mM NaHCO$_3$; at least about 600 mM NaHCO$_3$; at least about 700 mM NaHCO$_3$; at least about 800 mM NaHCO$_3$; at least about 900 mM NaHCO$_3$; or at least about 1000 mM NaHCO$_3$.

As another example, a modified simulated body fluid can include about 0.4 mM NaHCO$_3$; about 0.6 mM NaHCO$_3$; about 0.8 mM NaHCO$_3$; about 1.0 mM NaHCO$_3$; about 1.2 mM NaHCO$_3$; about 1.4 mM NaHCO$_3$; about 1.6 mM NaHCO$_3$; about 1.8 mM NaHCO$_3$; about 2.0 mM NaHCO$_3$; about 2.2 mM NaHCO$_3$; about 2.4 mM NaHCO$_3$; about 2.6 mM NaHCO$_3$; about 2.8 mM NaHCO$_3$; about 3.0 mM NaHCO$_3$; about 3.2 mM NaHCO$_3$; about 3.4 mM NaHCO$_3$; about 3.6 mM NaHCO$_3$; about 3.8 mM NaHCO$_3$; about 4.0 mM NaHCO$_3$; about 4.2 mM NaHCO$_3$; about 4.4 mM NaHCO$_3$; about 4.6 mM NaHCO$_3$; about 4.8 mM NaHCO$_3$; about 5.0 mM NaHCO$_3$; about 5.2 mM NaHCO$_3$; about 5.4 mM NaHCO$_3$; about 5.6 mM NaHCO$_3$; about 5.8 mM NaHCO$_3$; about 6.0 mM NaHCO$_3$; about 6.2 mM NaHCO$_3$; about 6.4 mM NaHCO$_3$; about 6.6 mM NaHCO$_3$; about 6.8 mM NaHCO$_3$; about 7.0 mM NaHCO$_3$; about 7.2 mM NaHCO$_3$; about 7.4 mM NaHCO$_3$; about 7.6 mM NaHCO$_3$; about 7.8 mM NaHCO$_3$; about 8.0 mM NaHCO$_3$; about 8.2 mM NaHCO$_3$; about 8.4 mM NaHCO$_3$; about 8.6 mM NaHCO$_3$; about 8.8 mM NaHCO$_3$; about 9.0 mM NaHCO$_3$; about 10 mM NaHCO$_3$; about 20 mM NaHCO$_3$; about 30 mM NaHCO$_3$; about 40 mM NaHCO$_3$; about 50 mM NaHCO$_3$; about 60 mM NaHCO$_3$; about 70 mM NaHCO$_3$; about 80 mM NaHCO$_3$; about 90 mM NaHCO$_3$; about 100 mM NaHCO$_3$; about 200 mM NaHCO$_3$; about 300 mM NaHCO$_3$; about 400 mM NaHCO$_3$; about 500 mM NaHCO$_3$; about 600 mM NaHCO$_3$; about 700 mM NaHCO$_3$; about 800 mM NaHCO$_3$; about 900 mM NaHCO$_3$; or about 1000 mM NaHCO$_3$. It is understood that recitation of the above discrete values includes a range between each recited value.

A modified simulated body fluid can include at least about 0.5 mM CaCl$_2$. For example, a modified simulated body fluid can include at least about 0.5 mM CaCl$_2$; at least about 1.0 mM CaCl$_2$; at least about 1.5 mM CaCl$_2$; at least about 2.0 mM CaCl$_2$; at least about 2.5 mM CaCl$_2$; at least about 3.0 mM CaCl$_2$; at least about 3.5 mM CaCl$_2$; at least about 4.0 mM CaCl$_2$; at least about 4.5 mM CaCl$_2$; at least about 5.0 mM CaCl$_2$; at least about 5.5 mM CaCl$_2$; at least about 6.0 mM CaCl$_2$; at least about 6.5 mM CaCl$_2$; at least about 7.0 mM CaCl$_2$; at least about 7.5 mM CaCl$_2$; at least about 8.0 mM CaCl$_2$; at least about 8.5 mM CaCl$_2$; at least about 9.0 mM CaCl$_2$; at least about 9.5 mM CaCl$_2$; at least about 10.0 mM CaCl$_2$; at least about 10.5 mM CaCl$_2$; at least about 11.0 mM CaCl$_2$; at least about 11.5 mM CaCl$_2$; at least about 12.0 mM CaCl$_2$; at least about 12.5 mM CaCl$_2$; at least about 13.0 mM CaCl$_2$; at least about 13.5 mM CaCl$_2$; at least about 14.0 mM CaCl$_2$; at least about 14.5 mM CaCl$_2$; at least about 15.0 mM CaCl$_2$; at least about 15.5 mM CaCl$_2$; at least about 16.0 mM CaCl$_2$; at least about 16.5 mM CaCl$_2$; at least about 17.0 mM CaCl$_2$; at least about 17.5 mM CaCl$_2$; at least about 18.0 mM CaCl$_2$; at least about 18.5 mM CaCl$_2$; at least about 19.0 mM CaCl$_2$; at least about 19.5 mM CaCl$_2$; at least about 20.0 mM CaCl$_2$; at least about 25 mM CaCl$_2$; at least about 30 mM CaCl$_2$; at least about 35 mM CaCl$_2$; at least about 40 mM CaCl$_2$; at least about 45 mM CaCl$_2$; or at least about 50 mM CaCl$_2$. It is understood that recitation of the above discrete values includes a range between each recited value.

As another example, a modified simulated body fluid can include about 0.5 mM CaCl$_2$; about 1.0 mM CaCl$_2$; about 1.5 mM CaCl$_2$; about 2.0 mM CaCl$_2$; about 2.5 mM CaCl$_2$; about 3.0 mM CaCl$_2$; about 3.5 mM CaCl$_2$; about 4.0 mM CaCl$_2$; about 4.5 mM CaCl$_2$; about 5.0 mM CaCl$_2$; about 5.5 mM CaCl$_2$; about 6.0 mM CaCl$_2$; about 6.5 mM CaCl$_2$; about 7.0 mM CaCl$_2$; about 7.5 mM CaCl$_2$; about 8.0 mM CaCl$_2$; about 8.5 mM CaCl$_2$; about 9.0 mM CaCl$_2$; about 9.5 mM CaCl$_2$; about 10.0 mM CaCl$_2$; about 10.5 mM CaCl$_2$; about 11.0 mM CaCl$_2$; about 11.5 mM CaCl$_2$; about 12.0 mM CaCl$_2$; about 12.5 mM CaCl$_2$; about 13.0 mM CaCl$_2$; about 13.5 mM CaCl$_2$; about 14.0 mM CaCl$_2$; about 14.5 mM CaCl$_2$; about 15.0 mM CaCl$_2$; about 15.5 mM CaCl$_2$; about 16.0 mM CaCl$_2$; about 16.5 mM CaCl$_2$; about 17.0 mM CaCl$_2$; about 17.5 mM CaCl$_2$; about 18.0 mM CaCl$_2$; about 18.5 mM CaCl$_2$; about 19.0 mM CaCl$_2$; about 19.5 mM CaCl$_2$; about 20.0 mM CaCl$_2$; about 25 mM CaCl$_2$; about 30 mM CaCl$_2$; about 35 mM CaCl$_2$; about 40 mM CaCl$_2$; about 45 mM CaCl$_2$; or about 50 mM CaCl$_2$. It is understood that recitation of the above discrete values includes a range between each recited value.

A modified simulated body fluid can include at least about 0.2 mM KH$_2$PO$_4$. For example, a modified simulated body fluid can include at least about 0.2 mM KH$_2$PO$_4$; at least about 0.4 mM KH$_2$PO$_4$; at least about 0.6 mM KH$_2$PO$_4$; at least about 0.8 mM KH$_2$PO$_4$; at least about 1.0 mM KH$_2$PO$_4$; at least about 1.2 mM KH$_2$PO$_4$; at least about 1.4 mM KH$_2$PO$_4$; at least about 1.6 mM KH$_2$PO$_4$; at least about 1.8 mM KH$_2$PO$_4$; at least about 2.0 mM KH$_2$PO$_4$; at least about 2.2 mM KH$_2$PO$_4$; at least about 2.4 mM KH$_2$PO$_4$; at least about 2.6 mM KH$_2$PO$_4$; at least about 2.8 mM KH$_2$PO$_4$; at least about 3.0 mM KH$_2$PO$_4$; at least about 3.2 mM KH$_2$PO$_4$; at least about 3.4 mM KH$_2$PO$_4$; at least about 3.6 mM KH$_2$PO$_4$; at least about 3.8 mM KH$_2$PO$_4$; at least about 4.0 mM KH$_2$PO$_4$; at least about 4.2 mM KH$_2$PO$_4$; at least about 4.4 mM KH$_2$PO$_4$; at least about 4.6 mM KH$_2$PO$_4$; at least about 4.8 mM KH$_2$PO$_4$; at least about 5.0 mM KH$_2$PO$_4$; at least about 5.2 mM KH$_2$PO$_4$; at least about 5.4 mM KH$_2$PO$_4$; at least about 5.6 mM KH$_2$PO$_4$; at least about 5.8 mM KH$_2$PO$_4$; at least about 6.0 mM KH$_2$PO$_4$; at least about 6.2 mM KH$_2$PO$_4$; at least about 6.4 mM KH$_2$PO$_4$; at least about 6.8 mM KH$_2$PO$_4$; at least about 7.0 mM KH$_2$PO$_4$; at least about 7.2 mM KH$_2$PO$_4$; at least about 7.4 mM KH$_2$PO$_4$; at least about 7.6 mM KH$_2$PO$_4$; at least about 7.8 mM KH$_2$PO$_4$; at least about 8.0 mM KH$_2$PO$_4$; at least about 8.2 mM KH$_2$PO$_4$; at least about 8.4 mM KH$_2$PO$_4$; at least about 8.6 mM KH$_2$PO$_4$; at least about 8.8 mM KH$_2$PO$_4$; at least about 9.0 mM KH$_2$PO$_4$; at least about 9.2 mM KH$_2$PO$_4$; at least about 9.4 mM KH$_2$PO$_4$; at least about 9.6 mM KH$_2$PO$_4$; at least about 9.8 mM KH$_2$PO$_4$; at least about 10.0 mM KH$_2$PO$_4$; at least about 20 mM KH$_2$PO$_4$; at least about 30 mM KH$_2$PO$_4$; at least about 40 mM KH$_2$PO$_4$; at least about 50 mM KH$_2$PO$_4$; at least about 60 mM KH$_2$PO$_4$; at least about 70 mM KH$_2$PO$_4$; at least about 80 mM KH$_2$PO$_4$; at least about 90 mM KH$_2$PO$_4$; at least about 100 mM KH$_2$PO$_4$; at least about 110 mM KH$_2$PO$_4$; at least about 120 mM KH$_2$PO$_4$; at least about 130 mM KH$_2$PO$_4$; at least about 140 mM KH$_2$PO$_4$; at least about 150 mM KH$_2$PO$_4$; at least about 160 mM KH$_2$PO$_4$; at least about 170 mM KH$_2$PO$_4$; at least about 180 mM KH$_2$PO$_4$; at least about 190 mM KH$_2$PO$_4$; or at least about 200 mM KH$_2$PO$_4$. It is understood that recitation of the above discrete values includes a range between each recited value.

As another example, a modified simulated body fluid can include about 0.2 mM KH$_2$PO$_4$; about 0.4 mM KH$_2$PO$_4$;

about 0.6 mM $KH_2PO_4$; about 0.8 mM $KH_2PO_4$; about 1.0 mM $KH_2PO_4$; about 1.2 mM $KH_2PO_4$; about 1.4 mM $KH_2PO_4$; about 1.6 mM $KH_2PO_4$; about 1.8 mM $KH_2PO_4$; about 2.0 mM $KH_2PO_4$; about 2.2 mM $KH_2PO_4$; about 2.4 mM $KH_2PO_4$; about 2.6 mM $KH_2PO_4$; about 2.8 mM $KH_2PO_4$; about 3.0 mM $KH_2PO_4$; about 3.2 mM $KH_2PO_4$; about 3.4 mM $KH_2PO_4$; about 3.6 mM $KH_2PO_4$; about 3.8 mM $KH_2PO_4$; about 4.0 mM $KH_2PO_4$; about 4.2 mM $KH_2PO_4$; about 4.4 mM $KH_2PO_4$; about 4.6 mM $KH_2PO_4$; about 4.8 mM $KH_2PO_4$; about 5.0 mM $KH_2PO_4$; about 5.2 mM $KH_2PO_4$; about 5.4 mM $KH_2PO_4$; about 5.6 mM $KH_2PO_4$; about 5.8 mM $KH_2PO_4$; about 6.0 mM $KH_2PO_4$; about 6.2 mM $KH_2PO_4$; about 6.4 mM $KH_2PO_4$; about 6.8 mM $KH_2PO_4$; about 7.0 mM $KH_2PO_4$; about 7.2 mM $KH_2PO_4$; about 7.4 mM $KH_2PO_4$; about 7.6 mM $KH_2PO_4$; about 7.8 mM $KH_2PO_4$; about 8.0 mM $KH_2PO_4$; about 8.2 mM $KH_2PO_4$; about 8.4 mM $KH_2PO_4$; about 8.6 mM $KH_2PO_4$; about 8.8 mM $KH_2PO_4$; about 9.0 mM $KH_2PO_4$; about 9.2 mM $KH_2PO_4$; about 9.4 mM $KH_2PO_4$; about 9.6 mM $KH_2PO_4$; about 9.8 mM $KH_2PO_4$; about 10.0 mM $KH_2PO_4$; about 20 mM $KH_2PO_4$; about 30 mM $KH_2PO_4$; about 40 mM $KH_2PO_4$; about 50 mM $KH_2PO_4$; about 60 mM $KH_2PO_4$; about 70 mM $KH_2PO_4$; about 80 mM $KH_2PO_4$; about 90 mM $KH_2PO_4$; about 100 mM $KH_2PO_4$; about 110 mM $KH_2PO_4$; about 120 mM $KH_2PO_4$; about 130 mM $KH_2PO_4$; about 140 mM $KH_2PO_4$; about 150 mM $KH_2PO_4$; about 160 mM $KH_2PO_4$; about 170 mM $KH_2PO_4$; about 180 mM $KH_2PO_4$; about 190 mM $KH_2PO_4$; or about 200 mM $KH_2PO_4$. It is understood that recitation of the above discrete values includes a range between each recited value.

In some embodiments, the solution can comprise a surfactant, which can change the morphology of the calcium-containing mineral layer. Any surfactant now known or later discovered may be used here. In some embodiments, the surfactant can be Tween 20™.

Mineral Coating

A scaffold, or portion or component thereof, described herein can include a surface modification or a coating. The mineral coating of a scaffold, as described herein, can be performed by any conventional manner. A mineral coating can be as described in U.S. application Ser. Nos. 13/407,441; 13/879,178; and 13/036,470 and are incorporated by reference.

The Examples describe exemplary methods for producing coated scaffolds using a mineral coating solution. For example, the mineral coating solution can be a modified simulated body fluid (mSBF). By adjusting the mineral composition, and/or concentration of the mSBF, the composition of the mineral precipitated on the scaffolds can be manipulated. See also U.S. Patent Application Publication US 2008/0095817 A1; U.S. Pat. No. 6,767,928 B1; U.S. Pat. No. 6,541,022 B1; PCT Publication WO 2008/070355 A2; PCT Publication WO 2008/082766 A2; Murphy and Mooney, 2001; Murphy and Messersmith, 2000.

As described herein, the mineral coating can be calcium-containing. For example the calcium-containing mineral coating can include hydroxyapatite (HAP), α-tricalcium phosphate (α-TCP), β-tricalcium phosphate (β-TCP), amorphous calcium phosphate, dicalcium phosphate, octacalcium phosphate, calcium phosphate (CaP), or calcium carbonate. The calcium-containing mineral coating can comprise a plurality of layers, e.g., separate layers having distinct dissolution profiles. Under physiological conditions, solubility of calcium phosphate species can adhere to the following trend: amorphous calcium phosphate>dicalcium phosphate>octacalcium phosphate>β-TCP>HAP. A dicalcium phosphate mineral can have a dissolution rate that is more than fifty times higher than that of HAP. Therefore, creation of a matrix with distinct calcium phosphate layers allows for a broad range of dissolution patterns.

For example, a mineral coating can be according to ISO 2337 'Implants for surgery-In vitro evaluation for apatite-forming ability of implant materials'. As another example, mineral coating can be an adapted protocol according to ISO 2337 'Implants for surgery-In vitro evaluation for apatite-forming ability of implant materials'. As another example, the mineral coating can be performed by immersing a scaffold into a modified simulated body fluid at physiological conditions and continuous rotations. Continuous rotations can be replenishing the modified simulated body fluid, replacing the modified simulated body fluid, or removing and adding modified simulated body fluid.

As described herein, the scaffold can be incubated in modified simulated body fluid (mSBF) solutions to induce formation of a calcium phosphate-based mineral layer for mineral nucleation and growth. The mSBF solution can contain ionic constituents of blood plasma, with double the concentrations of calcium and phosphate ions, held at physiologic temperature and pH. The growth of calcium phosphate-based minerals, specifically bone-like minerals, on bioresorbable polymer matrices using mSBF incubation has been demonstrated (Lin et al., 2004; Murphy et al., 2002, 2005).

As described herein, a mineral coating of a scaffold, as described herein, can be performed by incubating a scaffold. For example, the mineral coating, described herein, can be developed by incubating the constituents in modified simulated body fluid (mSBF), for five days or more at a pH of about 6.8 to about 7.4 and at a temperature of about 37° C. The SBF or mSBF can be refreshed daily. Using the chemical composition described in the Examples, the procedure produces a calcium-deficient, carbonate-containing apatite material on alginate and on poly-(α-hydroxy esters). See U.S. Pat. No. 6,767,928, incorporated herein by reference. mSBF can include elevated calcium and phosphate. In general, an increase in pH favors hydroxyapatite growth, while a decrease in pH favors octacalcium phosphate mineral growth.

As another example, conditions favorable for hydroxyapatite formation can include a pH between about 5.0 and about 8.0 and a calcium concentration multiplied by a phosphate concentration between about 10-5 and about 10-8 M. Likewise, conditions favorable for octacalcium phosphate formation include a pH between about 6.0 and about 8.0 and a calcium concentration multiplied by a phosphate concentration between about 10-5 and about 10-7.5 M. Furthermore, conditions favorable for dicalcium phosphate dehydrate formation can include a pH between about 6.0 and about 8.0 and a calcium concentration multiplied by a phosphate concentration between about 10-4 and about 10-6 M.

As another example, one could vary the pH of mSBF between about 5.0 and about 6.0 to promote hydroxyapatite formation. Similarly, one could vary the pH of mSBF between about 6.0 and about 6.5 to promote octacalcium phosphate and hydroxyapatite formation. Likewise, one could vary the pH of mSBF between about 6.5 and about 8.0 to promote dicalcium phosphate, octacalcium phosphate, and hydroxyapatite formation.

As another example, the scaffold can be incubated for at least about 1 day; at least about 2 days; at least about 3 days; at least about 4 days; at least about 5 days; at least about 6 days; at least about 7 days; at least about 8 days; at least about 9 days; at least about 10 days; at least about 11 days; at least about 12 days; at least about 13 days; at least about 14 days; at least about 15 days; at least about 16 days; at least about 17 days; at least about 18 days; at least about 19 days; at least about 20 days; at least about 21 days; at least about 22 days; at least about 23 days; at least about 24 days; at least about 25 days; at least about 26 days; at least about 27 days; at least about 28 days; at least about 29 days; or at least about 30 days. It is understood that recitation of the above discrete values includes a range between each recited value.

For example, the scaffold can be incubated for about 1 day; about 2 days; about 3 days; about 4 days; about 5 days; about 6 days; about 7 days; about 8 days; about 9 days; about 10 days; about 11 days; about 12 days; about 13 days; about 14 days; about 15 days; about 16 days; about 17 days; about 18 days; about 19 days; about 20 days; about 21 days; about 22 days; about 23 days; about 24 days; about 25 days; about 26 days; about 27 days; about 28 days; about 29 days; or about 30 days. It is understood that recitation of the above discrete values includes a range between each recited value.

A mineral coating of a scaffold, as described herein, can be performed by incubating a scaffold at a temperature. For example, the scaffold can be incubated at a physiologically relevant temperature. As another example, the scaffold can be incubated at a temperature of about 1° C.; about 2° C.; about 3° C.; about 4° C.; about 5° C.; about 6° C.; about 7° C.; about 8° C.; about 9° C.; about 10° C.; about 11° C.; about 12° C.; about 13° C.; about 14° C.; about 15° C.; about 16° C.; about 17° C.; about 18° C.; about 19° C.; about 20° C.; about 21° C.; about 22° C.; about 23° C.; about 24° C.; about 25° C.; about 26° C.; about 27° C.; about 28° C.; about 29° C.; about 30° C.; about 31° C.; about 32° C.; about 33° C.; about 34° C.; about 35° C.; about 36° C.; about 37° C.; about 38° C.; about 39° C.; about 40° C.; about 41° C.; about 42° C.; about 43° C.; about 44° C.; about 45° C.; about 46° C.; about 47° C.; about 48° C.; about 49° C.; about 50° C.; about 51° C.; about 52° C.; about 53° C.; about 54° C.; about 55° C.; about 56° C.; about 57° C.; about 58° C.; about 59° C.; about 60° C.; about 61° C.; about 62° C.; about 63° C.; about 64° C.; about 65° C.; about 66° C.; about 67° C.; about 68° C.; about 69° C.; about 70° C.; about 71° C.; about 72° C.; about 73° C.; about 74° C.; about 75° C.; about 76° C.; about 77° C.; about 78° C.; about 79° C.; about 80° C.; about 81° C.; about 82° C.; about 83° C.; about 84° C.; about 85° C.; about 86° C.; about 87° C.; about 88° C.; about 89° C.; about 90° C.; about 91° C.; about 92° C.; about 93° C.; about 94° C.; about 95° C.; about 96° C.; about 97° C.; about 98° C.; about 99° C.; or about 100° C.

A scaffold, or portion or component thereof, can be coated individually or in groups using, for example, a CaP coating technology. A scaffold, or portion or component thereof, can be modified individually or in groups using a technique such as aminolysis for RGD attachment, chemical conjugation, layer by layer deposition, or chemical vapor deposition.

Prior to deposition of the first calcium-containing mineral, the scaffold may be surface-functionalized to allow increased mineral deposition by utilizing chemical pretreatment to achieve surface hydrolysis (e.g., using an NaOH solution). Surface degradation by this technique can cause an increase in the amount of polar oxygen functional groups on the surface of the material.

The functionalized surface can then be incubated in a mineral-containing solution (e.g., modified simulated body fluid). The mineral coating process, as described herein, can mimic natural biomineralization processes.

The mineral coating, as described herein, can be similar in structure and composition to human bone mineral. For example, the mineral coating can include spherical clusters with a plate-like structure or a plate-like structure and a carbonate-substituted, calcium deficient hydroxyapatite phase composition. As another example, the coating can be an osteoconductive mineral coating.

As another example, the mineral coating can include an apatite. Apatite can include calcium phosphate, calcium carbonate, calcium fluoride, calcium hydroxide, or citrate.

As another example, a mineral coating can comprises a plurality of discrete mineral islands on the scaffold, or the mineral coating can be formed on the entire surface of the scaffold. As another example, the mineral coating can comprise a substantially homogeneous mineral coating. In other embodiments, the mineral coatings can be any suitable coating material containing calcium and phosphate, such as hydroxyapatite, calcium-deficient carbonate-containing hydroxyapatite, tricalcium phosphate, amorphous calcium phosphate, octacalcium phosphate, dicalcium phosphate, calcium phosphate, or a mixture thereof. For example, an osteoconductive mineral coating can be calcium-deficient carbonate-containing hydroxyapatite.

As another example, the mineral coating can include hydroxyapatite. Calcium deficient hydroxyapatite can have a formula of $Ca_{10-x}(PO_4)_{6-x}(HPO_4)_x(OH)_{2-x}$. Stoichiometric hydroxyapatite can have a chemical formula of $Ca_{10}(PO_4)_6(OH)_2$ or can be also written as $Ca_5(PO_4)_3(OH)$. Hydroxyapatite can be predominantly crystalline, but may be present in amorphous forms.

The mineral coating, as described herein, can include at least about 1% hydroxyapatite. For example, the mineral coating can include at least about 1% hydroxyapatite; at least about 2% hydroxyapatite; at least about 3% hydroxyapatite; at least about 4% hydroxyapatite; at least about 5% hydroxyapatite; at least about 6% hydroxyapatite; at least about 7% hydroxyapatite; at least about 8% hydroxyapatite; at least about 9% hydroxyapatite; at least about 10% hydroxyapatite; at least about 11% hydroxyapatite; at least about 12% hydroxyapatite; at least about 13% hydroxyapatite; at least about 14% hydroxyapatite; at least about 15% hydroxyapatite; at least about 16% hydroxyapatite; at least about 17% hydroxyapatite; at least about 18% hydroxyapatite; at least about 19% hydroxyapatite; at least about 20% hydroxyapatite; at least about 21% hydroxyapatite; at least about 22% hydroxyapatite; at least about 23% hydroxyapatite; at least about 24% hydroxyapatite; at least about 25% hydroxyapatite; at least about 26% hydroxyapatite; at least about 27% hydroxyapatite; at least about 28% hydroxyapatite; at least about 29% hydroxyapatite; at least about 30% hydroxyapatite; at least about 31% hydroxyapatite; at least about 32% hydroxyapatite; at least about 33% hydroxyapatite; at least about 34% hydroxyapatite; at least about 35% hydroxyapatite; at least about 36% hydroxyapatite; at least about 37% hydroxyapatite; at least about 38% hydroxyapatite; at least about 39% hydroxyapatite; at least about 40% hydroxyapatite; at least about 41% hydroxyapatite; at least about 42% hydroxyapatite; at least about 43% hydroxyapatite; at least about 44% hydroxyapatite; at least about 45% hydroxyapatite; at least about 46% hydroxyapatite; at least about 47% hydroxyapatite; at least about 48% hydroxyapatite; at least about 49% hydroxyapatite; at least about 50% hydroxyapatite; at least about 51% hydroxyapatite; at least about 52% hydroxyapatite; at least about 53% hydroxyapatite; at least about 54% hydroxyapatite; at least about 55% hydroxyapatite; at least about 56% hydroxyapatite; at least about 57% hydroxyapatite; at least about 58% hydroxyapatite; at least about 59% hydroxyapatite; at least about 60% hydroxyapatite; at least about 61% hydroxyapatite; at least about 62% hydroxyapatite; at least about 63% hydroxyapatite; at least about 64% hydroxyapatite; at least about 65% hydroxyapatite; at least about 66% hydroxyapatite; at least about 67% hydroxyapatite; at least about 68% hydroxyapatite; at least about 69% hydroxyapatite; at least about 70% hydroxyapatite; at least about 71% hydroxyapatite; at least about 72% hydroxyapatite; at least about 73% hydroxyapatite; at least about 74% hydroxyapatite; at least about 75% hydroxyapatite; at least about 76% hydroxyapatite; at least about 77% hydroxyapatite; at least about 78% hydroxyapatite; at least about 79% hydroxyapatite; at least about 80% hydroxyapatite; at least about 81% hydroxyapatite; at least about 82% hydroxyapatite; at least about 83% hydroxyapatite; at least about 84% hydroxyapatite; at least about 85% hydroxyapatite; at least about 86% hydroxyapatite; at least about 87% hydroxyapatite; at least about 88% hydroxyapatite; at least about 89% hydroxyapatite; at least about 90% hydroxyapatite; at least about 91% hydroxyapatite; at least about 92% hydroxyapatite; at least about 93% hydroxyapatite; at least about 94% hydroxyapatite; at least about 95% hydroxyapatite; at least about 96% hydroxyapatite; at least about 97% hydroxyapatite; at least about 98% hydroxyapatite; at least about 99% hydroxyapatite; or at least about 100% hydroxyapatite. It is understood that recitation of the above discrete values includes a range between each recited value.

As another example, the mineral coating can include about 1% hydroxyapatite; about 2% hydroxyapatite; about 3% hydroxyapatite; about 4% hydroxyapatite; about 5% hydroxyapatite; about 6% hydroxyapatite; about 7% hydroxyapatite; about 8% hydroxyapatite; about 9% hydroxyapatite; about 10% hydroxyapatite; about 11% hydroxyapatite; about 12% hydroxyapatite; about 13% hydroxyapatite; about 14% hydroxyapatite; about 15% hydroxyapatite; about 16% hydroxyapatite; about 17% hydroxyapatite; about 18% hydroxyapatite; about 19% hydroxyapatite; about 20% hydroxyapatite; about 21% hydroxyapatite; about 22% hydroxyapatite; about 23% hydroxyapatite; about 24% hydroxyapatite; about 25% hydroxyapatite; about 26% hydroxyapatite; about 27% hydroxyapatite; about 28% hydroxyapatite; about 29% hydroxyapatite; about 30% hydroxyapatite; about 31% hydroxyapatite; about 32% hydroxyapatite; about 33% hydroxyapatite; about 34% hydroxyapatite; about 35% hydroxyapatite; about 36% hydroxyapatite; about 37% hydroxyapatite; about 38% hydroxyapatite; about 39% hydroxyapatite; about 40% hydroxyapatite; about 41% hydroxyapatite; about 42% hydroxyapatite; about 43% hydroxyapatite; about 44% hydroxyapatite; about 45% hydroxyapatite; about 46% hydroxyapatite; about 47% hydroxyapatite; about 48% hydroxyapatite; about 49% hydroxyapatite; about 50% hydroxyapatite; about 51% hydroxyapatite; about 52% hydroxyapatite; about 53% hydroxyapatite; about 54% hydroxyapatite; about 55% hydroxyapatite; about 56% hydroxyapatite; about 57% hydroxyapatite; about 58% hydroxyapatite; about 59% hydroxyapatite; about 60% hydroxyapatite; about 61% hydroxyapatite; about 62% hydroxyapatite; about 63% hydroxyapatite; about 64% hydroxyapatite; about 65% hydroxyapatite; about 66% hydroxyapatite; about 67% hydroxyapatite; about 68% hydroxyapatite; about 69% hydroxyapatite; about 70% hydroxyapatite; about 71% hydroxyapatite; about 72% hydroxyapatite; about 73% hydroxyapatite; about 74% hydroxyapatite; about 75% hydroxyapatite; about 76% hydroxyapatite; about 77% hydroxyapatite; about 78% hydroxyapatite; about 79% hydroxyapatite; about 80% hydroxyapatite; about 81% hydroxyapatite; about 82% hydroxyapatite; about 83% hydroxyapatite; about 84% hydroxyapatite; about 85% hydroxyapatite; about 86% hydroxyapatite; about 87% hydroxyapatite; about 88% hydroxyapatite; about 89% hydroxyapatite; about 90% hydroxyapatite; about 91% hydroxyapatite; about 92% hydroxyapatite; about 93% hydroxyapatite; about 94% hydroxyapatite; about 95% hydroxyapatite; about 96% hydroxyapatite; about 97% hydroxyapatite; about 98% hydroxyapatite; about 99% hydroxyapatite; or about 100% hydroxyapatite. It is understood that recitation of the above discrete values includes a range between each recited value.

The mineral coating, as described herein, can include octacalcium phosphate. Octacalcium phosphate has a chemical formula of $Ca_8H_2(PO_4)_6 \cdot 5H_2O$ or can also be written as $Ca_4HO_{12}P_3$. Octacalcium phosphate has been shown to be a precursor of hydroxyapatite. Hydrolysis of Octacalcium phosphate can create hydroxyapatite. Octacalcium phosphate can be predominantly crystalline, but may be present in amorphous forms.

The mineral coating, as described herein, can include at least about 1% octacalcium phosphate. For example, the mineral coating can include at least about 1% octacalcium phosphate; at least about 2% octacalcium phosphate; at least about 3% octacalcium phosphate; at least about 4% octacalcium phosphate; at least about 5% octacalcium phosphate; at least about 6% octacalcium phosphate; at least about 7% octacalcium phosphate; at least about 8% octacalcium phosphate; at least about 9% octacalcium phosphate; at least about 10% octacalcium phosphate; at least about 11% octacalcium phosphate; at least about 12% octacalcium phosphate; at least about 13% octacalcium phosphate; at least about 14% octacalcium phosphate; at least about 15% octacalcium phosphate; at least about 16% octacalcium phosphate; at least about 17% octacalcium phosphate; at least about 18% octacalcium phosphate; at least about 19% octacalcium phosphate; at least about 20% octacalcium phosphate; at least about 21% octacalcium phosphate; at least about 22% octacalcium phosphate; at least about 23% octacalcium phosphate; at least about 24% octacalcium phosphate; at least about 25% octacalcium phosphate; at least about 26% octacalcium phosphate; at least about 27% octacalcium phosphate; at least about 28% octacalcium phosphate; at least about 29% octacalcium phosphate; at least about 30% octacalcium phosphate; at least about 31% octacalcium phosphate; at least about 32% octacalcium phosphate; at least about 33% octacalcium phosphate; at least about 34% octacalcium phosphate; at least about 35% octacalcium phosphate; at least about 36% octacalcium phosphate; at least about 37% octacalcium phosphate; at least about 38% octacalcium phosphate; at least about 39% octacalcium phosphate; at least about 40% octacalcium phosphate; at least about 41% octacalcium phosphate; at least about 42% octacalcium phosphate; at least about 43% octacalcium phosphate; at least about 44% octacalcium phosphate; at least about 45% octacalcium phosphate; at least about 46% octacalcium phosphate; at least about 47% octacalcium phosphate; at least about 48% octacalcium phosphate; at least about 49% octacalcium phosphate; at least about 50% octacalcium phosphate; at least about 51% octacalcium phosphate; at least about 52% octacalcium phosphate; at least about 53% octacalcium phosphate; at least about 54% octacalcium phosphate; at least about 55% octacalcium phosphate; at least about 56% octacalcium phosphate; at least about 57% octacalcium phosphate; at least about 58% octacalcium phosphate; at least about 59% octacalcium phosphate; at least about 60% octacalcium phosphate; at least about 61% octacalcium phosphate; at least about 62% octacalcium phosphate; at least about 63% octacalcium phosphate; at least about 64% octacalcium phosphate; at least about 65% octacalcium phosphate; at least about 66% octacalcium phosphate; at least about 67% octacalcium phosphate; at least about 68% octacalcium phosphate; at least about 69% octacalcium phosphate; at least about 70% octacalcium phosphate; at least about 71% octacalcium phosphate; at least about 72% octacalcium phosphate; at least about 73% octacalcium phosphate; at least about 74% octacalcium phosphate; at least about 75% octacalcium phosphate; at least about 76% octacalcium phosphate; at least about 77% octacalcium phosphate; at least about 78% octacalcium phosphate; at least about 79% octacalcium phosphate; at least about 80% octacalcium phosphate; at least about 81% octacalcium phosphate; at least about 82% octacalcium phosphate; at least about 83% octacalcium phosphate; at least about 84% octacalcium phosphate; at least about 85% octacalcium phosphate; at least about 86% octacalcium phosphate; at least about 87% octacalcium phosphate; at least about 88% octacalcium phosphate; at least about 89% octacalcium phosphate; at least about 90% octacalcium phosphate; at least about 91% octacalcium phosphate; at least about 92% octacalcium phosphate; at least about 93% octacalcium phosphate; at least about 94% octacalcium phosphate; at least about 95% octacalcium phosphate; at least about 96% octacalcium phosphate; at least about 97% octacalcium phosphate; at least about 98% octacalcium phosphate; at least about 99% octacalcium phosphate; or at least about 100% octacalcium phosphate. It is understood that recitation of the above discrete values includes a range between each recited value.

As another example, the mineral coating can include about 1% octacalcium phosphate; about 2% octacalcium phosphate; about 3% octacalcium phosphate; about 4% octacalcium phosphate; about 5% octacalcium phosphate; about 6% octacalcium phosphate; about 7% octacalcium phosphate; about 8% octacalcium phosphate; about 9% octacalcium phosphate; about 10% octacalcium phosphate; about 11% octacalcium phosphate; about 12% octacalcium phosphate; about 13% octacalcium phosphate; about 14% octacalcium phosphate; about 15% octacalcium phosphate; about 16% octacalcium phosphate; about 17% octacalcium phosphate; about 18% octacalcium phosphate; about 19% octacalcium phosphate; about 20% octacalcium phosphate; about 21% octacalcium phosphate; about 22% octacalcium phosphate; about 23% octacalcium phosphate; about 24% octacalcium phosphate; about 25% octacalcium phosphate; about 26% octacalcium phosphate; about 27% octacalcium phosphate; about 28% octacalcium phosphate; about 29% octacalcium phosphate; about 30% octacalcium phosphate; about 31% octacalcium phosphate; about 32% octacalcium phosphate; about 33% octacalcium phosphate; about 34% octacalcium phosphate; about 35% octacalcium phosphate; about 36% octacalcium phosphate; about 37% octacalcium phosphate; about 38% octacalcium phosphate; about 39% octacalcium phosphate; about 40% octacalcium phosphate; about 41% octacalcium phosphate; about 42% octacalcium phosphate; about 43% octacalcium phosphate; about 44% octacalcium phosphate; about 45% octacalcium phosphate; about 46% octacalcium phosphate; about 47% octacalcium phosphate; about 48% octacalcium phosphate; about 49% octacalcium phosphate; about 50% octacalcium phosphate; about 51% octacalcium phosphate; about 52% octacalcium phosphate; about 53% octacalcium phosphate; about 54% octacalcium phosphate; about 55% octacalcium phosphate; about 56% octacalcium phosphate; about 57% octacalcium phosphate; about 58% octacalcium phosphate; about 59% octacalcium phosphate; about 60% octacalcium phosphate; about 61% octacalcium phosphate; about 62% octacalcium phosphate; about 63% octacalcium phosphate; about 64% octacalcium phosphate; about 65% octacalcium phosphate; about 66% octacalcium phosphate; about 67% octacalcium phosphate; about 68% octacalcium phosphate; about 69% octacalcium phosphate; about 70% octacalcium phosphate; about 71% octacalcium phosphate; about 72% octacalcium phosphate; about 73% octacalcium phosphate; about 74% octacalcium phosphate; about 75% octacalcium phosphate; about 76% octacalcium phosphate; about 77% octacalcium phosphate; about 78% octacalcium phosphate; about 79% octacalcium phosphate; about 80% octacalcium phosphate; about 81% octacalcium phosphate; about 82% octacalcium phosphate; about 83% octacalcium phosphate; about 84% octacalcium phosphate; about 85% octacalcium phosphate; about 86% octacalcium phosphate; about 87% octacalcium phosphate; about 88% octacalcium phosphate; about 89% octacalcium phosphate; about 90% octacalcium phosphate; about 91% octacalcium phosphate; about 92% octacalcium phosphate; about 93% octacalcium phosphate; about 94% octacalcium phosphate; about 95% octacalcium phosphate; about 96% octacalcium phosphate; about 97% octacalcium phosphate; about 98% octacalcium phosphate; about 99% octacalcium phosphate; or about 100% octacalcium phosphate. It is understood that recitation of the above discrete values includes a range between each recited value.

The mineral coating, as described herein, can include at least about 1% porosity. For example, the mineral coating, as described herein, can include a porosity of at least about 1% porosity; at least about 2% porosity; at least about 3% porosity; at least about 4% porosity; at least about 5% porosity; at least about 6% porosity; at least about 7% porosity; at least about 8% porosity; at least about 9% porosity; at least about 10% porosity; at least about 11% porosity; at least about 12% porosity; at least about 13% porosity; at least about 14% porosity; at least about 15% porosity; at least about 16% porosity; at least about 17% porosity; at least about 18% porosity; at least about 19% porosity; at least about 20% porosity; at least about 21% porosity; at least about 22% porosity; at least about 23% porosity; at least about 24% porosity; at least about 25% porosity; at least about 26% porosity; at least about 27% porosity; at least about 28% porosity; at least about 29% porosity; at least about 30% porosity; at least about 31% porosity; at least about 32% porosity; at least about 33% porosity; at least about 34% porosity; at least about 35% porosity; at least about 36% porosity; at least about 37% porosity; at least about 38% porosity; at least about 39% porosity; at least about 40% porosity; at least about 41% porosity; at least about 42% porosity; at least about 43% porosity; at least about 44% porosity; at least about 45% porosity; at least about 46% porosity; at least about 47% porosity; at least about 48% porosity; at least about 49% porosity; at least about 50% porosity; at least about 51% porosity; at least about 52% porosity; at least about 53% porosity; at least about 54% porosity; at least about 55% porosity; at least about 56% porosity; at least about 57% porosity; at least about 58% porosity; at least about 59% porosity; at least about 60% porosity; at least about 61% porosity; at least about 62% porosity; at least about 63% porosity; at least about 64% porosity; at least about 65% porosity; at least about 66% porosity; at least about 67% porosity; at least about 68% porosity; at least about 69% porosity; at least about 70% porosity; at least about 71% porosity; at least about 72% porosity; at least about 73% porosity; at least about 74% porosity; at least about 75% porosity; at least about 76% porosity; at least about 77% porosity; at least about 78% porosity; at least about 79% porosity; at least about 80% porosity; at least about 81% porosity; at least about 82% porosity; at least about 83% porosity; at least about 84% porosity; at least about 85% porosity; at least about 86% porosity; at least about 87% porosity; at least about 88% porosity; at least about 89% porosity; at least about 90% porosity; at least about 91% porosity; at least about 92% porosity; at least about 93% porosity; at least about 94% porosity; at least about 95% porosity; at least about 96% porosity; at least about 97% porosity; at least about 98% porosity; at least about 99% porosity; or at least about 100% porosity. It is understood that recitation of the above discrete values includes a range between each recited value.

As another example, the mineral coating can include about 1% porosity; about 2% porosity; about 3% porosity; about 4% porosity; about 5% porosity; about 6% porosity; about 7% porosity; about 8% porosity; about 9% porosity; about 10% porosity; about 11% porosity; about 12% porosity; about 13% porosity; about 14% porosity; about 15% porosity; about 16% porosity; about 17% porosity; about 18% porosity; about 19% porosity; about 20% porosity; about 21% porosity; about 22% porosity; about 23% porosity; about 24% porosity; about 25% porosity; about 26% porosity; about 27% porosity; about 28% porosity; about 29% porosity; about 30% porosity; about 31% porosity; about 32% porosity; about 33% porosity; about 34% porosity; about 35% porosity; about 36% porosity; about 37% porosity; about 38% porosity; about 39% porosity; about 40% porosity; about 41% porosity; about 42% porosity; about 43% porosity; about 44% porosity; about 45% porosity; about 46% porosity; about 47% porosity; about 48% porosity; about 49% porosity; about 50% porosity; about 51% porosity; about 52% porosity; about 53% porosity; about 54% porosity; about 55% porosity; about 56% porosity; about 57% porosity; about 58% porosity; about 59% porosity; about 60% porosity; about 61% porosity; about 62% porosity; about 63% porosity; about 64% porosity; about 65% porosity; about 66% porosity; about 67% porosity; about 68% porosity; about 69% porosity; about 70% porosity; about 71% porosity; about 72% porosity; about 73% porosity; about 74% porosity; about 75% porosity; about 76% porosity; about 77% porosity; about 78% porosity; about 79% porosity; about 80% porosity; about 81% porosity; about 82% porosity; about 83% porosity; about 84% porosity; about 85% porosity; about 86% porosity; about 87% porosity; about 88% porosity; about 89% porosity; about 90% porosity; about 91% porosity; about 92% porosity; about 93% porosity; about 94% porosity; about 95% porosity; about 96% porosity; about 97% porosity; about 98% porosity; about 99% porosity; or about 100% porosity. It is understood that recitation of the above discrete values includes a range between each recited value.

The mineral coating, as described herein, can include a pore diameter between about 1 nm and about 3500 nm. As another example, the mineral coating, as described herein, can include a pore diameter between about 100 and about 350 nm. As another example, the mineral coating, as described herein, can include at least about 1 nm pore diameter; at least about 10 nm pore diameter; at least about 20 nm pore diameter; at least about 30 nm pore diameter; at least about 40 nm pore diameter; at least about 50 nm pore diameter; at least about 55 nm pore diameter; at least about 60 nm pore diameter; at least about 65 nm pore diameter; at least about 70 nm pore diameter; at least about 75 nm pore diameter; at least about 80 nm pore diameter; at least about 85 nm pore diameter; at least about 90 nm pore diameter; at least about 95 nm pore diameter; at least about 100 nm pore diameter; at least about 105 nm pore diameter; at least about 110 nm pore diameter; at least about 115 nm pore diameter; at least about 120 nm pore diameter; at least about 125 nm pore diameter; at least about 130 nm pore diameter; at least about 140 nm pore diameter; at least about 145 nm pore diameter; at least about 150 nm pore diameter; at least about 155 nm pore diameter; at least about 160 nm pore diameter; at least about 165 nm pore diameter; at least about 170 nm pore diameter; at least about 175 nm pore diameter; at least about 180 nm pore diameter; at least about 185 nm pore diameter; at least about 190 nm pore diameter; at least about 200 nm pore diameter; at least about 205 nm pore diameter; at least about 210 nm pore diameter; at least about 215 nm pore diameter; at least about 220 nm pore diameter; at least about 225 nm pore diameter; at least about 230 nm pore diameter; at least about 235 nm pore diameter; at least about 240 nm pore diameter; at least about 245 nm pore diameter; at least about 250 nm pore diameter; at least about 255 nm pore diameter; at least about 260 nm pore diameter; at least about 265 nm pore diameter; at least about 270 nm pore diameter; at least about 275 nm pore diameter; at least about 280 nm pore diameter; at least about 285 nm pore diameter; at least about 290 nm pore diameter; at least about 295 nm pore diameter; at least about 300 nm pore diameter; at least about 305 nm pore diameter; at least about 310 nm pore diameter; at least about 315 nm pore diameter; at least about 330 nm pore diameter; at least about 335 nm pore diameter; at least about 340 nm pore diameter; at least about 345 nm pore diameter; at least about 350 nm pore diameter; at least about 355 nm pore diameter; at least about 360 nm pore diameter; at least about 365 nm pore diameter; at least about 370 nm pore diameter; at least about 375 nm pore diameter; at least about 400 nm pore diameter; at least about 410 nm pore diameter; at least about 420 nm pore diameter; at least about 430 nm pore diameter; at least about 440 nm pore diameter; at least about 450 nm pore diameter; at least about 460 nm pore diameter; at least about 470 nm pore diameter; at least about 480 nm pore diameter; at least about 490 nm pore diameter; at least about 500 nm pore diameter; at least about 600 nm pore diameter; at least about 700 nm pore diameter; at least about 800 nm pore diameter; at least about 900 nm pore diameter; at least about 1000 nm pore diameter; at least about 1100 nm pore diameter; at least about 1200 nm pore diameter; at least about 1300 nm pore diameter; at least about 1400 nm pore diameter; at least about 1500 nm pore diameter; at least about 1600 nm pore diameter; at least about 1700 nm pore diameter; at least about 1800 nm pore diameter; at least about 1900 nm pore diameter; at least about 2000 nm pore diameter; at least about 2100 nm pore diameter; at least about 2200 nm pore diameter; at least about 2300 nm pore diameter; at least about 2400 nm pore diameter; at least about 2500 nm pore diameter; at least about 2600 nm pore diameter; at least about 2700 nm pore diameter; at least about 2800 nm pore diameter; at least about 2900 nm pore diameter; at least about 3000 nm pore diameter; at least about 3100 nm pore diameter; at least about 3200 nm pore diameter; at least about 3300 nm pore diameter; at least about 3400 nm pore diameter; or at least about 3500 nm pore diameter. It is understood that recitation of the above discrete values includes a range between each recited value.

As another example, the mineral coating, as described herein, can include about 1 nm pore diameter; about 10 nm pore diameter; about 20 nm pore diameter; about 30 nm pore diameter; about 40 nm pore diameter; about 50 nm pore diameter; about 55 nm pore diameter; about 60 nm pore diameter; about 65 nm pore diameter; about 70 nm pore diameter; about 75 nm pore diameter; about 80 nm pore diameter; about 85 nm pore diameter; about 90 nm pore diameter; about 95 nm pore diameter; about 100 nm pore diameter; about 105 nm pore diameter; about 110 nm pore diameter; about 115 nm pore diameter; about 120 nm pore diameter; about 125 nm pore diameter; about 130 nm pore diameter; about 140 nm pore diameter; about 145 nm pore diameter; about 150 nm pore diameter; about 155 nm pore diameter; about 160 nm pore diameter; about 165 nm pore diameter; about 170 nm pore diameter; about 175 nm pore diameter; about 180 nm pore diameter; about 185 nm pore diameter; about 190 nm pore diameter; about 200 nm pore diameter; about 205 nm pore diameter; about 210 nm pore diameter; about 215 nm pore diameter; about 220 nm pore diameter; about 225 nm pore diameter; about 230 nm pore diameter; about 235 nm pore diameter; about 240 nm pore diameter; about 245 nm pore diameter; about 250 nm pore diameter; about 255 nm pore diameter; about 260 nm pore diameter; about 265 nm pore diameter; about 270 nm pore diameter; about 275 nm pore diameter; about 280 nm pore diameter; about 285 nm pore diameter; about 290 nm pore diameter; about 295 nm pore diameter; about 300 nm pore diameter; about 305 nm pore diameter; about 310 nm pore diameter; about 315 nm pore diameter; about 330 nm pore diameter; about 335 nm pore diameter; about 340 nm pore diameter; about 345 nm pore diameter; about 350 nm pore diameter; about 355 nm pore diameter; about 360 nm pore diameter; about 365 nm pore diameter; about 370 nm pore diameter; about 375 nm pore diameter; about 400 nm pore diameter; about 410 nm pore diameter; about 420 nm pore diameter; about 430 nm pore diameter; about 440 nm pore diameter; about 450 nm pore diameter; about 460 nm pore diameter; about 470 nm pore diameter; about 480 nm pore diameter; about 490 nm pore diameter; about 500 nm pore diameter; about 600 nm pore diameter; about 700 nm pore diameter; about 800 nm pore diameter; about 900 nm pore diameter; about 1000 nm pore diameter; about 1100 nm pore diameter; about 1200 nm pore diameter; about 1300 nm pore diameter; about 1400 nm pore diameter; about 1500 nm pore diameter; about 1600 nm pore diameter; about 1700 nm pore diameter; about 1800 nm pore diameter; about 1900 nm pore diameter; about 2000 nm pore diameter; about 2100 nm pore diameter; about 2200 nm pore diameter; about 2300 nm pore diameter; about 2400 nm pore diameter; about 2500 nm pore diameter; about 2600 nm pore diameter; about 2700 nm pore diameter; about 2800 nm pore diameter; about 2900 nm pore diameter; about 3000 nm pore diameter; about 3100 nm pore diameter; about 3200 nm pore diameter; about 3300 nm pore diameter; about 3400 nm pore diameter; or about 3500 nm pore diameter. It is understood that recitation of the above discrete values includes a range between each recited value.

The mineral coating, as described herein, can include a ratio of at least about 0.1 Ca/P. For example, the mineral coating can include a ratio of at least about 0.1 Ca/P; at least about 0.2 Ca/P; at least about 0.3 Ca/P; at least about 0.4 Ca/P; at least about 0.5 Ca/P; at least about 0.6 Ca/P; at least about 0.7 Ca/P; at least about 0.8 Ca/P; at least about 0.9 Ca/P; at least about 1.0 Ca/P; at least about 1.1 Ca/P; at least about 1.2 Ca/P; at least about 1.3 Ca/P; at least about 1.4 Ca/P; at least about 1.5 Ca/P; at least about 1.6 Ca/P; at least about 1.7 Ca/P; at least about 1.8 Ca/P; at least about 1.9 Ca/P; at least about 2.0 Ca/P; at least about 2.1 Ca/P; at least about 2.2 Ca/P; at least about 2.3 Ca/P; at least about 2.4 Ca/P; at least about 2.5 Ca/P; at least about 2.6 Ca/P; at least about 2.7 Ca/P; at least about 2.8 Ca/P; at least about 2.9 Ca/P; at least about 3.0 Ca/P; at least about 3.1 Ca/P; at least about 3.2 Ca/P; at least about 3.3 Ca/P; at least about 3.4 Ca/P; at least about 3.5 Ca/P; at least about 3.6 Ca/P; at least about 3.7 Ca/P; at least about 3.8 Ca/P; at least about 3.9 Ca/P; at least about 4 Ca/P; at least about 5 Ca/P; at least about 6 Ca/P; at least about 7 Ca/P; at least about 8 Ca/P; at least about 9 Ca/P; at least about 10 Ca/P; at least about 11 Ca/P; at least about 12 Ca/P; at least about 13 Ca/P; at least about 14 Ca/P; at least about 15 Ca/P; at least about 16 Ca/P; at least about 17 Ca/P; at least about 18 Ca/P; at least about 19 Ca/P; or at least about 20 Ca/P. It is understood that recitation of the above discrete values includes a range between each recited value.

As another example, the mineral coating can include a ratio of about 0.1 Ca/P; about 0.2 Ca/P; about 0.3 Ca/P; about 0.4 Ca/P; about 0.5 Ca/P; about 0.6 Ca/P; about 0.7 Ca/P; about 0.8 Ca/P; about 0.9 Ca/P; about 1.0 Ca/P; about 1.1 Ca/P; about 1.2 Ca/P; about 1.3 Ca/P; about 1.4 Ca/P; about 1.5 Ca/P; about 1.6 Ca/P; about 1.7 Ca/P; about 1.8 Ca/P; about 1.9 Ca/P; about 2.0 Ca/P; about 2.1 Ca/P; about 2.2 Ca/P; about 2.3 Ca/P; about 2.4 Ca/P; about 2.5 Ca/P; about 2.6 Ca/P; about 2.7 Ca/P; about 2.8 Ca/P; about 2.9 Ca/P; about 3.0 Ca/P; about 3.1 Ca/P; about 3.2 Ca/P; about 3.3 Ca/P; about 3.4 Ca/P; about 3.5 Ca/P; about 3.6 Ca/P; about 3.7 Ca/P; about 3.8 Ca/P; about 3.9 Ca/P; about 4 Ca/P; about 5 Ca/P; about 6 Ca/P; about 7 Ca/P; about 8 Ca/P; about 9 Ca/P; about 10 Ca/P; about 11 Ca/P; about 12 Ca/P; about 13 Ca/P; about 14 Ca/P; about 15 Ca/P; about 16 Ca/P; about 17 Ca/P; about 18 Ca/P; about 19 Ca/P; or about 20 Ca/P. It is understood that recitation of the above discrete values includes a range between each recited value.

A mineral coating, as described herein, can be characterized by conventional methods. For example, mineral formation in mSBF can be tracked by analyzing changes in solution calcium concentration using a calcium sensitive electrode (Denver Instrument, Denver, Colo.). After their growth, the mineral matrices can be dissolved and analyzed for calcium and phosphate ion content to quantify mineral formation, and the mineral crystals can be analyzed morphologically and compositionally using a scanning electron microscope (SEM), e.g., with a Noran SiLi detector for elemental analysis.

For example, the crystalline phase can be characterized by X-ray diffraction, where 2θ is in the range of 15-35° or 25.8°, 28.1°, 28.9°, 31.8°, and 32.1°.

As another example, as described herein, the chemical composition or crystalline phase can be characterized by Fourier transform infrared spectroscopy (FTIR), where carbonate peaks can be in the 1400-1500 $cm^{-1}$ region and phosphate peaks can be in the 900-1100 $cm^{-1}$ region or about 570 $cm^{-1}$, 962 $cm^{-1}$, and 1050 $cm^{-1}$.

As another example, as described herein, dissolution of mineral layers can also be characterized by measuring release of calcium and phosphate ions during incubation in tris-buffered saline at physiologically relevant conditions (e.g., 37° C., pH 7.4).

As another example, as described herein, calcium and phosphate concentrations can be measured using previously described colorimetric assays (see Murphy et al., "Bioinspired growth of crystalline carbonate apatite on biodegradable polymer substrata", *J Am Chem Soc* 124:1910–7, 2002). Each of the characterization methods described herein are routine in analysis of inorganic materials, and is consistent with FDA's good guidance practices for design and testing of calcium phosphate coatings (see Devices FDoGaR. Calcium phosphate coating draft guidance for preparation of FDA submissions for orthopedic and dental endosseous implants. 1997).

As another example, as described herein, the mineral coating, can be predominantly crystalline, but can be present in amorphous forms. For example, the mineral coating can have at least about 5% crystallinity. For example, a mineral coating can include at least about 5% crystallinity; at least about 10% crystallinity; at least about 15% crystallinity; at least about 20% crystallinity; at least about 25% crystallinity; at least about 30% crystallinity; at least about 40% crystallinity; at least about 45% crystallinity; at least about 46% crystallinity; at least about 47% crystallinity; at least about 48% crystallinity; at least about 49% crystallinity; at least about 50% crystallinity; at least about 51% crystallinity; at least about 52% crystallinity; at least about 53% crystallinity; at least about 54% crystallinity; at least about 55% crystallinity; at least about 56% crystallinity; at least about 57% crystallinity; at least about 58% crystallinity; at least about 59% crystallinity; at least about 60% crystallinity; at least about 61% crystallinity; at least about 62% crystallinity; at least about 63% crystallinity; at least about 64% crystallinity; at least about 65% crystallinity; at least about 66% crystallinity; at least about 67% crystallinity; at least about 68% crystallinity; at least about 69% crystallinity; at least about 70% crystallinity; at least about 71% crystallinity; at least about 72% crystallinity; at least about 73% crystallinity; at least about 74% crystallinity; at least about 75% crystallinity; at least about 76% crystallinity; at least about 77% crystallinity; at least about 78% crystallinity; at least about 79% crystallinity; at least about 80% crystallinity; at least about 81% crystallinity; at least about 82% crystallinity; at least about 83% crystallinity; at least about 84% crystallinity; at least about 85% crystallinity; at least about 86% crystallinity; at least about 87% crystallinity; at least about 88% crystallinity; at least about 89% crystallinity; at least about 90% crystallinity; at least about 91% crystallinity; at least about 92% crystallinity; at least about 93% crystallinity; at least about 94% crystallinity; at least about 95% crystallinity; at least about 96% crystallinity; at least about 97% crystallinity; at least about 98% crystallinity; at least about 99% crystallinity; or at least about 100% crystallinity. It is understood that recitation of the above discrete values includes a range between each recited value.

As another example, a mineral coating can include about 5% crystallinity; 10% crystallinity; about 15% crystallinity; about 20% crystallinity; about 25% crystallinity; about 30% crystallinity; about 40% crystallinity; about 45% crystallinity; about 46% crystallinity; about 47% crystallinity; about 48% crystallinity; about 49% crystallinity; about 50% crystallinity; about 51% crystallinity; about 52% crystallinity; about 53% crystallinity; about 54% crystallinity; about 55% crystallinity; about 56% crystallinity; about 57% crystallinity; about 58% crystallinity; about 59% crystallinity; about 60% crystallinity; about 61% crystallinity; about 62% crystallinity; about 63% crystallinity; about 64% crystallinity; about 65% crystallinity; about 66% crystallinity; about 67% crystallinity; about 68% crystallinity; about 69% crystallinity; about 70% crystallinity; about 71% crystallinity; about 72% crystallinity; about 73% crystallinity; about 74% crystallinity; about 75% crystallinity; about 76% crystallinity; about 77% crystallinity; about 78% crystallinity; about 79% crystallinity; about 80% crystallinity; about 81% crystallinity; about 82% crystallinity; about 83% crystallinity; about 84% crystallinity; about 85% crystallinity; about 86% crystallinity; about 87% crystallinity; about 88% crystallinity; about 89% crystallinity; about 90% crystallinity; about 91% crystallinity; about 92% crystallinity; about 93% crystallinity; about 94% crystallinity; about 95% crystallinity; about 96% crystallinity; about 97% crystallinity; about 98% crystallinity; about 99% crystallinity; or about 100% crystallinity. It is understood that recitation of the above discrete values includes a range between each recited value.

As described herein, osteoconductivity and osteoinductivity can be conferred to scaffolds (e.g., orthopedic implant materials) using calcium phosphate coatings. Based on the well-defined osteoconductivity and potential osteoinductivity of calcium-phosphate-based mineral coatings, calcium phosphate mineral growth can be advantageously utilized to coat scaffolds.

Auxiliary Components

The mineral coating, as described herein, can include auxiliary components. For example, the auxiliary components can be incorporated onto the scaffold, the surface of the coating, or within the coating of the scaffold.

For example, an auxiliary component can provide desirable characteristics to the mineral coating, such as improved osteoconductivity, osteoinductivity, osteopromotion, osteogenesis, strength, antibacterial, antimicrobial properties, biostatic, or anti-infection properties.

As described herein, an auxiliary component can be an organic or collagen matrix, such as demineralized bone matrix (DBM). As described herein, DBM can be of any form known in the art. For example DBM can be a demineralized bone powder, demineralized bone extract, demineralized bone gelatin, granules, fragments, pellets, slices, shavings, putty, paste, mix, or strips.

As described herein, DBM can be incorporated into or onto the coating or scaffold by any method known in the art. As another example, DBM can be loaded or integrated into a porous material, such as a porous scaffold. As another example, DBM can be loaded into a medical device, such as a porous, coated, bioresorbable implant formed via 3-D printing. As another example, DBM can be combined with a mineral-coated device. As another example, DBM can be incorporated with the mineral coating, scaffold, or matrix material by mixing, coating, or loading.

As described herein DBM can be integrated with the scaffold or mineral coated scaffold by any method known in the art. The incorporation of DBM into a mineral coating can be as described in Ozturk et al. 2006 Int Orth 30, 147-152 or US Pat Pub No. 2008/0233203.

As described herein, preparing DBM to be integrated with a scaffold can comprise mixing DBM with an aqueous solution. For example, the aqueous solution can be the mineral coating solution as described herein. As another example, the aqueous solution can be a weak acid or guanidine hydrochloride. The mixture can be constantly agitated for a set amount of time to produce an aqueous demineralized bone extract. The extract can then be filtered to remove any remaining solids, the acid neutralized or removed, and the extract used to coat the porous scaffold.

As described herein, the amount of DBM in a solution can be from about 1 g to about 99 g DBM or from about 2 g to about 10 g DBM per 100 g of aqueous solution. The amount of DBM can comprise at least about 1 g DBM per 100 g aqueous solution. For example, the amount of DBM in a solution can comprise at least about 1 g DBM per 100 g aqueous solution; at least about 2 g DBM per 100 g aqueous solution; at least about 3 g DBM per 100 g aqueous solution; at least about 4 g DBM per 100 g aqueous solution; at least about 5 g DBM per 100 g aqueous solution; at least about 6 g DBM per 100 g aqueous solution; at least about 7 g DBM per 100 g aqueous solution; at least about 8 g DBM per 100 g aqueous solution; at least about 9 g DBM per 100 g aqueous solution; at least about 10 g DBM per 100 g aqueous solution; at least about 11 g DBM per 100 g aqueous solution; at least about 12 g DBM per 100 g aqueous solution; at least about 13 g DBM per 100 g aqueous solution; at least about 14 g DBM per 100 g aqueous solution; at least about 15 g DBM per 100 g aqueous solution; at least about 16 g DBM per 100 g aqueous solution; at least about 17 g DBM per 100 g aqueous solution; at least about 18 g DBM per 100 g aqueous solution; at least about 19 g DBM per 100 g aqueous solution; at least about 20 g DBM per 100 g aqueous solution; at least about 21 g DBM per 100 g aqueous solution; at least about 22 g DBM per 100 g aqueous solution; at least about 23 g DBM per 100 g aqueous solution; at least about 24 g DBM per 100 g aqueous solution; at least about 25 g DBM per 100 g aqueous solution; at least about 26 g DBM per 100 g aqueous solution; at least about 27 g DBM per 100 g aqueous solution; at least about 28 g DBM per 100 g aqueous solution; at least about 29 g DBM per 100 g aqueous solution; at least about 30 g DBM per 100 g aqueous solution; at least about 31 g DBM per 100 g aqueous solution; at least about 32 g DBM per 100 g aqueous solution; at least about 33 g DBM per 100 g aqueous solution; at least about 34 g DBM per 100 g aqueous solution; at least about 35 g DBM per 100 g aqueous solution; at least about 36 g DBM per 100 g aqueous solution; at least about 37 g DBM per 100 g aqueous solution; at least about 38 g DBM per 100 g aqueous solution; at least about 39 g DBM per 100 g aqueous solution; at least about 40 g DBM per 100 g aqueous solution; at least about 41 g DBM per 100 g aqueous solution; at least about 42 g DBM per 100 g aqueous solution; at least about 43 g DBM per 100 g aqueous solution; at least about 44 g DBM per 100 g aqueous solution; at least about 45 g DBM per 100 g aqueous solution; at least about 46 g DBM per 100 g aqueous solution; at least about 47 g DBM per 100 g aqueous solution; at least about 48 g DBM per 100 g aqueous solution; at least about 49 g DBM per 100 g aqueous solution; at least about 50 g DBM per 100 g aqueous solution; at least about 51 g DBM per 100 g aqueous solution; at least about 52 g DBM per 100 g aqueous solution; at least about 53 g DBM per 100 g aqueous solution; at least about 54 g DBM per 100 g aqueous solution; at least about 55 g DBM per 100 g aqueous solution; at least about 56 g DBM per 100 g aqueous solution; at least about 57 g DBM per 100 g aqueous solution; at least about 58 g DBM per 100 g aqueous solution; at least about 59 g DBM per 100 g aqueous solution; at least about 60 g DBM per 100 g aqueous solution; at least about 61 g DBM per 100 g aqueous solution; at least about 62 g DBM per 100 g aqueous solution; at least about 63 g DBM per 100 g aqueous solution; at least about 64 g DBM per 100 g aqueous solution; at least about 65 g DBM per 100 g aqueous solution; at least about 66 g DBM per 100 g aqueous solution; at least about 67 g DBM per 100 g aqueous solution; at least about 68 g DBM per 100 g aqueous solution; at least about 69 g DBM per 100 g aqueous solution; at least about 70 g DBM per 100 g aqueous solution; at least about 71 g DBM per 100 g aqueous solution; at least about 72 g DBM per 100 g aqueous solution; at least about 73 g DBM per 100 g aqueous solution; at least about 74 g DBM per 100 g aqueous solution; at least about 75 g DBM per 100 g aqueous solution; at least about 76 g DBM per 100 g aqueous solution; at least about 77 g DBM per 100 g aqueous solution; at least about 78 g DBM per 100 g aqueous solution; at least about 79 g DBM per 100 g aqueous solution; at least about 80 g DBM per 100 g aqueous solution; at least about 81 g DBM per 100 g aqueous solution; at least about 82 g DBM per 100 g aqueous solution; at least about 83 g DBM per 100 g aqueous solution; at least about 84 g DBM per 100 g aqueous solution; at least about 85 g DBM per 100 g aqueous solution; at least about 86 g DBM per 100 g aqueous solution; at least about 87 g DBM per 100 g aqueous solution; at least about 88 g DBM per 100 g aqueous solution; at least about 89 g DBM per 100 g aqueous solution; at least about 90 g DBM per 100 g aqueous solution; at least about 91 g DBM per 100 g aqueous solution; at least about 92 g DBM per 100 g aqueous solution; at least about 93 g DBM per 100 g aqueous solution; at least about 94 g DBM per 100 g aqueous solution; at least about 95 g DBM per 100 g aqueous solution; at least about 96 g DBM per 100 g aqueous solution; at least about 97 g DBM per 100 g aqueous solution; at least about 98 g DBM per 100 g aqueous solution; or at least about 99 g DBM per 100 g aqueous solution per 100 g of aqueous solution. It is understood that recitation of the above discrete values includes a range between each recited value.

As another example, the amount of DBM can comprise about 1 g DBM per 100 g aqueous solution. The amount of DBM can comprise about 1 g DBM per 100 g aqueous solution; about 2 g DBM per 100 g aqueous solution; about 3 g DBM per 100 g aqueous solution; about 4 g DBM per 100 g aqueous solution; about 5 g DBM per 100 g aqueous solution; about 6 g DBM per 100 g aqueous solution; about 7 g DBM per 100 g aqueous solution; about 8 g DBM per 100 g aqueous solution; about 9 g DBM per 100 g aqueous solution; about 10 g DBM per 100 g aqueous solution; about 11 g DBM per 100 g aqueous solution; about 12 g DBM per 100 g aqueous solution; about 13 g DBM per 100 g aqueous solution; about 14 g DBM per 100 g aqueous solution; about 15 g DBM per 100 g aqueous solution; about 16 g DBM per 100 g aqueous solution; about 17 g DBM per 100 g aqueous solution; about 18 g DBM per 100 g aqueous solution; about 19 g DBM per 100 g aqueous solution; about 20 g DBM per 100 g aqueous solution; about 21 g DBM per 100 g aqueous solution; about 22 g DBM per 100 g aqueous solution; about 23 g DBM per 100 g aqueous solution; about 24 g DBM per 100 g aqueous solution; about 25 g DBM per 100 g aqueous solution; about 26 g DBM per 100 g aqueous solution; about 27 g DBM per 100 g aqueous solution; about 28 g DBM per 100 g aqueous solution; about 29 g DBM per 100 g aqueous solution; about 30 g DBM per 100 g aqueous solution; about 31 g DBM per 100 g aqueous solution; about 32 g DBM per 100 g aqueous solution; about 33 g DBM per 100 g aqueous solution; about 34 g DBM per 100 g aqueous solution; about 35 g DBM per 100 g aqueous solution; about 36 g DBM per 100 g aqueous solution; about 37 g DBM per 100 g aqueous solution; about 38 g DBM per 100 g aqueous solution; about 39 g DBM per 100 g aqueous solution; about 40 g DBM per 100 g aqueous solution; about 41 g DBM per 100 g aqueous solution; about 42 g DBM per 100 g aqueous solution; about 43 g DBM per 100 g aqueous solution; about 44 g DBM per 100 g aqueous solution; about 45 g DBM per 100 g aqueous solution; about 46 g DBM per 100 g aqueous solution; about 47 g DBM per 100 g aqueous solution; about 48 g DBM per 100 g aqueous solution; about 49 g DBM per 100 g aqueous solution; about 50 g DBM per 100 g aqueous solution; about 51 g DBM per 100 g aqueous solution; about 52 g DBM per 100 g aqueous solution; about 53 g DBM per 100 g aqueous solution; about 54 g DBM per 100 g aqueous solution; about 55 g DBM per 100 g aqueous solution; about 56 g DBM per 100 g aqueous solution; about 57 g DBM per 100 g aqueous solution; about 58 g DBM per 100 g aqueous solution; about 59 g DBM per 100 g aqueous solution; about 60 g DBM per 100 g aqueous solution; about 61 g DBM per 100 g aqueous solution; about 62 g DBM per 100 g aqueous solution; about 63 g DBM per 100 g aqueous solution; about 64 g DBM per 100 g aqueous solution; about 65 g DBM per 100 g aqueous solution; about 66 g DBM per 100 g aqueous solution; about 67 g DBM per 100 g aqueous solution; about 68 g DBM per 100 g aqueous solution; about 69 g DBM per 100 g aqueous solution; about 70 g DBM per 100 g aqueous solution; about 71 g DBM per 100 g aqueous solution; about 72 g DBM per 100 g aqueous solution; about 73 g DBM per 100 g aqueous solution; about 74 g DBM per 100 g aqueous solution; about 75 g DBM per 100 g aqueous solution; about 76 g DBM per 100 g aqueous solution; about 77 g DBM per 100 g aqueous solution; about 78 g DBM per 100 g aqueous solution; about 79 g DBM per 100 g aqueous solution; about 80 g DBM per 100 g aqueous solution; about 81 g DBM per 100 g aqueous solution; about 82 g DBM per 100 g aqueous solution; about 83 g DBM per 100 g aqueous solution; about 84 g DBM per 100 g aqueous solution; about 85 g DBM per 100 g aqueous solution; about 86 g DBM per 100 g aqueous solution; about 87 g DBM per 100 g aqueous solution; about 88 g DBM per 100 g aqueous solution; about 89 g DBM per 100 g aqueous solution; about 90 g DBM per 100 g aqueous solution; about 91 g DBM per 100 g aqueous solution; about 92 g DBM per 100 g aqueous solution; about 93 g DBM per 100 g aqueous solution; about 94 g DBM per 100 g aqueous solution; about 95 g DBM per 100 g aqueous solution; about 96 g DBM per 100 g aqueous solution; about 97 g DBM per 100 g aqueous solution; about 98 g DBM per 100 g aqueous solution; or about 99 g DBM per 100 g aqueous solution. It is understood that recitation of the above discrete values includes a range between each recited value.

The aqueous solution can comprise the mineral coating solution as described herein. The aqueous solution can comprise any biologically compatible aqueous solution, particularly those in which mineral coating components, growth factors, and proteins may be stable in. Examples of such solutions can be, but not limited to the mineral coating solution as described above, Tris buffer, Tris buffered saline, phosphate buffer and phosphate buffered saline. For example, the solution can be a weak acid solution where the weak acid can be, but not limited to, citric acid, lactic acid, malic acid, ascorbic acid or combinations thereof. Any weak acid known in the art can be used. The concentration of the weak acid solution can be from about 2 M to about 3 M. In a second illustrative embodiment, the solution can be a guanidine hydrochloride solution where the concentration of the guanidine hydrochloride solution can be from about 3 M to about 6 M.

The amount of time that the DBM and aqueous solution can be mixed from about 8 hours to about 96 hours. For example, the DBM and aqueous solution can be mixed together from about 24 hours to about 96 hours. The DBM and aqueous solution can be mixed together with constant agitation during that time. Constant agitation can be obtained by, but not limited to, stirring, shaking, ultrasound or any combination thereof as well as any other methods of agitating a mixture.

The mixing can be carried out at a temperature that can be conducive to coating a scaffold and extracting growth factors and/or proteins from the DBM, but where growth factors and/or proteins can be stable. The temperature can be less than 50° C. As another example, the temperature can be room temperature.

After mixing for the appropriate amount of time, the resulting demineralized bone extract can be separated from any insoluble DBM remaining in the solution. This separation can occur by any number of processes such as, but not limited to, decanting, filtering, or centrifuging. For example, the solution can be filtered to remove any soluble DBM remaining. The size of the sieve or filter will depend on the size of the DBM particles remaining, which can further depend on the initial form of DBM. For example, the filter can be from about 50 microns to about 300 microns. As another example, the filter can be a sieve, paper, scintered glass, woven or non-woven fabric, or any other means of filtering that is known in the art.

The demineralized bone extract can be diluted, neutralized or the weak acid or guanidine hydrochloride removed. Methods can include, but are not limited to, titration, dialysis, liquid-liquid extraction, hollow fiber filtration, ultrafiltration, crossflow filtration or precipitation. For example, the aqueous solution can be neutralized to a pH of from about 6.5 to about 7.5 by titration with an appropriate counterion. Such methods are well known in the art. As another example, the weak acid or guanidine hydrochloride can be removed by dialysis, hollow fiber filtration, ultrafiltration or crossflow filtration against a biologically compatible buffer, such as, but not limited to, Tris, TBS, phosphate, PBS or water, where the pH of the buffer can be from about 6.5 to about 7.5. The molecular weight cutoff of the dialysis membrane will depend on the size of the proteins and/or growth factors desired in the solution. The dialysis, hollow fiber filtration, ultrafiltration or crossflow filtration membrane can have, for example, a molecular weight cut off less than or equal to 12 Kd or from about 10 Kd to about 12 Kd. It is well known in the art how to select the molecular weight cut off of dialysis tubing to retain the desired molecules within the sample.

The demineralized bone extract can include the mineral coating solution or be mixed with the mineral coating solution as described herein. For example, the bone extract can be introduced during the scaffold incubation step in the mineral coating procedure as described in Example 4.

As described herein, a mineral coated scaffold can be coated simultaneously with the demineralized bone material or the mineral coated scaffold can be coated with the demineralizing bone material.

The demineralized bone extract can be applied to the scaffold such that the demineralized bone extract infiltrates the pores and passageways of the scaffold. For example, the demineralized bone extract can be applied to the scaffold under vacuum. As another example, the demineralized bone extract can be applied to the scaffold by dipping the structure into the extract and allowing it to infiltrate the pores and passageways by capillary action. After the demineralized bone extract has been applied to the scaffold, it can be dried onto the scaffold. The demineralized bone extract can be dried onto the structure by lyophilization, vacuum, heating, or a combination thereof. In one or more embodiments, the heating can be at a temperature less than 50° C.

As described herein, the method of the present invention can further comprise making a demineralized bone gelatin. The demineralized bone gelatin can be coated over the demineralized bone extract or mineral coating, or it can be mixed with the extract before coating to form a single coating or it can be mixed with the mineral coating to form a single coating. The demineralized bone gelatin can be formed by mixing DBM with an aqueous saline solution such as, but not limited to PBS, TBS, or a sodium chloride solution, to form a suspension. The suspension can be treated to increased temperature and pressure such as, but not limited to, autoclaved. In one illustrative embodiment, the solution can be heated to a temperature of from about 85° C. to about 130° C. at a pressure of at least about 15 psig. The DBM can be dissolved to produce a demineralized bone gelatin. Methods for forming a demineralized bone gelatin are known in the art. The DBM can be the solids removed during the filtering step while forming the demineralized bone extract or it can be fresh DBM. Alternatively, it will be appreciated that since the demineralized bone gelatin comprises mainly collagen, collagen of any purity can be substituted for the DBM.

The demineralized bone gelatin can be coated over the dried demineralized bone extract coating on the scaffold such that the gelatin coats the pores and passageways. Alternatively, the demineralized bone gelatin can be mixed with the demineralized bone extract prior to the extract being coated onto the scaffold to form a single coating. The scaffold can be pre-coated with the mineral coating or the mineral coating solution can be incorporated into the DBM coating. The coating comprising the demineralized bone extract and gelatin can then be applied to the scaffold such that the pores and passageways are coated. It will be appreciated that the demineralized bone gelatin can be less viscous at higher temperatures, making it easier to apply to the scaffold. The demineralized bone gelatin can be applied to the scaffold in a less viscous form such as a solution. The demineralized bone gelatin can be allowed to gel before any other steps are performed. The demineralized bone gelatin coating can be maintained at a temperature low enough as to not to inactivate any growth factors and/or proteins of the demineralized bone extract coating.

Once applied, the demineralized bone gelatin, either alone or mixed with the demineralized bone extract or mineral coating, can be dried onto the scaffold. The scaffold can be pre-coated with the mineral coating. The demineralized bone gelatin can be dried onto the structure by lyophilization, vacuum, heating, or a combination thereof. In one or more embodiments, the heating can be at a temperature not greater than 50° C.

As described herein, DBM can be integrated into the mineral coating or into a scaffold. For example, DBM can be integrated into the mineral coating or scaffold by % weight (w/w) or by % volume (v/v). A mineral coating or scaffold can comprise at least about 1% (w/w) DBM. For example, a mineral coating or scaffold can comprise at least about 1% (w/w) DBM; at least about 2% (w/w) DBM; at least about 3% (w/w) DBM; at least about 4% (w/w) DBM; at least about 5% (w/w) DBM; at least about 6% (w/w) DBM; at least about 7% (w/w) DBM; at least about 8% (w/w) DBM; at least about 9% (w/w) DBM; at least about 10% (w/w) DBM; at least about 11% (w/w) DBM; at least about 12% (w/w) DBM; at least about 13% (w/w) DBM; at least about 14% (w/w) DBM; at least about 15% (w/w) DBM; at least about 16% (w/w) DBM; at least about 17% (w/w) DBM; at least about 18% (w/w) DBM; at least about 19% (w/w) DBM; at least about 20% (w/w) DBM; at least about 21% (w/w) DBM; at least about 22% (w/w) DBM; at least about 23% (w/w) DBM; at least about 24% (w/w) DBM; at least about 25% (w/w) DBM; at least about 26% (w/w) DBM; at least about 27% (w/w) DBM; at least about 28% (w/w) DBM; at least about 29% (w/w) DBM; at least about 30% (w/w) DBM; at least about 31% (w/w) DBM; at least about 32% (w/w) DBM; at least about 33% (w/w) DBM; at least about 34% (w/w) DBM; at least about 35% (w/w) DBM; at least about 36% (w/w) DBM; at least about 37% (w/w) DBM; at least about 38% (w/w) DBM; at least about 39% (w/w) DBM; at least about 40% (w/w) DBM; at least about 41% (w/w) DBM; at least about 42% (w/w) DBM; at least about 43% (w/w) DBM; at least about 44% (w/w) DBM; at least about 45% (w/w) DBM; at least about 46% (w/w) DBM; at least about 47% (w/w) DBM; at least about 48% (w/w) DBM; at least about 49% (w/w) DBM; at least about 50% (w/w) DBM; at least about 51% (w/w) DBM; at least about 52% (w/w) DBM; at least about 53% (w/w) DBM; at least about 54% (w/w) DBM; at least about 55% (w/w) DBM; at least about 56% (w/w) DBM; at least about 57% (w/w) DBM; at least about 58% (w/w) DBM; at least about 59% (w/w) DBM; at least about 60% (w/w) DBM; at least about 61% (w/w) DBM; at least about 62% (w/w) DBM; at least about 63% (w/w) DBM; at least about 64% (w/w) DBM; at least about 65% (w/w) DBM; at least about 66% (w/w) DBM; at least about 67% (w/w) DBM; at least about 68% (w/w) DBM; at least about 69% (w/w) DBM; at least about 70% (w/w) DBM; at least about 71% (w/w) DBM; at least about 72% (w/w) DBM; at least about 73% (w/w) DBM; at least about 74% (w/w) DBM; at least about 75% (w/w) DBM; at least about 76% (w/w) DBM; at least about 77% (w/w) DBM; at least about 78% (w/w) DBM; at least about 79% (w/w) DBM; at least about 80% (w/w) DBM; at least about 81% (w/w) DBM; at least about 82% (w/w) DBM; at least about 83% (w/w) DBM; at least about 84% (w/w) DBM; at least about 85% (w/w) DBM; at least about 86% (w/w) DBM; at least about 87% (w/w) DBM; at least about 88% (w/w) DBM; at least about 89% (w/w) DBM; at least about 90% (w/w) DBM; at least about 91% (w/w) DBM; at least about 92% (w/w) DBM; at least about 93% (w/w) DBM; at least about 94% (w/w) DBM; at least about 95% (w/w) DBM; at least about 96% (w/w) DBM; at least about 97% (w/w) DBM; at least about 98% (w/w) DBM; or at least about 99% (w/w) DBM. It is understood that recitation of the above discrete values includes a range between each recited value.

As another example, a mineral coating or scaffold can comprise about 1% (w/w) DBM; about 2% (w/w) DBM; about 3% (w/w) DBM; about 4% (w/w) DBM; about 5% (w/w) DBM; about 6% (w/w) DBM; about 7% (w/w) DBM; about 8% (w/w) DBM; about 9% (w/w) DBM; about 10% (w/w) DBM; about 11% (w/w) DBM; about 12% (w/w) DBM; about 13% (w/w) DBM; about 14% (w/w) DBM; about 15% (w/w) DBM; about 16% (w/w) DBM; about 17% (w/w) DBM; about 18% (w/w) DBM; about 19% (w/w) DBM; about 20% (w/w) DBM; about 21% (w/w) DBM; about 22% (w/w) DBM; about 23% (w/w) DBM; about 24% (w/w) DBM; about 25% (w/w) DBM; about 26% (w/w) DBM; about 27% (w/w) DBM; about 28% (w/w) DBM; about 29% (w/w) DBM; about 30% (w/w) DBM; about 31% (w/w) DBM; about 32% (w/w) DBM; about 33% (w/w) DBM; about 34% (w/w) DBM; about 35% (w/w) DBM; about 36% (w/w) DBM; about 37% (w/w) DBM; about 38% (w/w) DBM; about 39% (w/w) DBM; about 40% (w/w) DBM; about 41% (w/w) DBM; about 42% (w/w) DBM; about 43% (w/w) DBM; about 44% (w/w) DBM; about 45% (w/w) DBM; about 46% (w/w) DBM; about 47% (w/w)

DBM; about 48% (w/w) DBM; about 49% (w/w) DBM; about 50% (w/w) DBM; about 51% (w/w) DBM; about 52% (w/w) DBM; about 53% (w/w) DBM; about 54% (w/w) DBM; about 55% (w/w) DBM; about 56% (w/w) DBM; about 57% (w/w) DBM; about 58% (w/w) DBM; about 59% (w/w) DBM; about 60% (w/w) DBM; about 61% (w/w) DBM; about 62% (w/w) DBM; about 63% (w/w) DBM; about 64% (w/w) DBM; about 65% (w/w) DBM; about 66% (w/w) DBM; about 67% (w/w) DBM; about 68% (w/w) DBM; about 69% (w/w) DBM; about 70% (w/w) DBM; about 71% (w/w) DBM; about 72% (w/w) DBM; about 73% (w/w) DBM; about 74% (w/w) DBM; about 75% (w/w) DBM; about 76% (w/w) DBM; about 77% (w/w) DBM; about 78% (w/w) DBM; about 79% (w/w) DBM; about 80% (w/w) DBM; about 81% (w/w) DBM; about 82% (w/w) DBM; about 83% (w/w) DBM; about 84% (w/w) DBM; about 85% (w/w) DBM; about 86% (w/w) DBM; about 87% (w/w) DBM; about 88% (w/w) DBM; about 89% (w/w) DBM; about 90% (w/w) DBM; about 91% (w/w) DBM; about 92% (w/w) DBM; about 93% (w/w) DBM; about 94% (w/w) DBM; about 95% (w/w) DBM; about 96% (w/w) DBM; about 97% (w/w) DBM; about 98% (w/w) DBM; or about 99% (w/w) DBM. It is understood that recitation of the above discrete values includes a range between each recited value.

A mineral coating or scaffold can comprise at least about 1% (v/v) DBM. As another example, a mineral coating or scaffold can comprise at least about 1% (v/v) DBM; at least about 2% (v/v) DBM; at least about 3% (v/v) DBM; at least about 4% (v/v) DBM; at least about 5% (v/v) DBM; at least about 6% (v/v) DBM; at least about 7% (v/v) DBM; at least about 8% (v/v) DBM; at least about 9% (v/v) DBM; at least about 10% (v/v) DBM; at least about 11% (v/v) DBM; at least about 12% (v/v) DBM; at least about 13% (v/v) DBM; at least about 14% (v/v) DBM; at least about 15% (v/v) DBM; at least about 16% (v/v) DBM; at least about 17% (v/v) DBM; at least about 18% (v/v) DBM; at least about 19% (v/v) DBM; at least about 20% (v/v) DBM; at least about 21% (v/v) DBM; at least about 22% (v/v) DBM; at least about 23% (v/v) DBM; at least about 24% (v/v) DBM; at least about 25% (v/v) DBM; at least about 26% (v/v) DBM; at least about 27% (v/v) DBM; at least about 28% (v/v) DBM; at least about 29% (v/v) DBM; at least about 30% (v/v) DBM; at least about 31% (v/v) DBM; at least about 32% (v/v) DBM; at least about 33% (v/v) DBM; at least about 34% (v/v) DBM; at least about 35% (v/v) DBM; at least about 36% (v/v) DBM; at least about 37% (v/v) DBM; at least about 38% (v/v) DBM; at least about 39% (v/v) DBM; at least about 40% (v/v) DBM; at least about 41% (v/v) DBM; at least about 42% (v/v) DBM; at least about 43% (v/v) DBM; at least about 44% (v/v) DBM; at least about 45% (v/v) DBM; at least about 46% (v/v) DBM; at least about 47% (v/v) DBM; at least about 48% (v/v) DBM; at least about 49% (v/v) DBM; at least about 50% (v/v) DBM; at least about 51% (v/v) DBM; at least about 52% (v/v) DBM; at least about 53% (v/v) DBM; at least about 54% (v/v) DBM; at least about 55% (v/v) DBM; at least about 56% (v/v) DBM; at least about 57% (v/v) DBM; at least about 58% (v/v) DBM; at least about 59% (v/v) DBM; at least about 60% (v/v) DBM; at least about 61% (v/v) DBM; at least about 62% (v/v) DBM; at least about 63% (v/v) DBM; at least about 64% (v/v) DBM; at least about 65% (v/v) DBM; at least about 66% (v/v) DBM; at least about 67% (v/v) DBM; at least about 68% (v/v) DBM; at least about 69% (v/v) DBM; at least about 70% (v/v) DBM; at least about 71% (v/v) DBM; at least about 72% (v/v) DBM; at least about 73% (v/v) DBM; at least about 74% (v/v) DBM; at least about 75% (v/v) DBM; at least about 76% (v/v) DBM; at least about 77% (v/v) DBM; at least about 78% (v/v) DBM; at least about 79% (v/v) DBM; at least about 80% (v/v) DBM; at least about 81% (v/v) DBM; at least about 82% (v/v) DBM; at least about 83% (v/v) DBM; at least about 84% (v/v) DBM; at least about 85% (v/v) DBM; at least about 86% (v/v) DBM; at least about 87% (v/v) DBM; at least about 88% (v/v) DBM; at least about 89% (v/v) DBM; at least about 90% (v/v) DBM; at least about 91% (v/v) DBM; at least about 92% (v/v) DBM; at least about 93% (v/v) DBM; at least about 94% (v/v) DBM; at least about 95% (v/v) DBM; at least about 96% (v/v) DBM; at least about 97% (v/v) DBM; at least about 98% (v/v) DBM; or at least about 99% (v/v) DBM. It is understood that recitation of the above discrete values includes a range between each recited value.

As another example, a mineral coating or scaffold can comprise about 1% (v/v) DBM; about 2% (v/v) DBM; about 3% (v/v) DBM; about 4% (v/v) DBM; about 5% (v/v) DBM; about 6% (v/v) DBM; about 7% (v/v) DBM; about 8% (v/v) DBM; about 9% (v/v) DBM; about 10% (v/v) DBM; about 11% (v/v) DBM; about 12% (v/v) DBM; about 13% (v/v) DBM; about 14% (v/v) DBM; about 15% (v/v) DBM; about 16% (v/v) DBM; about 17% (v/v) DBM; about 18% (v/v) DBM; about 19% (v/v) DBM; about 20% (v/v) DBM; about 21% (v/v) DBM; about 22% (v/v) DBM; about 23% (v/v) DBM; about 24% (v/v) DBM; about 25% (v/v) DBM; about 26% (v/v) DBM; about 27% (v/v) DBM; about 28% (v/v) DBM; about 29% (v/v) DBM; about 30% (v/v) DBM; about 31% (v/v) DBM; about 32% (v/v) DBM; about 33% (v/v) DBM; about 34% (v/v) DBM; about 35% (v/v) DBM; about 36% (v/v) DBM; about 37% (v/v) DBM; about 38% (v/v) DBM; about 39% (v/v) DBM; about 40% (v/v) DBM; about 41% (v/v) DBM; about 42% (v/v) DBM; about 43% (v/v) DBM; about 44% (v/v) DBM; about 45% (v/v) DBM; about 46% (v/v) DBM; about 47% (v/v) DBM; about 48% (v/v) DBM; about 49% (v/v) DBM; about 50% (v/v) DBM; about 51% (v/v) DBM; about 52% (v/v) DBM; about 53% (v/v) DBM; about 54% (v/v) DBM; about 55% (v/v) DBM; about 56% (v/v) DBM; about 57% (v/v) DBM; about 58% (v/v) DBM; about 59% (v/v) DBM; about 60% (v/v) DBM; about 61% (v/v) DBM; about 62% (v/v) DBM; about 63% (v/v) DBM; about 64% (v/v) DBM; about 65% (v/v) DBM; about 66% (v/v) DBM; about 67% (v/v) DBM; about 68% (v/v) DBM; about 69% (v/v) DBM; about 70% (v/v) DBM; about 71% (v/v) DBM; about 72% (v/v) DBM; about 73% (v/v) DBM; about 74% (v/v) DBM; about 75% (v/v) DBM; about 76% (v/v) DBM; about 77% (v/v) DBM; about 78% (v/v) DBM; about 78% (v/v) DBM; about 78% (v/v) DBM; about 79% (v/v) DBM; about 80% (v/v) DBM; about 81% (v/v) DBM; about 82% (v/v) DBM; about 83% (v/v) DBM; about 84% (v/v) DBM; about 85% (v/v) DBM; about 86% (v/v) DBM; about 87% (v/v) DBM; about 88% (v/v) DBM; about 89% (v/v) DBM; about 90% (v/v) DBM; about 91% (v/v) DBM; about 92% (v/v) DBM; about 93% (v/v) DBM; about 94% (v/v) DBM; about 95% (v/v) DBM; about 96% (v/v) DBM; about 97% (v/v) DBM; about 98% (v/v) DBM; or about 99% (v/v) DBM. It is understood that recitation of the above discrete values includes a range between each recited value.

As described herein, an auxiliary component can be an antimicrobial agent. For example, an antimicrobial agent can be silver particles. As another example, silver particles can be silver microparticles or silver nanoparticles. Silver particles integrated with the scaffold are presently thought to provide biostatic, anti-infection properties to the scaffold.

As described herein, silver particles can be integrated onto the mineral coating or scaffold. For example, the silver particles can be integrated into the scaffold or coating before, during, or after DBM integration.

As described herein, silver particles can be incorporated onto the surface of a mineral coated scaffold. For example, the silver particles can be incorporated into or onto the mineral coating by any method known in the art. As another example, the incorporation of silver particles can be as described in Lee et al. 2013 Mat. Views 25, 1173-1179; WO 2014/110284; U.S. Pat. No. 8,673,018; US 2013/0142885; Ciobanu (2014); Jadalannagari (2014); US 2009/0198344.

As described herein, mineral coated scaffolds can be incubated in citric acid solution and silver nitrate solution to produce silver nanoparticles and microparticles on the mineral coating.

As described herein, the mineral coated scaffold can be incubated in citric acid solution. For example, the citric acid solution can be from 0.1 to 100 mM citric acid solution. As another example, the concentration of citric acid solution can be at least about 0.1 mM citric acid. As another example, the concentration of citric acid solution can be at least about 0.1 mM citric acid; at least about 0.2 mM citric acid; at least about 0.3 mM citric acid; at least about 0.4 mM citric acid; at least about 0.5 mM citric acid; at least about 0.6 mM citric acid; at least about 0.7 mM citric acid; at least about 0.8 mM citric acid; at least about 0.9 mM citric acid; at least about 1 mM citric acid; at least about 1.5 mM citric acid; at least about 2 mM citric acid; at least about 2.5 mM citric acid; at least about 3.0 mM citric acid; at least about 3.5 mM citric acid; at least about 4.0 mM citric acid; at least about 4.5 mM citric acid; at least about 5.0 mM citric acid; at least about 5.5 mM citric acid; at least about 6.0 mM citric acid; at least about 6.5 mM citric acid; at least about 7.0 mM citric acid; at least about 7.5 mM citric acid; at least about 8.0 mM citric acid; at least about 8.5 mM citric acid; at least about 9.0 mM citric acid; at least about 10 mM citric acid; at least about 15 mM citric acid; at least about 20 mM citric acid; at least about 25 mM citric acid; at least about 30 mM citric acid; at least about 35 mM citric acid; at least about 40 mM citric acid; at least about 45 mM citric acid; at least about 50 mM citric acid; at least about 55 mM citric acid; at least about 60 mM citric acid; at least about 65 mM citric acid; at least about 70 mM citric acid; at least about 75 mM citric acid; at least about 80 mM citric acid; at least about 85 mM citric acid; at least about 90 mM citric acid; at least about 95 mM citric acid; at least about; or 100 mM citric acid. It is understood that recitation of the above discrete values includes a range between each recited value.

As described herein, the concentration of citric acid solution can be about 0.1 mM citric acid; at least about 0.2 mM citric acid; about 0.3 mM citric acid; about 0.4 mM citric acid; about 0.5 mM citric acid; about 0.6 mM citric acid; about 0.7 mM citric acid; about 0.8 mM citric acid; about 0.9 mM citric acid; about 1 mM citric acid; about 1.5 mM citric acid; about 2 mM citric acid; about 2.5 mM citric acid; about 3.0 mM citric acid; about 3.5 mM citric acid; about 4.0 mM citric acid; about 4.5 mM citric acid; about 5.0 mM citric acid; about 5.5 mM citric acid; about 6.0 mM citric acid; about 6.5 mM citric acid; about 7.0 mM citric acid; about 7.5 mM citric acid; about 8.0 mM citric acid; about 8.5 mM citric acid; about 9.0 mM citric acid; about 10 mM citric acid; about 15 mM citric acid; about 20 mM citric acid; about 25 mM citric acid; about 30 mM citric acid; about 35 mM citric acid; about 40 mM citric acid; about 45 mM citric acid; about 50 mM citric acid; about 55 mM citric acid; about 60 mM citric acid; about 65 mM citric acid; about 70 mM citric acid; about 75 mM citric acid; about 80 mM citric acid; about 85 mM citric acid; about 90 mM citric acid; about 95 mM citric acid; about; or 100 mM citric acid. It is understood that recitation of the above discrete values includes a range between each recited value.

As described herein, the mineral coated scaffold can be incubated in citric acid solution for 0.1 hours to 40 hours. For example, the mineral coated scaffold can be incubated for 0.5 hours to 4 hours. It is understood that recitation of the above ranges includes discrete values within each recited range.

As described herein, the mineral coated scaffold can be incubated in citric acid solution for at least about 0.1 hours. For example, the mineral coated scaffold can be incubated in citric acid solution for at least about 0.1 hours; at least about 0.2 hours; at least about 0.3 hours; at least about 0.4 hours; at least about 0.5 hours; at least about 0.6 hours; at least about 0.7 hours; at least about 0.8 hours; at least about 0.9 hours; at least about 1 hours; at least about 1.1 hours; at least about 1.2 hours; at least about 1.3 hours; at least about 1.4 hours; at least about 1.5 hours; at least about 1.6 hours; at least about 1.7 hours; at least about 1.8 hours; at least about 1.9 hours; at least about 2 hours; at least about 2.1 hours; at least about 2.3 hours; at least about 2.4 hours; at least about 2.5 hours; at least about 2.6 hours; at least about 2.7 hours; at least about 2.8 hours; at least about 2.9 hours; at least about 3.0 hours; at least about 3.1 hours; at least about 3.2 hours; at least about 3.3 hours; at least about 3.4 hours; at least about 3.5 hours; at least about 3.6 hours; at least about 3.7 hours; at least about 3.8 hours; at least about 3.9 hours; at least about 4.0 hours; at least about 5 hours; at least about 5.5 hours; at least about 6.0 hours; at least about 6.5 hours; at least about 7.5 hours; at least about 8.0 hours; at least about 8.5 hours; at least about 9.0 hours; at least about 9.5 hours; at least about 10 hours; at least about 11 hours; at least about 12 hours; at least about 13 hours; at least about 14 hours; at least about 15 hours; at least about 16 hours; at least about 17 hours; at least about 18 hours; at least about 19 hours; at least about 20 hours; at least about 21 hours; at least about 22 hours; at least about 23 hours; at least about 24 hours; at least about 25 hours; at least about 26 hours; at least about 27 hours; at least about 28 hours; at least about 29 hours; at least about 30 hours; at least about 31 hours; at least about 32 hours; at least about 33 hours; at least about 34 hours; at least about 35 hours; at least about 36 hours; at least about 37 hours; at least about 38 hours; at least about 39 hours; or at least about 40 hours. It is understood that recitation of the above discrete values includes a range between each recited value.

As another example, the mineral coated scaffold can be incubated in citric acid solution for about 0.1 hours; about 0.2 hours; about 0.3 hours; about 0.4 hours; about 0.5 hours; about 0.6 hours; about 0.7 hours; about 0.8 hours; about 0.9 hours; about 1 hours; about 1.1 hours; about 1.2 hours; about 1.3 hours; about 1.4 hours; about 1.5 hours; about 1.6 hours; about 1.7 hours; about 1.8 hours; about 1.9 hours; about 2.0 hours; about 2.1 hours; about 2.3 hours; about 2.4 hours; about 2.5 hours; about 2.6 hours; about 2.7 hours; about 2.8 hours; about 2.9 hours; about 3.0 hours; about 3.1 hours; about 3.2 hours; about 3.3 hours; about 3.4 hours; about 3.5 hours; about 3.6 hours; about 3.7 hours; about 3.8 hours; about 3.9 hours; about 4.0 hours; about 5 hours; about 5.5 hours; about 6.0 hours; about 6.5 hours; about 7.5 hours; about 8.0 hours; about 8.5 hours; about 9.0 hours; about 9.5 hours; about 10 hours; about 11 hours; about 12 hours; about 13 hours; about 14 hours; about 15 hours; about 16 hours; about 17 hours; about 18 hours; about 19 hours; about 20 hours; about 21 hours; about 22 hours; about 23 hours; about 24 hours; about 25 hours; about 26 hours; about 27 hours; about 28 hours; about 29 hours; about 30 hours; about 31 hours; about 32 hours; about 33 hours; about 34 hours; about 35 hours; about 36 hours; about 37 hours; about 38 hours; about 39 hours; or about 40 hours. It is understood that recitation of the above discrete values includes a range between each recited value.

The citric acid-treated mineral-coated scaffolds can then be transferred to a silver nitrate solution to grow silver particles. Silver particles can cover the entire coated scaffold. The size of silver particles can be increased with longer silver nitrate incubation time and higher silver nitrate concentrations, whereas citric acid incubation time and concentration have not been shown to influence the silver particle size.

As described herein, silver particles can be synthesized on both citric acid-treated and non-citric-acid-treated mineral-coated scaffolds, because the size and morphology of the silver particles between these two groups can be the same. Silver carbonate and silver phosphate particles can be created locally on a mineral coated scaffold by the reaction of silver ions with carbonate or phosphate ions dissolved from CaP in a mineral coating.

As described herein, the time course release of silver which was prepared from different incubating conditions can be measured. The silver release from mineral coatings can continue for time periods ranging from 3 days to over 30 days, and the total quantity of released silver species can range from 0.7 µg to 75.4 µg per cm$^2$ of sample surface. The silver release can occur with nearly linear release kinetics in groups treated with citric acid, while the groups not treated with citric acid can show an initial burst release during the first two days. These release kinetics can be dictated by the different dissolution rates of CaP coatings in presence of adsorbed citric acid molecules. Burst release can pose a practical problem in the application of drug delivery systems, because it can occur in an unpredictable manner and may cause negative side effects due to overdose of the released drug. Citric acid treatment can help avoid burst release of silver species, and thereby prevent complications that may be related to silver overdose. The 4-hour incubation in citric acid solution can lead to more rapid release kinetics compared to 0.5 and 1 hour incubations. The silver release kinetics was not shown to be influenced by the citric acid concentration. This trend suggests that the amount of released silver can be dictated by the adsorbed citric acid and thus dissolution of mineral coatings. Increase of incubation time (e.g., 0.5 to 4 hr) in silver nitrate solution can result in a larger amount of silver released.

Similarly, higher concentrations of silver nitrate solution during growth of silver particles can lead to larger quantities of silver released over longer release periods. Taken together, these results can indicate that the dosage and timeframe of silver release could be readily controlled by varying the conditions during growth of silver salt particles on the mineral coated scaffold.

The antibacterial activity of released silver can be evaluated against a bacterial culture. For example, against *Staphylococcus* and gram-negative *Escherichia coli*. Media from silver-releasing CaP coatings can be added to bacterial suspensions in their exponential growth phase, and bacterial growth can be monitored by measuring optical density at 600 nm.

Silver released into the media can have antibacterial activity that is similar against *S. aureus* and *E. coli*. Silver released at a later time point can remain antimicrobially active. Because previous studies reported that citric acid can be effective to treat chronic wound infection by preventing colony formation of microorganism, the citric acid can also be beneficial to the antibacterial properties of the silver nanoparticle-incorporated mineral-coated scaffold.

As described herein, silver particles can cover the surface of the mineral coating or scaffold with at least about 1% coverage. For example, the silver particles can cover the surface of the mineral coating or scaffold with at least about 1% coverage; at least about 2% coverage; at least about 3% coverage; at least about 4% coverage; at least about 5% coverage; at least about 6% coverage; at least about 7% coverage; at least about 8% coverage; at least about 9% coverage; at least about 10% coverage; at least about 11% coverage; at least about 12% coverage; at least about 13% coverage; at least about 14% coverage; at least about 15% coverage; at least about 16% coverage; at least about 17% coverage; at least about 18% coverage; at least about 19% coverage; at least about 20% coverage; at least about 21% coverage; at least about 22% coverage; at least about 23% coverage; at least about 24% coverage; at least about 25% coverage; at least about 26% coverage; at least about 27% coverage; at least about 28% coverage; at least about 29% coverage; at least about 30% coverage; at least about 31% coverage; at least about 32% coverage; at least about 33% coverage; at least about 34% coverage; at least about 35% coverage; at least about 36% coverage; at least about 37% coverage; at least about 38% coverage; at least about 39% coverage; at least about 40% coverage; at least about 41% coverage; at least about 42% coverage; at least about 43% coverage; at least about 44% coverage; at least about 45% coverage; at least about 46% coverage; at least about 47% coverage; at least about 48% coverage; at least about 49% coverage; at least about 50% coverage; at least about 51% coverage; at least about 52% coverage; at least about 53% coverage; at least about 54% coverage; at least about 55% coverage; at least about 56% coverage; at least about 57% coverage; at least about 58% coverage; at least about 59% coverage; at least about 60% coverage; at least about 61% coverage; at least about 62% coverage; at least about 63% coverage; at least about 64% coverage; at least about 65% coverage; at least about 66% coverage; at least about 67% coverage; at least about 68% coverage; at least about 69% coverage; at least about 70% coverage; at least about 71% coverage; at least about 72% coverage; at least about 73% coverage; at least about 74% coverage; at least about 75% coverage; at least about 76% coverage; at least about 77% coverage; at least about 78% coverage; at least about 79% coverage; at least about 80% coverage; at least about 81% coverage; at least about 82% coverage; at least about 83% coverage; at least about 84% coverage; at least about 85% coverage; at least about 86% coverage; at least about 87% coverage; at least about 88% coverage; at least about 89% coverage; at least about 90% coverage; at least about 91% coverage; at least about 92% coverage; at least about 93% coverage; at least about 94% coverage; at least about 95% coverage; at least about 96% coverage; at least about 97% coverage; at least about 98% coverage; or at least about 99% coverage. It is understood that recitation of the above discrete values includes a range between each recited value.

As described herein, the silver particles can cover the surface of the mineral coating or scaffold with at least about 1% coverage; about 2% coverage; about 3% coverage; about 4% coverage; about 5% coverage; about 6% coverage; about 7% coverage; about 8% coverage; about 9% coverage; about 10% coverage; about 11% coverage; about 12% coverage; about 13% coverage; about 14% coverage; about 15% coverage; about 16% coverage; about 17% coverage; about 18% coverage; about 19% coverage; about 20% coverage; about 21% coverage; about 22% coverage; about 23% coverage; about 24% coverage; about 25% coverage; about 26% coverage; about 27% coverage; about 28% coverage; about 29% coverage; about 30% coverage; about 31% coverage; about 32% coverage; about 33% coverage; about 34% coverage; about 35% coverage; about 36% coverage; about 37% coverage; about 38% coverage; about 39% coverage; about 40% coverage; about 41% coverage; about 42% coverage; about 43% coverage; about 44% coverage; about 45% coverage; about 46% coverage; about 47% coverage; about 48% coverage; about 49% coverage; about 50% coverage; about 51% coverage; about 52% coverage; about 53% coverage; about 54% coverage; about 55% coverage; about 56% coverage; about 57% coverage; about 58% coverage; about 59% coverage; about 60% coverage; about 61% coverage; about 62% coverage; about 63% coverage; about 64% coverage; about 65% coverage; about 66% coverage; about 67% coverage; about 68% coverage; about 69% coverage; about 70% coverage; about 71% coverage; about 72% coverage; about 73% coverage; about 74% coverage; about 75% coverage; about 76% coverage; about 77% coverage; about 78% coverage; about 79% coverage; about 80% coverage; about 81% coverage; about 82% coverage; about 83% coverage; about 84% coverage; about 85% coverage; about 86% coverage; about 87% coverage; about 88% coverage; about 89% coverage; about 90% coverage; about 91% coverage; about 92% coverage; about 93% coverage; about 94% coverage; about 95% coverage; about 96% coverage; about 97% coverage; about 98% coverage; or about 99% coverage. It is understood that recitation of the above discrete values includes a range between each recited value.

Although the embodiments described herein describe single layers of coatings, more than one coating or application of the mineral coating, DBM, or silver particles may be applied.

Buffers

The buffer, as described herein, can be used in the modified simulated body fluid. The buffer, as described herein, can be any conventional buffer. A buffer can be as described in U.S. application Ser. Nos. 13/407,441; 13/879,178; and 13/036,470 and are incorporated by reference.

For example, the buffer can be a saline buffer. As another example, the buffer can be Tris. Tris can be tris-buffered saline (TBS). Tris can be Tris HCl. As another example, the buffer can be PBS. PBS can be DPBS. As another example a buffer can be a mixture including citric acid, monopotassium phosphate, boric acid, or diethyl barbituric acid. As another example a buffer can be TAPS, Bicine, Tricine, TAPSO, HEES, TES, MOPS, PIPES, Cacodylate, SSC, MES, or succinic acid.

The buffer, as described herein, can be at any conventional concentration. For example, the concentration of buffer in the simulated body fluid can be at least about 1 mM buffer. As another example, the concentration of buffer in the simulated body fluid can be at least about 2 mM buffer; at least about 3 mM buffer; at least about 4 mM buffer; at least about 5 mM buffer; at least about 6 mM buffer; at least about 7 mM buffer; at least about 8 mM buffer; at least about 9 mM buffer; at least about 10 mM buffer; at least about 11 mM buffer; at least about 12 mM buffer; at least about 13 mM buffer; at least about 14 mM buffer; at least about 15 mM buffer; at least about 16 mM buffer; at least about 17 mM buffer; at least about 18 mM buffer; at least about 19 mM buffer; at least about 20 mM buffer; at least about 21 mM buffer; at least about 22 mM buffer; at least about 23 mM buffer; at least about 24 mM buffer; at least about 25 mM buffer; at least about 26 mM buffer; at least about 27 mM buffer; at least about 28 mM buffer; at least about 29 mM buffer; at least about 30 mM buffer; at least about 31 mM buffer; at least about 32 mM buffer; at least about 33 mM buffer; at least about 34 mM buffer; at least about 35 mM buffer; at least about 36 mM buffer; at least about 37 mM buffer; at least about 38 mM buffer; at least about 39 mM buffer; at least about 40 mM buffer; at least about 50 mM buffer; at least about 60 mM buffer; at least about 70 mM buffer; at least about 80 mM buffer; at least about 90 mM buffer; at least about 100 mM buffer; at least about 110 mM buffer; at least about 120 mM buffer; at least about 130 mM buffer; at least about 140 mM buffer; at least about 150 mM buffer; at least about 160 mM buffer; at least about 170 mM buffer; at least about 180 mM buffer; at least about 190 mM buffer; at least about 120 mM buffer; at least about 130 mM buffer; at least about 140 mM buffer; at least about 150 mM buffer; at least about 160 mM buffer; at least about 170 mM buffer; at least about 180 mM buffer; at least about 190 mM buffer; or at least about 200 mM buffer. It is understood that recitation of the above discrete values includes a range between each recited value.

As another example, the concentration of buffer in the simulated body fluid can be about 1 mM buffer; about 2 mM buffer; about 3 mM buffer; about 4 mM buffer; about 5 mM buffer; about 6 mM buffer; about 7 mM buffer; about 8 mM buffer; about 9 mM buffer; about 10 mM buffer; about 11 mM buffer; about 12 mM buffer; about 13 mM buffer; about 14 mM buffer; about 15 mM buffer; about 16 mM buffer; about 17 mM buffer; about 18 mM buffer; about 19 mM buffer; about 20 mM buffer; about 21 mM buffer; about 22 mM buffer; about 23 mM buffer; about 24 mM buffer; about 25 mM buffer; about 26 mM buffer; about 27 mM buffer; about 28 mM buffer; about 29 mM buffer; about 30 mM buffer; about 31 mM buffer; about 32 mM buffer; about 33 mM buffer; about 34 mM buffer; about 35 mM buffer; about 36 mM buffer; about 37 mM buffer; about 38 mM buffer; about 39 mM buffer; about 40 mM buffer; about 50 mM buffer; about 60 mM buffer; about 70 mM buffer; about 80 mM buffer; about 90 mM buffer; about 100 mM buffer; about 110 mM buffer; about 120 mM buffer; about 130 mM buffer; about 140 mM buffer; about 150 mM buffer; about 160 mM buffer; about 170 mM buffer; about 180 mM buffer; about 190 mM buffer; about 120 mM buffer; about 130 mM buffer; about 140 mM buffer; about 150 mM buffer; about 160 mM buffer; about 170 mM buffer; about 180 mM buffer; about 190 mM buffer; or about 200 mM buffer. It is understood that recitation of the above discrete values includes a range between each recited value.

A buffer can be held at any pH conventional in the art. For example, a buffer can have a pH in the range of 2 to 11. As another example, a buffer can have a pH value of at least about 2. As another example, a buffer can have a pH value of at least about 2; a pH value of at least about 2.5; a pH value of at least about 3; a pH value of at least about 3.5; a pH value of at least about 4; a pH value of at least about 4.5; a pH value of at least about 5; a pH value of at least about 5.5; a pH value of at least about 6; a pH value of at least about 6.1; a pH value of at least about 6.2; a pH value of at least about 6.3; a pH value of at least about 6.4; a pH value of at least about 6.5; a pH value of at least about 6.6; a pH value of at least about 6.7; a pH value of at least about 6.8; a pH value of at least about 6.9; a pH value of at least about 7; a pH value of at least about 7.1; a pH value of at least about 7.2; a pH value of at least about 7.3; a pH value of at least about 7.4; a pH value of at least about 7.5; a pH value of at least about 7.6; a pH value of at least about 7.7; a pH value of at least about 7.8; a pH value of at least about 7.9; a pH value of at least about 8; a pH value of at least about 8.5; a pH value of at least about 9; a pH value of at least about 9.5; a pH value of at least about 10; a pH value of at least about 11. It is understood that recitation of the above discrete values includes a range between each recited value.

As another example, a buffer can have a pH value of about 2; a pH value of about 2.5; a pH value of about 3; a pH value of about 3.5; a pH value of about 4; a pH value of about 4.5; a pH value of about 5; a pH value of about 5.5; a pH value of about 6; a pH value of about 6.1; a pH value of about 6.2; a pH value of about 6.3; a pH value of about 6.4; a pH value of about 6.5; a pH value of about 6.6; a pH value of about 6.7; a pH value of about 6.8; a pH value of about 6.9; a pH value of about 7; a pH value of about 7.1; a pH value of about 7.2; a pH value of about 7.3; a pH value of about 7.4; a pH value of about 7.5; a pH value of about 7.6; a pH value of about 7.7; a pH value of about 7.8; a pH value of about 7.9; a pH value of about 8; a pH value of about 8.5; a pH value of about 9; a pH value of about 9.5; a pH value of about 10; a pH value of about 11. It is understood that recitation of the above discrete values includes a range between each recited value.

As another example, a buffer can have a pH value that is physiologically relevant. A buffer can have a pH value of about 6 to about 8.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to a scaffold, a modified simulated body fluid solution, or any other agent as described above. Such packaging of the components separately can, if desired, be presented in a pack or dispenser device which can contain one or more unit dosage forms containing the composition. The pack can, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Mineral Coating

The following example describes the mineralization of a polycaprolactone (PCL) scaffold.

A PCL scaffold was hydrolyzed in a 1.0 M NaOH solution for 60 minutes to produce a hydrolyzed, carboxylic acid-rich surface. After hydrolysis of the PCL scaffold, a bone mineral coating was formed by immersion of a PCL scaffold in modified simulated body fluid (mSBF) and incubated.

The mSBF in this example was an inorganic solution having a similar composition to human plasma but with double the concentration of calcium and phosphate to enhance mineral growth, without organic components, at physiological conditions, and continuous rotations. The mSBF solution was prepared according to the following. The following reagents were added to $ddH_2O$ in the order shown: 141 mM NaCl, 4.0 mM KCl, 1.0 mM $MgCl_2$, 0.5 mM $MgSO_4$, 4.2 mM $NaHCO_3$, 20 mM Tris, 5 mM $CaCl_2$, and 2.0 mM $KH_2PO_4$. The solution was slowly heated to 37° C. and was adjusted to a final pH of 6.8 using HCl and/or NaOH buffer solutions.

Figure 1B:
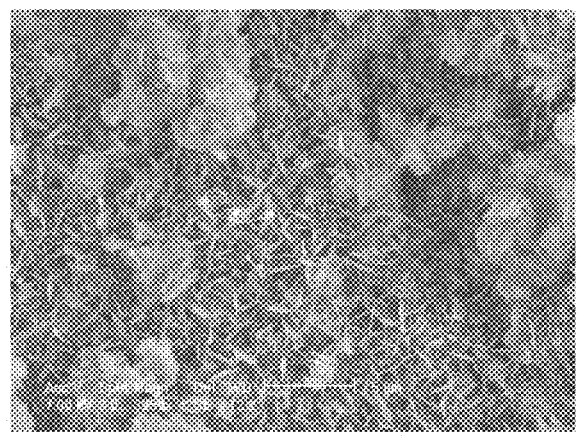

The incubation period was varied from 5 to 14 days. The mSBF solution was renewed every two days in order to maintain consistent ionic strength throughout the coating process. The apatite (a group of calcium phosphates including bone mineral and the main inorganic constituent of bones and teeth similar to hydroxyapatite) was nucleated and grown on the surface of the PCL scaffold to form an integral part of the coated PCL scaffold (see e.g., FIG. 1A-B). The mechanism for mineral nucleation and growth on PCL is thought to be based on the interaction of carboxylate ions and hydroxyl groups on the hydrolyzed PCL surface with calcium- and phosphate-rich nuclei in mSBF solution. This mineral growth process is thought to mimic natural biomineralization processes and results in a mineral coating that is similar in structure (plate-like nanostructure) and composition (carbonate-substituted, calcium-deficient hydroxyapatite phase) to human bone mineral. Ca-deficient HA was measured by Ca/P ratio. Chemicals for mSBF preparation were powder reagent grade chemicals. Water used was in accordance with ISO3696:1987, grade 2.

After mineral coating, the scaffold was rinsed for 15 minutes in $ddH_2O$ to remove residual salts and was freeze dried overnight in a lyophilizer at a temperature of −40° C., under vacuum.

Example 2: Coating Specifications

The following example describes the coating specifications.

The assessment of mineral formation was performed by determining the change in mass after coating compared with the initial mass (before coating).

Conditions were found to achieve a desired bone mineral coating on implants (see e.g., TABLE 1).

TABLE 1

Parameters for bone mineral coating on implants
Coating Specification (Coating alone)

| Property | Description | Analytical Method |
|---|---|---|
| Chemical composition and concentration (%) | 97% Hydroxyapatite 3% Octacalcium phosphate | XRD |
| Ca/P ratio after heat treatment at 1000° C., According to ISO 13779-2 | $1.67 \leq Ca/P \leq 1.76$ | XRD |
| Crystalline phase | Hydroxyapatite and octacalcium phosphate | XRD (2θ in the range of 15-35°, specifically at 25.8°, 28.1°, 28.9°, 31.8°, and 32.1°) and FTIR (peaks in the 1400-1500 $cm^{-1}$ region (for carbonate peaks) and 900-1100 $cm^{-1}$ region (for phosphate peaks) |
| % Crystallinity | 96.5% | XRD |
| Porosity (%) | 20-28%* | SEM/Image J |
| Pore size (nm) | 100-350 nm* | SEM/Image J |
| Heavy metal trace element (ppm) as ref. in ISO 13779-3 | Arsenic (As) < 2.1 ppm Cadmium (Cd) < 0.1 ppm Lead (Pb) < 0.1 ppm Mercury (Hg) < 4.7 ppm | EDX for element identification, ICP for element concentrations |

TRS- SP0019-01 Bone Mineral Coating,
*Porosity and pore size studies of C-BVF

Example 3: Coating Dissolution

The following example describes coating dissolution rate in various medium conditions. It was shown that the phosphate buffer provided decreased coating dissolution compared to Tris.

Figure 2A:
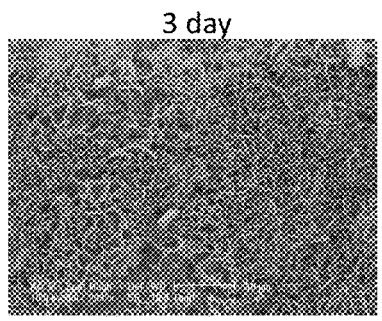
FIG. 2A-2F are a series of micrographs depicting the coating surfaces on a PCL scaffold after incubation with DPBS.
Figure 2B:
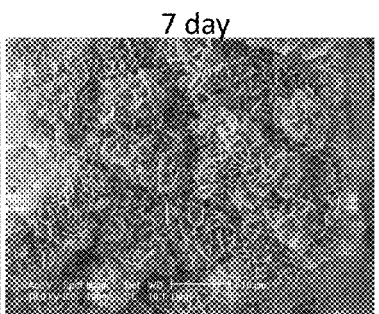
Figure 2C:
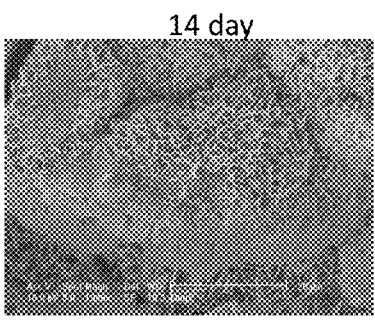
Figure 2D:
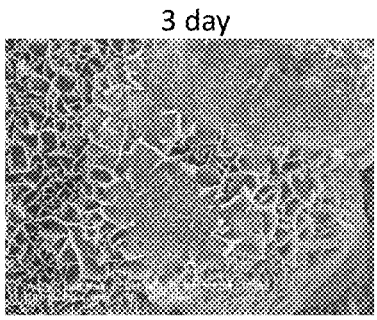
Figure 2E:
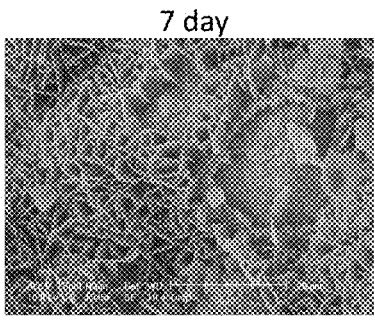
Figure 2:
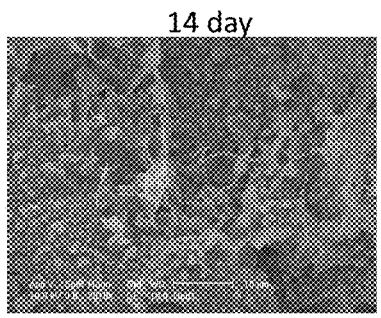
Figure 3A:
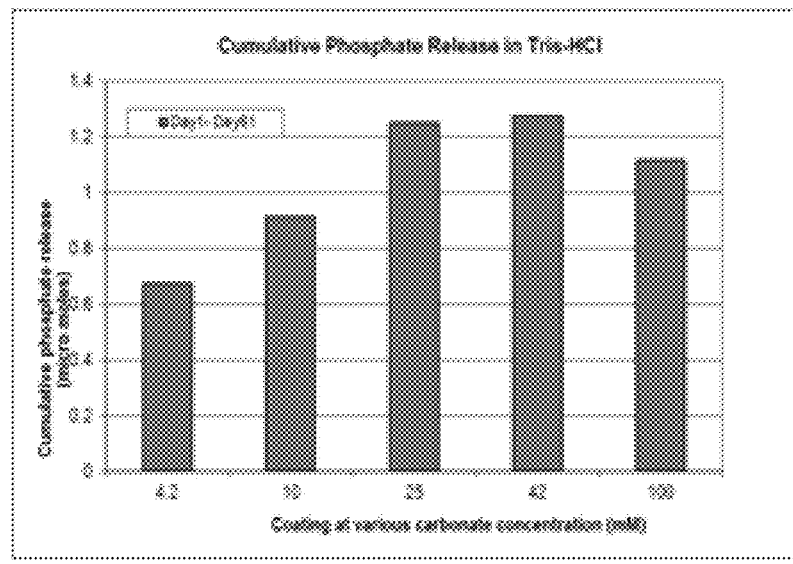
FIG. 3A-3B are a series of bar graphs depicting the amount of cumulative release of phosphate or calcium.
Figure 3B:
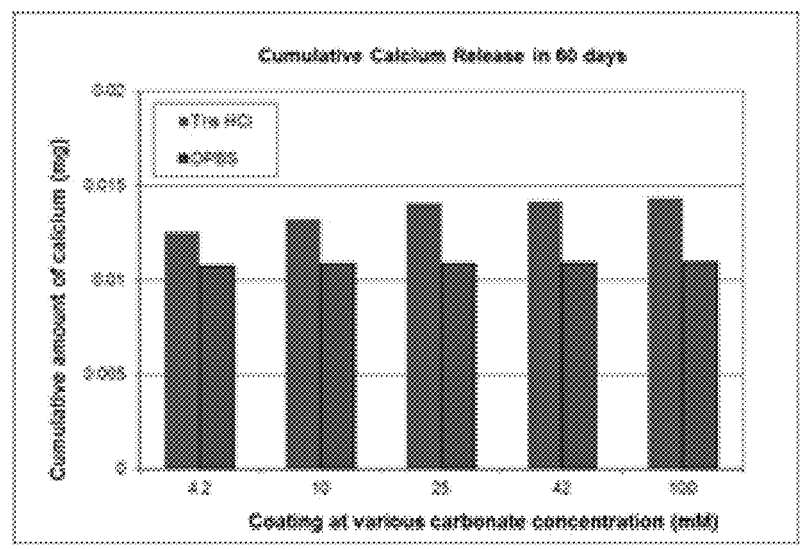

Under simulated physiological conditions, coating dissolution occurred when the environment was undersaturated with calcium and phosphate ions. This was the case for Tris-HCl. But, for the saline buffer, DPBS had phosphate ions in the solution that were believed to be either blocking the dissolution of phosphate ions from the coating or competing against each other for re-precipitation, resulting in the slower rate of dissolution. A series of SEM micrographs (see e.g., FIG. 2) taken at different time points and the amount of calcium (see e.g., FIG. 3) in the release medium support the above hypothesis.

Example 4: Coating PCL Devices

The following example describes the details, proper instructions and safety precautions for coating polycaprolactone (PCL) medical devices via modified simulated body fluid (mSBF) incubation, wherein the coating procedure applies to any size PCL medical device.

The modified simulated body fluid (mSBF) in this Example is a solution with a similar composition of human plasma but double the concentration of calcium and phosphate. The mSBF solution described in this Example is used for incubating materials and nucleating an apatite-like mineral.

Materials.

Reagents and their respective desired concentration in final solution is as follows. Hydrolysis Reagents: NaOH (1.0 M). Coating Reagents: NaCl (141.0 mM); KCl (4.0 mM); $MgSO_4$ (0.5 mM); $MgCl_2$ (1.0 mM); $NaHCO_3$ (4.2 mM); Tris(hydroxymethyl) aminomethane (20.2 mM); $CaCl_2$ (5.0 mM); $KH_2PO_4$ (2.0 mM). Deionized ultra filtered (DIUF) water. Buffers: 2N HCl; 2N NaOH. Hot plate/stirrer; Magnetic stir bar; Spatula; Weighing paper or weigh boat; Analytical mass balance; pH meter; Glass beakers capable of holding desired volume of mSBF; and 37° C. and 5% $CO_2$ Incubator. Rotating system: Labquake shaker system (for any container size up to 175 mL); Large coating system (for coating large device, see e.g., TABLE 2).

TABLE 2

Coating matrix using large coating system.

| | Description | Example | |
|---|---|---|---|
| Sample size (dimensions in mm) | X ≥ 30 mm × 30 mm × 50 mm; Mass ≥ 3500 mg | Pig sleeve (80 × 45 × 25 mm) | Degradation disc w. handle (35 dia × 5 mm) |
| Type of container | Custom made device for large coating system | Large coating system | Large coating system |
| No. of sample/ container | 10-100, due to the large volume of mSBF used we need to maximize the no. of sample per coating duration | 10 | 85 |

TABLE 2-continued

Coating matrix using large coating system.

| | Description | Example | |
|---|---|---|---|
| Volume of mSBF (gallon) | Working volume of 1.5-5 gallons | 3.0 gallons | 2.75 gallons |
| Frequency of changing mSBF (day) | 3 days | 3 days | 3 days |
| Coating duration (day) | 8-14 days, depending on the size and no. of sample | 10 days | 8 days |
| pH adjusting | Daily | Daily | Daily |

Hydrolysis Preparation.

Hydrolysis preparation includes determining the desired volume of 1M NaOH. See TABLE 3 for desired volume based on device size and weight.

TABLE 3

Hydrolysis matrix.

| | | | | |
|---|---|---|---|---|
| Sample size (dimensions in mm) and/or mass (mg) | 10 mm × 10 mm × 10 mm ≤ X, mass ≤ 250 mg | 10 mm × 10 mm × 10 mm < X < 25 mm × 25 mm × 5 mm; mass ≤ 2000 mg | 10 mm × 10 mm × 10 mm < X < 25 mm × 25 mm × 10 mm; mass ≤ 3500 mg | X ≥ 25 mm × 25 mm × 25 mm |
| Type of container | 50 mL conical tube | 50 mL conical tube | 175 mL conical tube | Depends on the size of sample |
| No. of sample/ container | 10-30, total sample volume occupied ≤ ⅓ total volume of container | 2-20, total sample volume occupied ≤ ⅓ total volume of container | 5-45, total sample volume occupied ≤ ⅓ total volume of container | Depends on the size of sample and selected container |
| Volume of 1M NaOH (mL) | 50 mL | 50 mL | 150 mL | Depends on the size of sample and selected container |
| Example | Test cube (6 × 6 × 6 mm), Monkey pin (10 × 5 × 3 mm), Rabbit plate (10 × 5 × 5 mm) | Porous cylinder (7 dia × 16 mm), Human module (20 × 20 × 12 mm), Monkey mandible (30 × 14 × 10 mm) | Porous cylinder (7 dia × 16 mm), Porous block (25 × 25 × 6), Monkey mandible (30 × 14 × 10 mm) | Pig module (35 × 30 × 10 mm), Pig sleeve (80 × 45 × 25 mm), Human sleeve (90 × 20 × 15 mm) |

Determination of the mass of solid state NaOH is required to prepare a 1M NaOH solution. Sample Calculation:

Desired volume of 1M NaOH: 400 mL
Required mass of solid state NaOH:

$$m_{NaOH} = [NaOH], \frac{mol}{L} * Vol_{NaOH}, mL * MW_{NaOH}$$

$$m_{NaOH} = \frac{1 \text{ mol}}{L} * 0.4 \text{ L} * \frac{40 \text{ g}}{\text{mol}} = 16 \text{ g NaOH}$$

Place hot plate/stirrer and analytical balance on rigid and leveled surface.

Coating Preparation.

Determine the desired volume of mSBF. See TABLE 2 and TABLE 4 for desired volume based on device size and weight. Note that for larger PCL devices, the mSBF may need to be prepared in several batches; if so, determine the desired volume of the batch. Determine the mass of each reagent needed to reach the desired concentration of each reagent (as listed above) in the batch volume.

TABLE 4

Coating matrix.

| | | | |
|---|---|---|---|
| Sample size (dimensions in mm) and/or mass (mg) | 10 mm × 10 mm × 10 mm ≤ X; mass ≤ 250 mg | 10 mm × 10 mm × 10 mm < X < 25 mm × 25 mm × 90 mm; mass ≤ 7500 mg | 10 mm × 10 mm × 10 mm < X < 35 mm × 35 mm × 50 mm; mass ≤ 10,000 mg |
| Type of container | 15 mL conical tube | 50 mL conical tube | 175 mL conical tube |

TABLE 4-continued

Coating matrix.

| No. of sample/container | 1-10, total sample volume occupied < ½ total volume of container | 1-15, total sample volume occupied < ½ total volume of container | 1-5, total sample volume occupied < ½ total volume of container |
|---|---|---|---|
| Volume of mSBF (mL) | 15 mL | 50 mL | 175 mL |
| Frequency of changing mSBF (days) | 2 days | 2 days | 2 days |
| Coating duration (days) | 8 days | 8 days | 8 days |
| pH adjusting | None | None | None |
| Example | Test cube (6 × 6 × 6 mm), Monkey pin (10 × 5 × 3 mm), Rabbit plate (10 × 5 × 5 mm) | Porous cylinder (7 dia × 16 mm), Human module (20 × 20 × 12 mm), Monkey mandible (30 × 14 × 10 mm), Human sleeve (90 × 20 × 15 mm) | Pig module (35 × 30 × 10 mm), Disc (35 dia × 5 mm) |

Sample Calculation:
Desired volume of mSBF: 500 mL mSBF
Required mass of reagent #1 (e.g. NaCl, 141 mM)

$$m_{NaCl} = [NaCl],\frac{mmol}{ml} * Vol_{mSBF}, ml * MW_{NaCl}$$

$$m_{NaCl} = \frac{141 \times 10^{-3}\,\text{mmol}}{\text{ml}} * 500\,\text{ml} * \frac{58.4\,\text{mg}}{\text{mmol}} = 4120\,\text{mg}$$

Place hot plate/stirrer and analytical balance on rigid and leveled surface. Check that the incubator is maintaining a 37° C. temperature and a 5% $CO_2$ level.

Check that the pH meter has been recently calibrated. If it has not been calibrated within the past 2 weeks, calibrate it according to the manufacturer's instructions.

Hydrolysis.

Measure the desired volume of DIUF water in an appropriately sized beaker. Place beaker on the hot plate/stirrer. Add magnetic stir bar to the DIUF water. Set the stirrer between settings 5 and 10, depending on the volume of DIUF water. Using a spatula and weighing paper or weigh boat, weigh the required amount of NaOH on an analytical mass balance. Add the reagent to the beaker with the DIUF water. Stir continuously until completely dissolved. Add 1M NaOH to PCL devices. Hydrolyze the PCL devices in the 1M NaOH for 1 hour, rotating the container in a circular motion during hydrolysis. Make sure that the 1M NaOH covers the entire surface of the PCL device during hydrolysis. After hydrolysis is complete, remove 1M NaOH from the container with the PCL devices. Rinse the PCL devices in DIUF water for 15 minutes. PCL devices ready for coating.

Coating.

Measure the desired volume of DIUF water in an appropriately sized beaker. Place beaker on the hot plate/stirrer. Add magnetic stir bar to the DIUF water. Set the stirrer between settings 5 and 10, depending on the volume of DIUF water. Preheat the DIUF water by setting the hot plate to ~40° C. (or setting 2-4). [Note: slowly heat the water from room temperature as reagents are added, and if 37° C. is reached, lower the heat setting to maintain the temperature of the water.] Using a spatula and weighing paper or weigh boat, weigh the required amount of reagent #1 (NaCl) on an analytical mass balance. Add the reagent to the beaker with the preheated DIUF water. While the solution is prepared, stir continuously. Wipe the spatula with ethanol or methanol after each use. Repeat for all of the reagents in order (as listed in Reagents). Add the reagents one at a time, ensuring that each reagent is fully dissolved before the next one is added. The temperature of the DIUF water should be between 24-26° C. while reagents are being added, with the DIUF water slowly heated to a temperature between 28-32° C. by the time all reagents are added. Note: It is normal for the mSBF solution to become basic (pH ~9) after addition of tris(hydroxymethyl) aminomethane and to become cloudy after the addition of $CaCl_2$.

Measure the pH of the solution using the pH meter. Buffer the solution to pH=6.8±0.1 using 2N HCl and 2N NaOH. Start buffering with 2N HCl as the resulting solution is basic (pH 8-9). When the pH falls to ~7.5, the solution will start to become clear. If HCl is added in excess and the pH falls below 6.8±0.1, use NaOH to adjust the pH to 6.8±0.1. While buffering the mSBF solution, continuously stir the solution and maintain the temperature at 37° C. Slowly heat the solution to 37° C. (if the solution has not yet reached 37° C. at the end of the buffering process). Keep checking the pH and the temperature for stability. Repeat until the desired volume is reached. mSBF should be stored in the 37° C. incubator until use. Adjust the pH of the final bulk volume to 6.8±0.1. Add mSBF solution to PCL devices for coating. Incubate the PCL devices in the 37° C. incubator, rotating the container in a circular motion during incubation. Make sure that the mSBF covers the entire surface of the PCL device during incubation. See TABLE 2 and TABLE 4 for coating duration, frequency of changing the mSBF solution, and pH adjustment (if necessary).

After incubation is complete, remove mSBF from the container with the PCL devices. Rinse the PCL devices in DIUF water for 15 minutes. Remove the DIUF water from the container with the PCL devices. Freeze the PCL devices in a −20° C. freezer. Lyophilize the frozen PCL devices. PCL devices ready for sterilization.

Special Precautions.

Wear latex gloves while handling all chemicals, solutions, and/or instruments.

If the mSBF solution turns cloudy during incubation before 2 (or 3 days for large coating system set up), change the solution as soon as possible.

Care and Maintenance of Equipment.

Daily: Calibrate the analytical mass balance to ensure accuracy of weighed reagents. Weekly: Check the status of the $CO_2$ levels in the incubator. Replace $CO_2$ tank(s) as needed according to manufacturer's instructions. Every two weeks: Calibrate the pH meter according to the manufacturer's instructions.

Example 5: Surface Pre-Treatments of Titanium Sample Prior Coating

The following example describes the details, proper instructions, and safety precautions for pretreating titanium samples.

Using 5 M NaOH. (a) Each step below need to be performed in a certified chemical hood and (b) volume of pre-treatment solution depends on size and shape of titanium samples, multiple samples may be pre-treated in the same container.

Very slowly add NaOH pellets (Fisher Scientific Lot #115786) to stirring deionized ultra-filtered (DIUF) water (Fisher Lot #140300) in a glass beaker to make 5 M NaOH solution. Keep beaker on stirrer in hood with stirrer on 'low'. Be mindful of fumes and rising temperatures—further slow down if excessive heating occurs. Let the solution stands for several minutes to cool down. Place Ti sample in clean glass beaker, pour NaOH solution in, cover the beaker with parafilm. Place beaker in sonicator for 1 hr. Keep monitoring sample during sonicator process, take note for the volume of bubbles rising. Take Ti sample out, place it in another beaker with DIUF and leave on shaker for 15 min. Blot dry with paper towel, sample is now ready for coating process.

Using Piranha solution (conc. $H_2SO_4$+30% $H_2O_2$). Each step below is performed in a certified chemical hood. Volume of pre-treatment solution depends on size and shape of titanium samples, multiple samples may be pre-treated in the same container. Add $H_2SO_4$ (Sigma Aldrich Lot # SHBB3339V) to a clean glass beaker in the hood. Very slowly add 30% $H_2O_2$ (Fisher Scientific Lot #102727) to $H_2SO_4$. The reaction can be explosive and is highly exothermic, proceed very slowly and with caution. Place Ti sample in clean glass beaker, carefully pour piranha solution in. Monitor sample for 5-20 minutes; observe for volume of bubbles rising. Immediately stop the reaction if there is any brownish color of sample/solution appear and take sample out.

Take Ti sample out quickly with forceps, rinse with copious amount of DIUF, then place in DIUF on shaker for 15 min. Blot dry with paper towel, sample is now ready for coating process.

Coating Process.

After pre-treatment, each sample was coated for 4-6 days in coating solution (1× mSBF) at 37° C. with solution refreshed daily.

Example 6: Coating Enhances Osseointegration of Metal Surfaces

The unique nanoscale architecture of the coating may be applied to virtually any underlying implant surface (e.g., plasma sprayed titanium), reaching all pores of complex scaffolds and improving upon the degree of osseointegration into micro-structured implants.

Figure 4A:
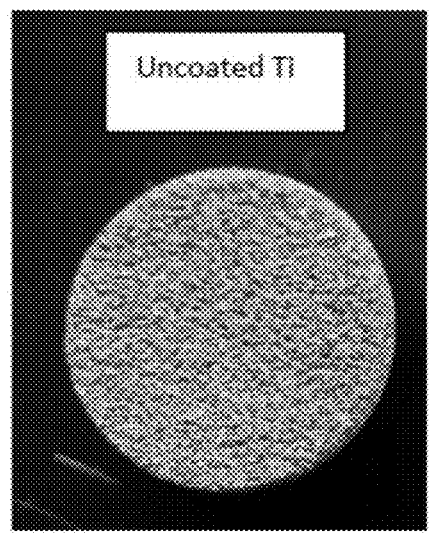
FIG. 4A-4B are a series of micrographs depicting the surfaces on a titanium (Ti) scaffold.
Figure 4B:
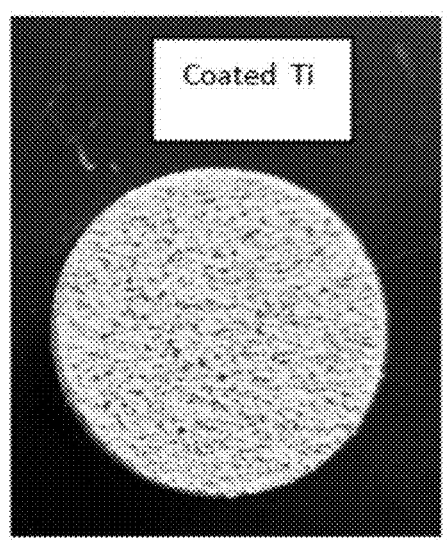
Figure 5A:
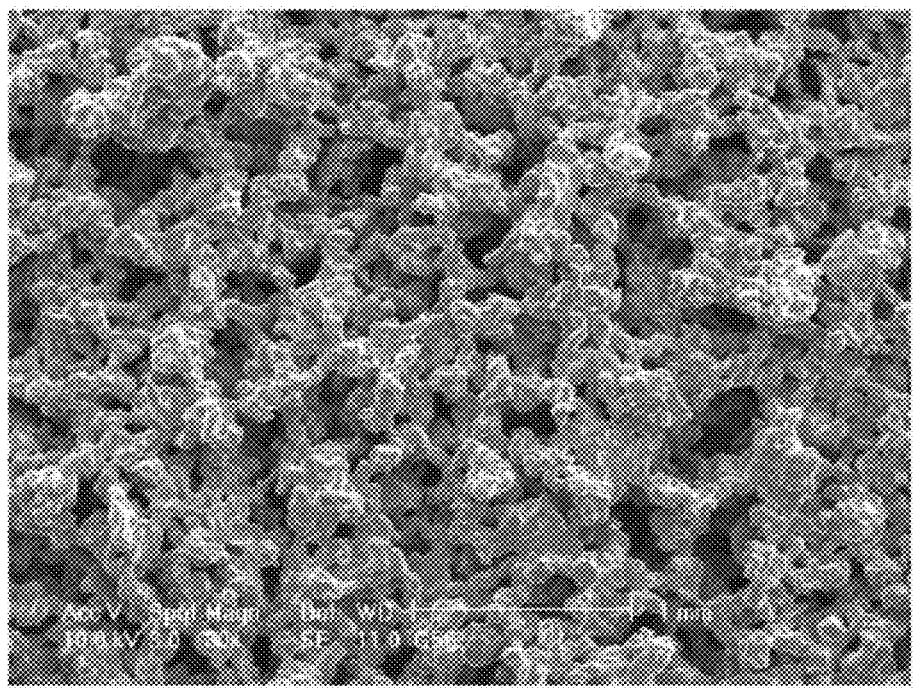
FIG. 5A-5B are a series of micrographs depicting the uncoated surfaces on a Ti scaffold.
Figure 5B:
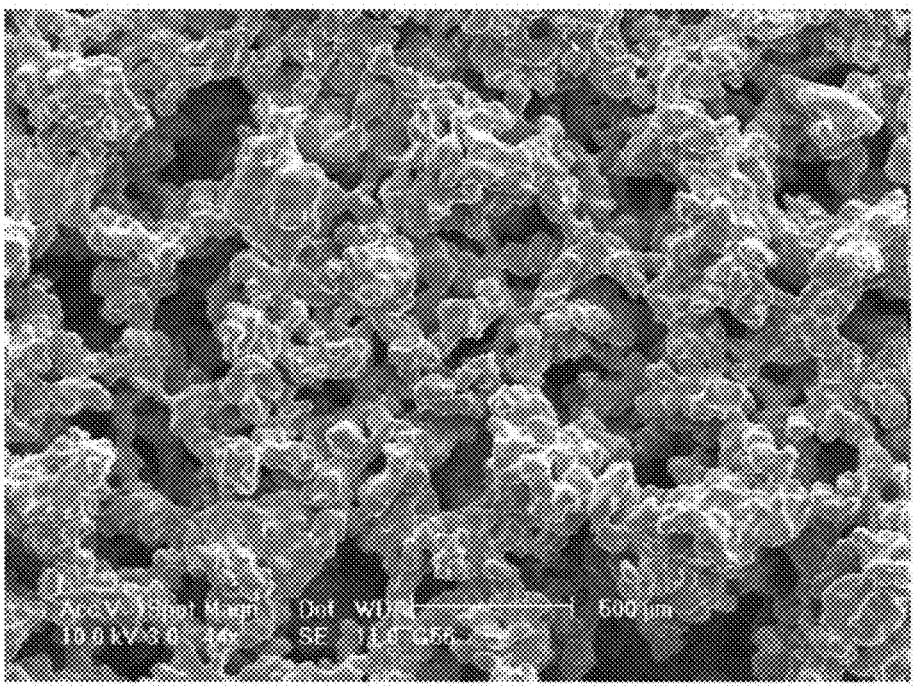
Figure 5C:
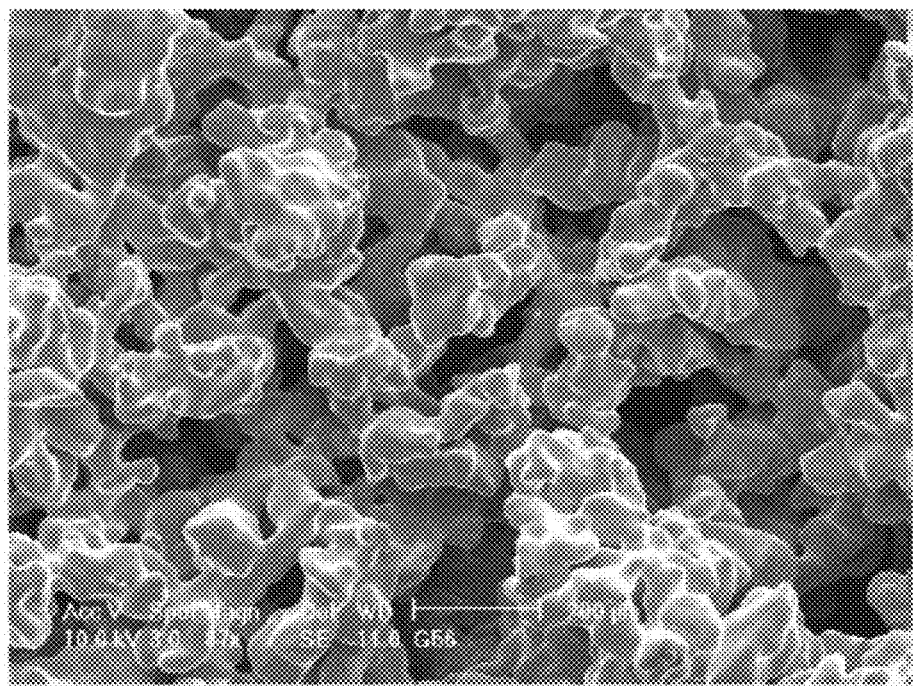
FIG. 5C shows SEM micrographs of the uncoated Ti (scale bar=200 µm).
Figure 5D:
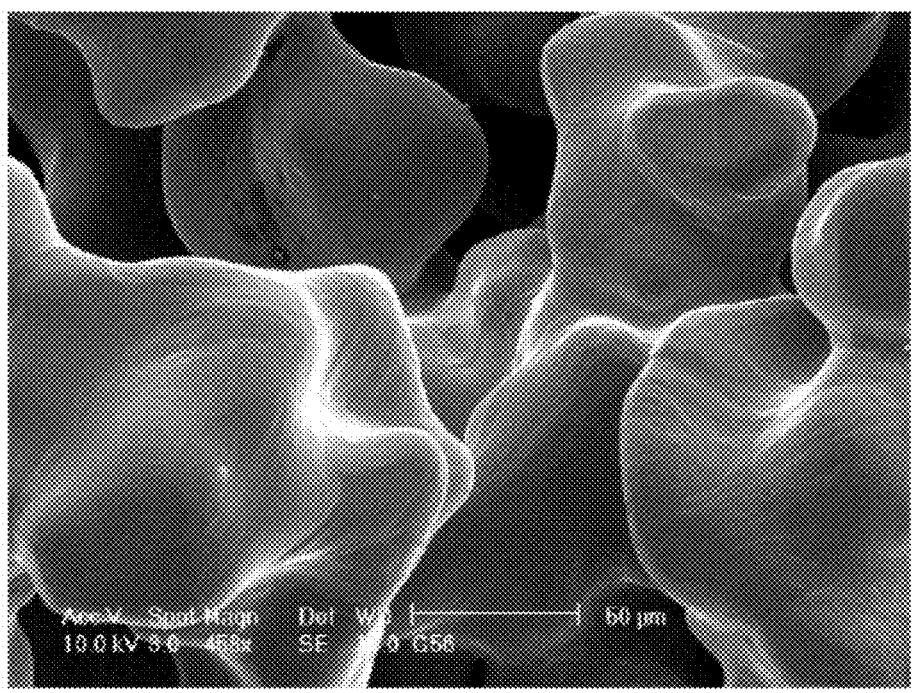
FIG. 5D shows SEM micrographs of the uncoated Ti (scale bar=50 µm).
Figure 6A:
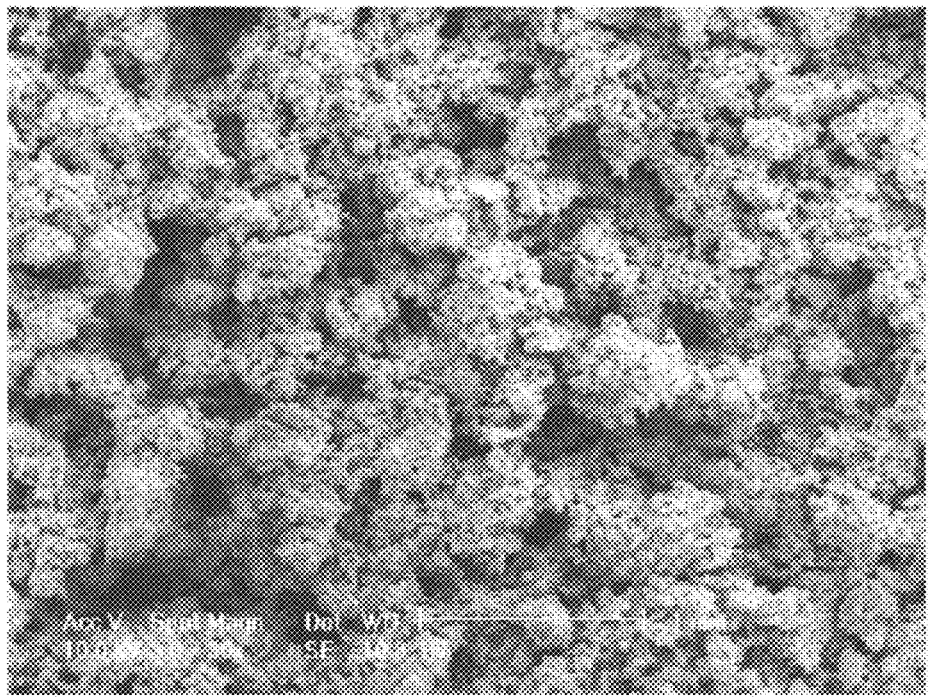
FIG. 6A-6D are a series of micrographs depicting the coated surfaces on a Ti scaffold.
Figure 6B:
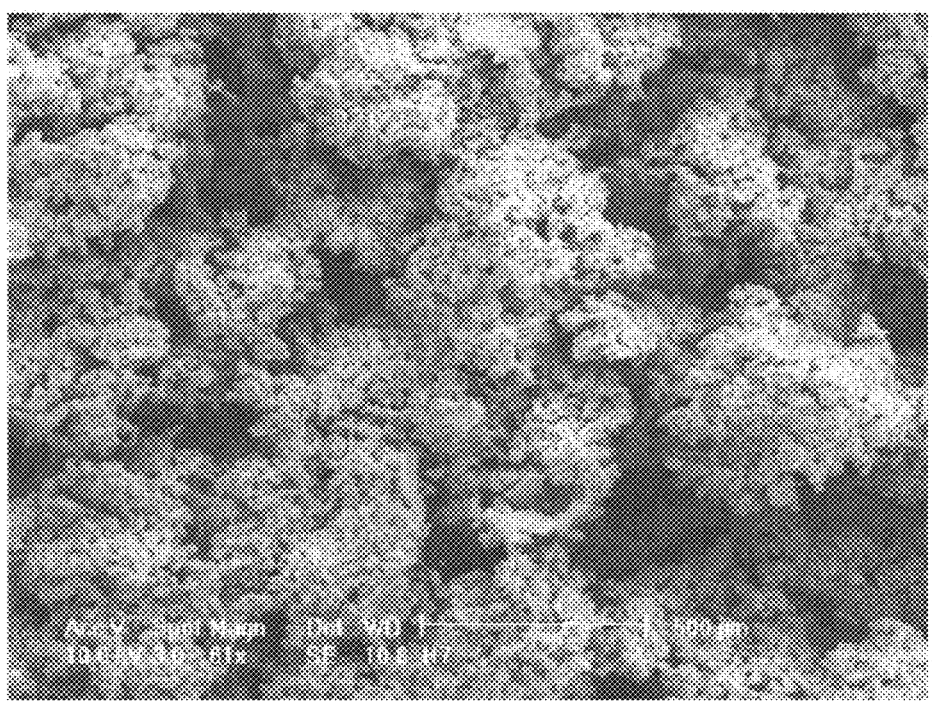
Figure 6C:
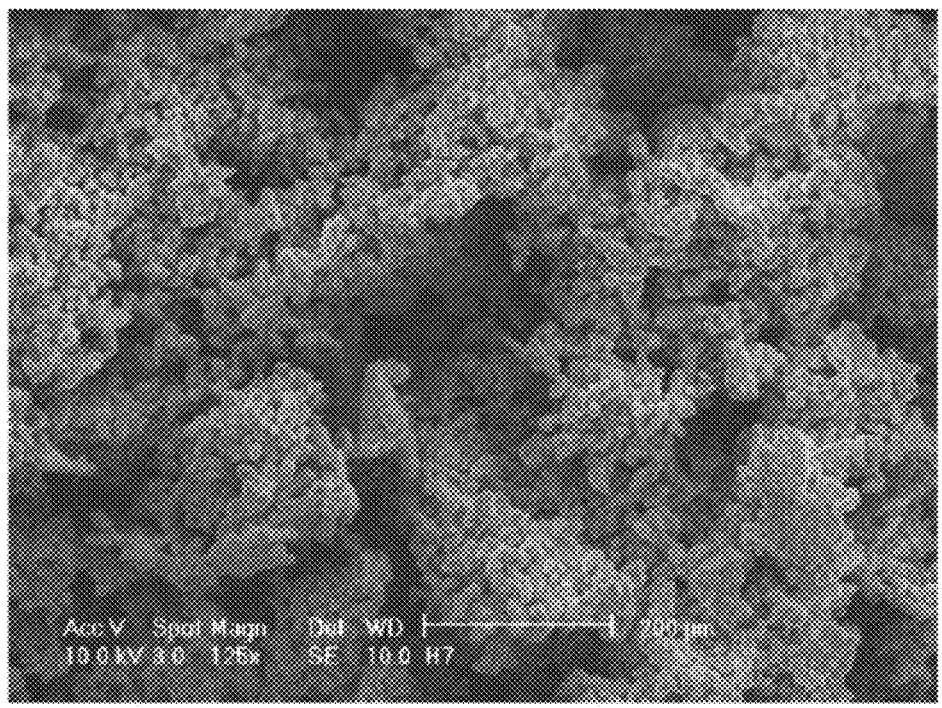
Figure 6D:
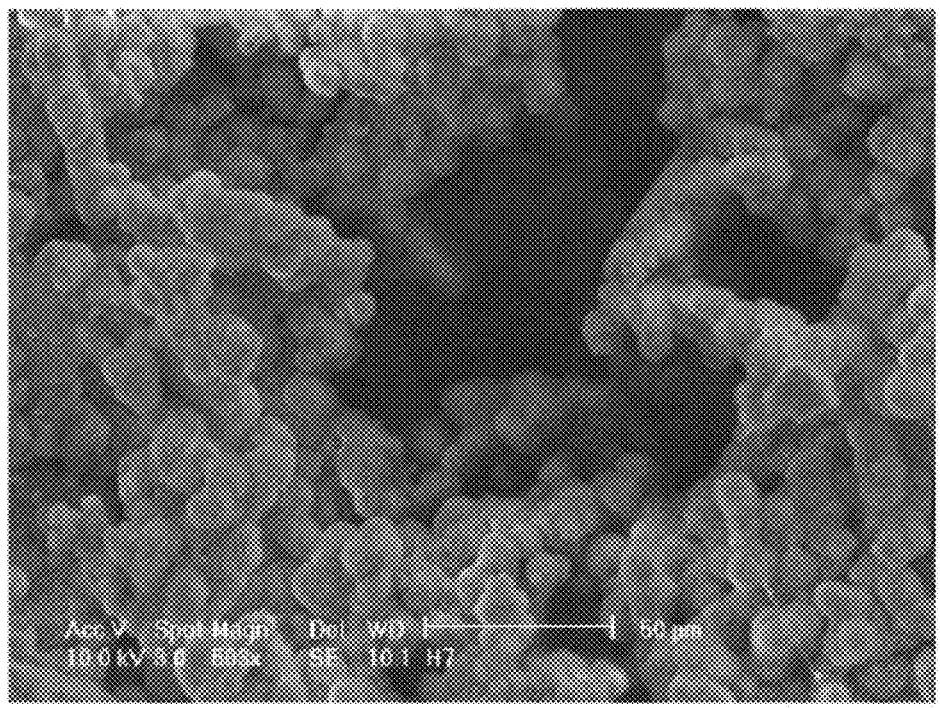
Figure 7A:
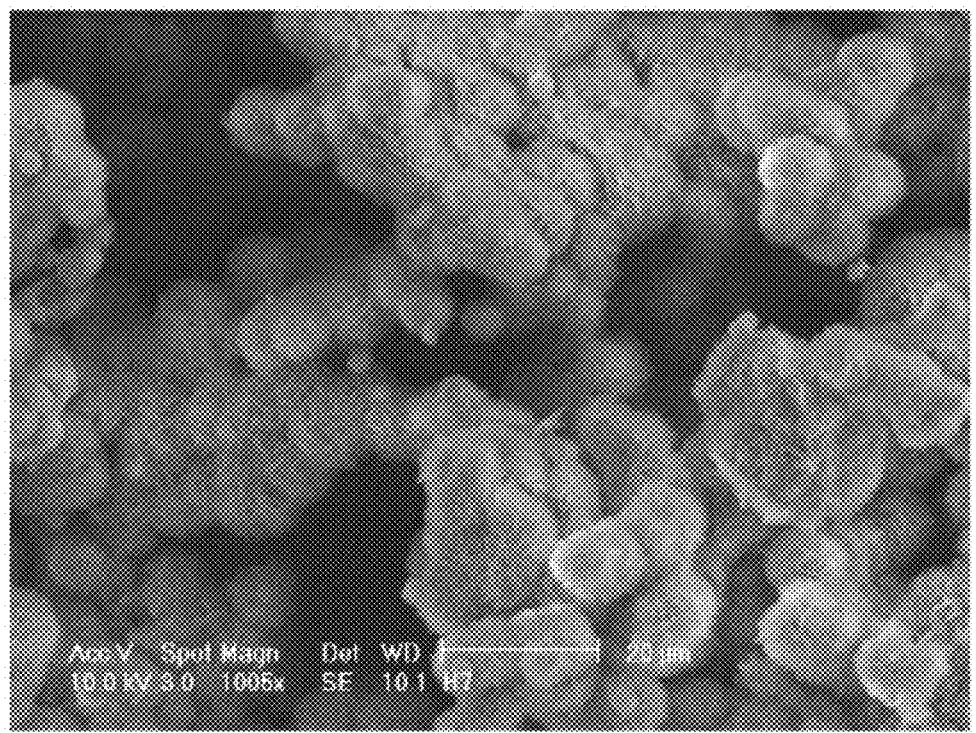
FIG. 7A shows SEM micrographs of the coated Ti (scale bar=20 µm).
Figure 7B:
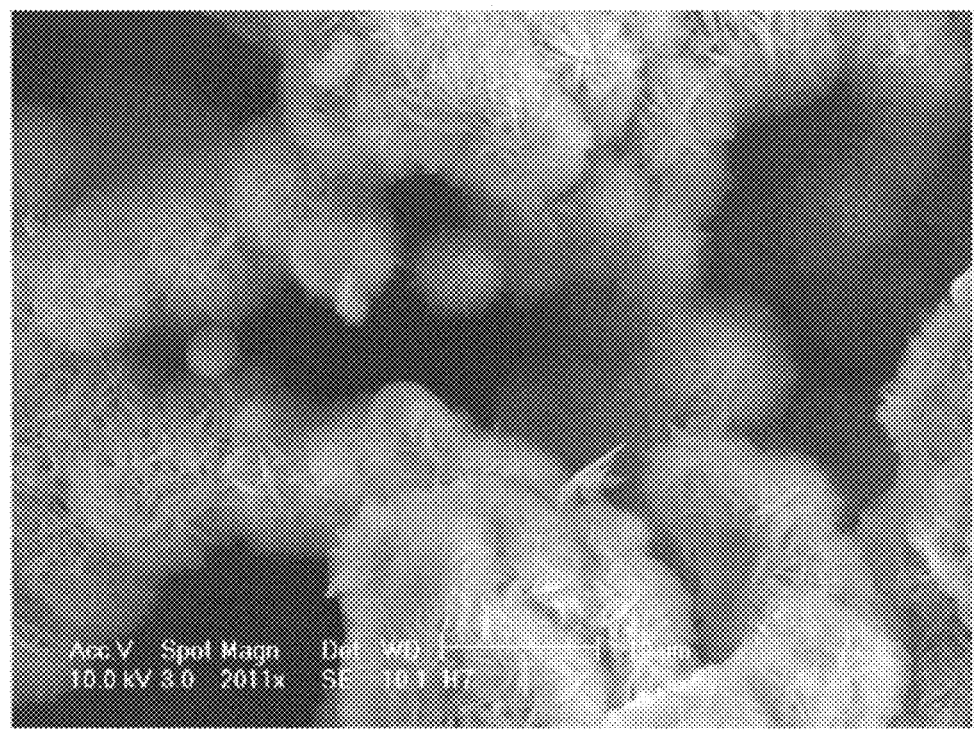
FIG. 7B shows SEM micrographs of the coated Ti (scale bar=10 µm).

FIG. 4A and FIG. 4B show uncoated roughened titanium and coated roughened titanium. Characteristics of the roughened titanium are a 'lava rock' surface structure with a larger pore size between 200-525 μm and a smaller pore size in the range 25-65 μm. The average pore volume=60% and the average surface roughness=132 μm.

Figure 8:
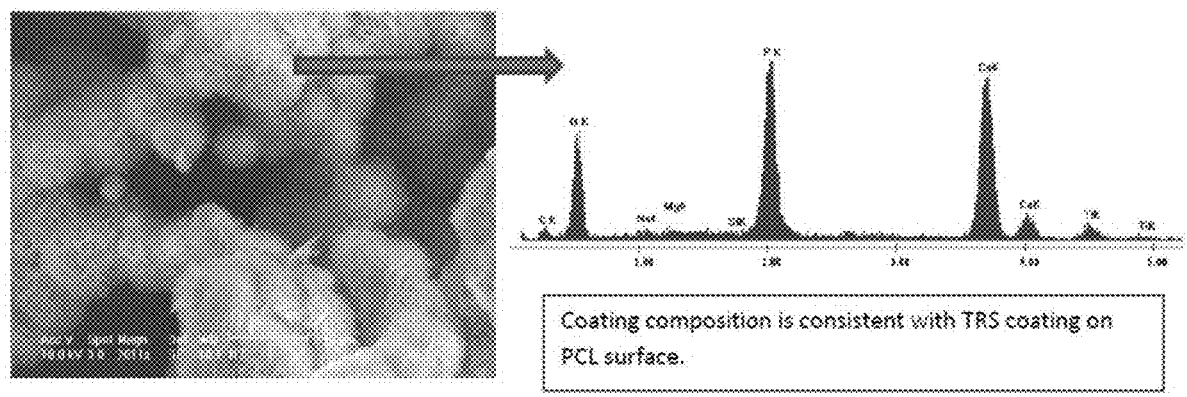
FIG. 8 shows the coating composition on Ti is consistent with the coating on a PCL surface.
Figure 9:
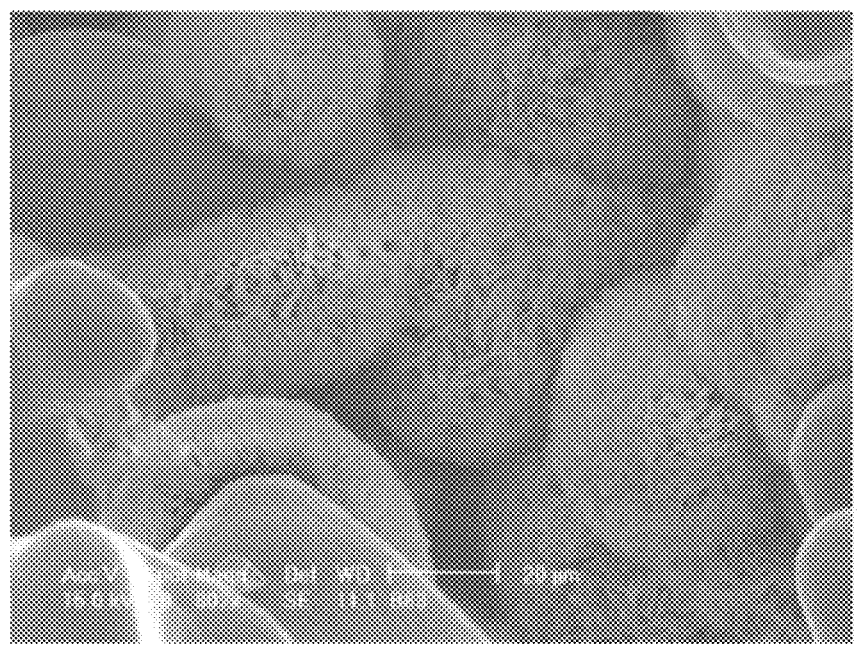
FIG. 9 shows the coating thickness on Ti is in the range of 5-15 µm.

It was shown that the coating morphology and composition on titanium is consistent with the same coating on PCL (see e.g., FIG. 8).

Example 7: Demineralized Bone Matrix (DBM) and Silver Nanoparticles Integrated into Mineral Coated Scaffold The following example describes the incorporation of demineralized bone matrix (DBM) to the mineral coating of the scaffold and silver nanoparticles integrated onto the mineral coating of scaffold.

DBM integrated with the mineral coating is presently thought to improve the characteristics of the mineral-coated scaffold, such as the osteoinductive properties. DBM can be integrated into or onto the mineral coating of the scaffold. DBM, such as demineralized bone extract or gel can be incorporated with the aqueous mineral coating solution in Example 4 to form a mixture of DBM and mineral coating solution to coat a scaffold in a single coating step.

DBM can be coated onto a scaffold pre-coated with the mineral coating. The scaffold can be coated with DBM before, during, or after mineral coating using the methods described herein.

Silver nanoparticles integrated with a scaffold or the mineral coating are presently thought to provide biostatic, anti-infection properties to the mineral-coated scaffold. Silver nanoparticles can be integrated onto the mineral coating as described below. The nanoparticles can also be integrated into the scaffold or coating before, during, or after DBM coating using the methods described herein.

The following describes the incorporation of silver nanoparticles onto a CaP coated scaffold. CaP coated scaffolds are incubated in silver nitrate solution in deionized water (pH 7.0, 5 mL) to synthesize silver particles on the surface or coating. In a set of experiments, CaP coatings are pre-treated by incubating in citric acid solution in deionized water (pH 7.0, 5 mL) prior to silver nitrate incubation.

The concentrations of both solutions are varied (e.g., 1, 5, and 10 mM). Incubation times are also varied (e.g., 0.5, 1, and 4 hr). After citric acid pre-treatment, the resultant CaP coatings can be characterized using FT-IR, and crystallinity index can be calculated from Shemesh's method. The calcium released from citric acid-treated CaP coating in PBS at 37° C. can be quantified by colorimetric assay using Arsenazo III (MP Biochemicals, USA). The release medium can be collected at different times to quantify calcium ions. Fresh PBS can be added for further incubation. The silver particles on CaP coatings can be imaged using FE-SEM and elemental analysis using EDS. The silver particles scraped from CaP coatings can be characterized using XRD.

The silver nanoparticle-integrated mineral-coated scaffold can be further incorporated with DBM as described above. Alternatively, the mineral coating can be incorporated with DBM before the addition of silver nanoparticles.

The DBM is integrated with a scaffold by mixing DBM with an aqueous solution. The aqueous solution can be the mineral coating solution. The aqueous solution can be a weak acid or guanidine hydrochloride. The mixture is constantly agitated for a set amount of time to produce an aqueous demineralized bone extract. The extract can then be filtered to remove any remaining solids, the acid neutralized or removed, and the extract used to coat the porous scaffold.

The DBM and aqueous solution or coating solution is mixed from about 8 to 96 hours. The DBM and aqueous solution is mixed together with constant agitation during that time. After mixing for the appropriate amount of time, the resulting demineralized bone extract can be separated from any insoluble DBM remaining in the solution. The aqueous solution or coating solution comprising the DBM is neutralized to a pH of from about 6.5 to about 7.5 by titration with an appropriate counterion. The scaffold is then incubated according Example 4.

The invention claimed is:

1. A method for producing a mineral coated scaffold comprising:
    contacting a scaffold comprising a matrix material and a modified simulated body fluid, wherein the modified simulated body fluid comprises 20 mM Tris, at least 5 mM $CaCl_2$ and at least 2 mM $KH_2PO_4$; and
    incubating the scaffold and the modified simulated body fluid for a period of time under conditions sufficient to form a mineral coated scaffold,
    wherein the modified simulated body fluid is adjusted to a pH of about 6.5 to about 7.2,
    wherein the mineral coating comprises a carbonate-substituted, calcium-deficient hydroxyapatite component, and the mineral coating has a plate-like nanostructure and a porosity between about 20% and about 28%.

2. The method of claim 1, wherein the matrix material is a biodegradable matrix material.

3. The method of claim 1, wherein the matrix material comprises polycaprolactone (PCL), polyetheretherketone (PEEK), or titanium (Ti).

4. The method of claim 1, further comprising combining NaCl, KCl, $MgCl_2$, $MgSO_4$, $NaHCO_3$, Tris, $CaCl_2$, and $KH_2PO_4$ to form the modified simulated body fluid.

5. The method of claim 4, wherein:
    (i) NaCl has a concentration of about 100 mM to about 200 mM;
    (ii) KCl has a concentration of about 1 mM to about 8 mM;
    (iii) $MgCl_2$ has a concentration of about 0.2 mM to about 5 mM;
    (iv) $MgSO_4$ has a concentration of about 0.2 mM to about 5 mM;
    (v) $NaHCO_3$ has a concentration of about 1 mM to about 100 mM;
    (vi) $CaCl_2$ has a concentration of about 5 mM to about 20 mM;
    (vii) $KH_2PO_4$ has a concentration of about 2 mM to about 10 mM; and
    (viii) Tris has a concentration of 20 mM.

6. The method of claim 4, wherein:
    (i) NaCl has a concentration of about 141 mM;
    (ii) KCl has a concentration of about 4.0 mM;
    (iii) $MgCl_2$ has a concentration of about 1.0 mM;
    (iv) $MgSO_4$ has a concentration of about 0.5 mM;
    (v) $NaHCO_3$ has a concentration of about 4.2 mM;
    (vi) $CaCl_2$ has a concentration of about 5 mM;
    (vii) $KH_2PO_4$ has a concentration of about 2.0 mM; and
    (viii) Tris has a concentration of 20 mM.

7. The method of claim 1, wherein the period of time is from about 5 days to about 28 days.

8. The method of claim 1, wherein the period of time is selected from the group consisting of about 1 day; about 2 days; about 3 days; about 4 days; about 5 days; about 6 days; about 7 days; about 8 days; about 9 days; about 10 days; about 11 days; about 12 days; about 13 days; about 14 days; about 15 days; about 16 days; about 17 days; about 18 days; about 19 days; about 20 days; about 21 days; about 22 days; about 23 days; about 24 days; about 25 days; about 26 days; about 27 days; and about 28 days.

9. The method of claim 1, wherein the period of time is about 5 days to about 14 days.

10. The method of claim 1, further comprising hydrolyzing the scaffold.

11. The method of claim 1, wherein the incubation comprises heating the modified simulated body fluid to a physiologic temperature.

12. The method of claim 11, wherein the physiologic temperature is about 37° C. or the pH is about 6.8.

13. The method of claim 1, wherein incubating comprises replacing the modified simulated body fluid, replenishing the modified simulated body fluid, removing the modified simulated body fluid, or adding the modified simulated body fluid, wherein incubating comprises maintaining a concentration of modified simulated body fluid.

14. The method of claim 1, wherein the coating comprises about 97% hydroxyapatite.

15. The method of claim 1, wherein the coating comprises about 3% octacalcium phosphate.

16. The method of claim 1, wherein the coating comprises between about 100 nm and about 350 nm pore diameter.

17. The method of claim 1, wherein the coating comprises (i) about 1.37 to about 1.61 Ca/P; or (ii) about 1.1 to about 1.3 Ca/P (calcium to phosphate ratio).

18. A mineral coated scaffold produced according to claim 1, comprising a scaffold comprising a matrix material, wherein the mineral coating of the scaffold comprises a carbonate-substituted, calcium-deficient hydroxyapatite component.

19. A mineral coated scaffold comprising a matrix material, wherein the mineral coating comprises a carbonate-substituted, calcium-deficient hydroxyapatite component; and wherein the mineral coating formed from an incubated simulated body fluid comprising 5 mM $CaCl_2$ and about 2 mM $KH_2PO_4$ and the mineral coating comprises a porosity between about 20% and about 28% and a plate-like nanostructure.

20. The mineral coated scaffold of claim 19, wherein the coating comprises:
    (i) about 97% hydroxyapatite;
    (ii) about 3% octacalcium phosphate;
    (iii) between about 100 nm and about 350 nm pore diameter; or
    (iv) about 1.1 to about 1.3 Ca/P; or about 1.37 to about 1.61 Ca/P.

21. The method of claim 1, wherein the modified simulated body fluid further comprises one or more constituents of blood plasma.

22. The method of claim 21, wherein the one or more constituents of blood plasma are ionic.

23. The method of claim 1, wherein the modified simulated body fluid comprises 20 mM Tris, at least 7.5 mM $CaCl_2$ and at least 3 mM $KH_2PO_4$.

24. The method of claim 1, wherein the scaffold is hydrolyzed in a 1.0 M NaOH solution for 60 minutes prior to contacting with the modified simulated body fluid.

25. The mineral coated scaffold of claim 19, wherein the coating comprises at least one of silver particles or demineralized bone matrix.

26. The mineral coated scaffold of claim 25, wherein the silver particles are provided in an amount effective to provide at least one of antimicrobial, antibacterial, biostatic, or anti-infection properties.

27. The mineral coated scaffold of claim 25, wherein the silver particles are provided as silver microparticles or silver nanoparticles.

28. A method, comprising:
functionalizing a surface of a scaffold, wherein the scaffold comprises a matrix material;
contacting the scaffold with a modified simulated body fluid, wherein the modified simulated body fluid comprises 20 mM Tris, at least 5 mM $CaCl_2$ and at least 2 mM $KH_2PO_4$; and
incubating the scaffold and the modified simulated body fluid for a period of time under conditions sufficient to form a mineral coated scaffold, wherein the mineral coating comprises a carbonate-substituted, calcium-deficient hydroxyapatite component, and the mineral coating has a plate-like nanostructure and a porosity between about 20% and about 28% and the modified simulated body fluid is at a pH of 6.5 to 7.2.

29. A method, comprising: hydrolyzing a scaffold;
contacting the scaffold comprising a matrix material and a modified simulated body fluid,
wherein the modified simulated body fluid comprises 20 mM Tris, at least 5 mM $CaCl_2$ and at least 2 mM $KH_2PO_4$; and
incubating the scaffold and the modified simulated body fluid for a period of time under conditions sufficient to form a mineral coated scaffold, the modified simulated body fluid being at a pH of 6.5 to 7.2,
wherein the mineral coating comprises a carbonate-substituted, calcium-deficient hydroxyapatite component, and the mineral coating has a plate-like nanostructure and a porosity between about 20% and about 28%.

* * * * *